United States Patent [19]
Iida et al.

[11] Patent Number: 5,343,855
[45] Date of Patent: Sep. 6, 1994

[54] ENDOSCOPE PIPELINE CONTROLLING APPARATUS AND ENDOSCOPE SYSTEM

[75] Inventors: Yoshihiro Iida, Tama; Masaaki Nakazawa, Hino; Takahiro Kishi, Yokohama; Tsugio Okazaki, Hachioji, all of Japan

[73] Assignee: Olympus Optical Co., Ltd., Tokyo, Japan

[21] Appl. No.: 701,381

[22] Filed: May 16, 1991

[30] Foreign Application Priority Data
May 18, 1990 [JP] Japan .................. 2-128888

[51] Int. Cl.$^5$ .............................. A61B 1/06
[52] U.S. Cl. ................................... 128/6
[58] Field of Search ............... 128/4, 6, 7, 8, 9

[56] References Cited

U.S. PATENT DOCUMENTS

| | | | |
|---|---|---|---|
| 4,281,646 | 8/1981 | Kinoshita | 128/6 |
| 4,402,310 | 9/1983 | Kimura | 128/6 X |
| 4,836,187 | 6/1989 | Iwakoshi et al. | 128/4 |
| 4,860,731 | 8/1989 | Matsuura | 128/4 X |
| 4,991,564 | 2/1991 | Takahashi et al. | 128/4 |

FOREIGN PATENT DOCUMENTS 0278217 8/1988 European Pat. Off. .
0163661 8/1990 European Pat. Off. .

*Primary Examiner*—Robert P. Swiatek
*Attorney, Agent, or Firm*—Armstrong, Westerman, Hattori, McLeland & Naughton

[57] ABSTRACT

An endoscope pipeline controlling apparatus and endoscope system comprising an air feeding pipe communicating with an air feeding pump, a water feeding tank to which is connected a water feeding air feeding pipe branched from a part of the above-mentioned air feeding pipe, a water feeding pipe connected to this water feeding tank, electromagnetic valves fitted to the above-mentioned air feeding pipe and water feeding pipe and connecting pipelines connecting the above-mentioned air feeding pipe and water feeding pipe to communicate with pipelines of an endoscope so that, even if a light source apparatus feeding an illuminating light to the endoscope is not provided with an air feeding and water feeding pipeline controlling apparatus, feeding air and feeding water to the endoscope will be able to be controlled.

26 Claims, 36 Drawing Sheets

T=0.1~60sec

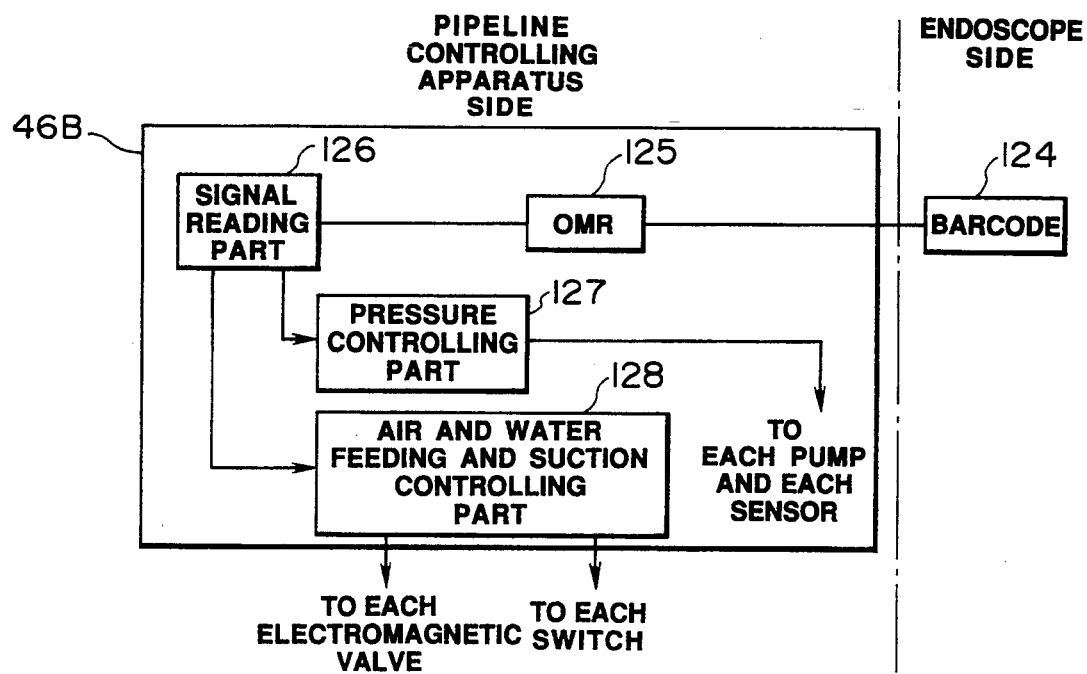
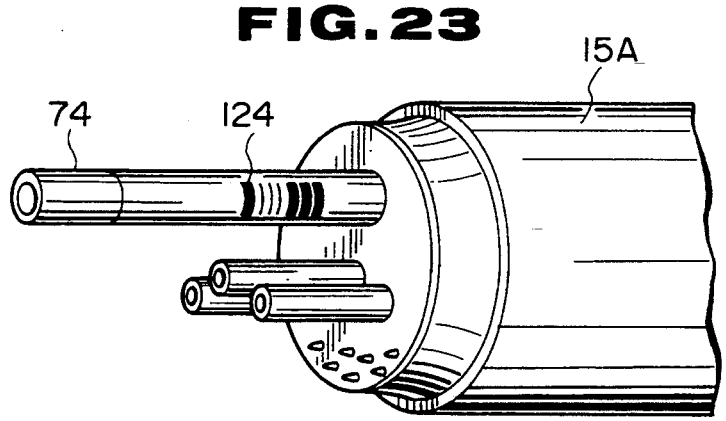

(STANDING BY)

(WATER FEEDING START ⟹ FEEDING AIR+FEEDING WATER)

(WHILE FEEDING WATER (AIR FEEDING ENDS))

(WATER FEEDING ENDS)

(STANDING BY) WASHING WATER (WATER FEEDING TIME)

FIG.27(C)
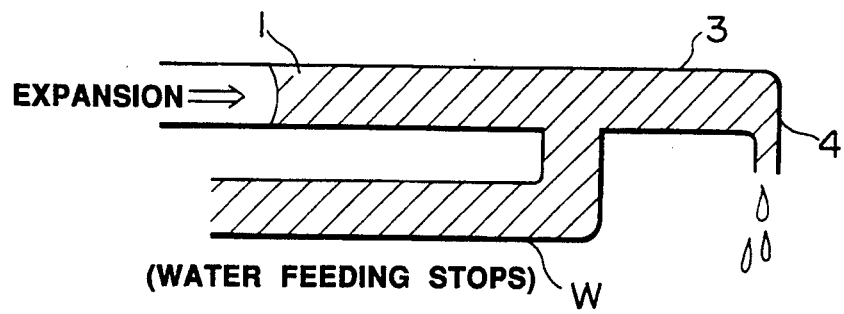
FIG.27(C')
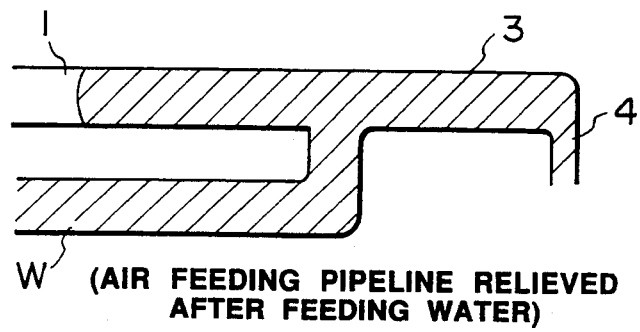
FIG.27(D)
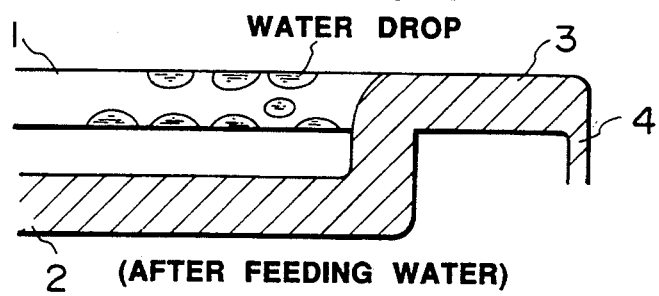
FIG.27(E)
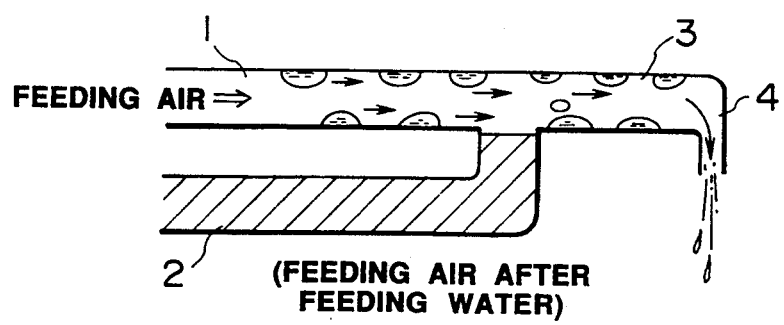

| | FEEDING AIR | FEEDING WATER | WATER FEEDING STARTING TIME -MOMENTARY FEEDING AIR |
|---|---|---|---|
| SW1 ON / OFF | ⎍ | | |
| SW2 ON / OFF | | ⎍ | ⎍ |
| SW3 ON / OFF | | | ⎍ |
| V1 OPENS / CLOSES | ⎍ | | ⎍ |
| V2 OPENS / CLOSES | | ⎍ | ⎍ |
| V3 OPENS / CLOSES | | | |

| | WATER FEEDING STARTING TIME MOMENTARY FEEDING AIR+ FEEDING AIR AFTER FEEDING WATER | WATER FEEDING STARTING TIME MOMENTARY FEEDING AIR+AIR FEEDING PIPELINE RELIEF |
|---|---|---|
| SW1 ON/OFF | | |
| SW2 ON/OFF | ⎍ | ⎍ |
| SW3 ON/OFF | ⎍ | ⎍ |
| SW5 ON/OFF | ⎍ | |
| SW6 ON/OFF | | ⎍ |
| V1 OPENS/CLOSES | ⊓ ⊓ | ⊓ |
| V2 OPENS/CLOSES | ⎍ | ⎍ |
| V3 OPENS/CLOSES | | |
| V4 OPENS/CLOSES | | |
| V5 OPENS/CLOSES | | ⊓ |

(T: 0.1sec~1sec)

T1 = 0.1sec ~ 1sec

T1=0.1sec~1sec
T2=0.1sec~60sec $T_3 = 0.1\,sec \sim 1\,sec$

ENDOSCOPE PIPELINE CONTROLLING APPARATUS AND ENDOSCOPE SYSTEM

BACKGROUND OF THE INVENTION

1. Field of the Invention

This invention relates to an endoscope pipeline controlling apparatus for controlling respective air and water feeding and sucking pipelines

2. Description of the Related Art

Recently, an endoscope has been developed whereby, an elongate insertable section inserted into a body cavity allows organs within the body cavity to be observed and, as required, with a treating instrument inserted through a treating instrument channel allows various therapeutic treatments to be made is extensively utilized and is used not only medically but also industrially to observe and inspect the interiors of such objects as boilers, mechanical and chemical plant pipes or machines.

Further, various electronic endoscopes have been developed in which a solid state imaging device, such as a charge coupled device (CCD), is used as an imaging means in the tip part of an insertable section.

Now, in the case where an endoscope or, particularly, a medical endoscope, is inserted into a body cavity, obstructions such as a body liquid will be deposited on the observing window and will obstruct the observation and, therefore, the observing window will have to be cleaned. Therefore, generally, in an endoscope, the observing window is cleaned by feeding air and water from a nozzle provided in the observing window through an air and water feeding pipeline. Also, in order to observe even the smallest details of the part to be inspected, it is necessary to feed air into the body cavity to separate the body wall and the endoscope tip part from each other.

Therefore, the endoscope is provided with pipelines for feeding and sucking air and water. The air feeding pipeline and water feeding pipeline join with each other on the tip side of the insertable section of the endoscope and communicate with a nozzle opening toward an observing window provided in the tip part. In the case where the observing window is stained with a viscous liquid or dirt, water and air are fed toward the observing window from the above-mentioned nozzle so as to be able to remove the stain.

Therefore, the endoscope apparatus is provided with a controlling means for controlling the switching of the above-mentioned feeding and sucking of air and water. For this controlling means, a mechanical controlling method is already generally used wherein a switching valve provided in an operating section of an endoscope is operated directly with fingers, and an electric controlling method is also commonly used wherein, as shown in the publication of Japanese Patent Application Laid Open No. 75131/1981, a switch is provided in an operating section of an endoscope and is operated with fingers to control electromagnetic valves provided in respective pipelines within a photoelectric source apparatus. As compared with the mechanical controlling method, in the above-mentioned electric method, the automatic feeding of air after the feeding of water and the automatic sucking after the feeding of water are possible so that not only the water evacuation of the pipeline can be improved, but it is also not necessary to provide a switching valve having a complicated structure and low in washability in the pipeline formed within the endoscope and therefore this method is high in washability, and is considered sanitary.

Now, in an endoscope in which respective pipelines for feeding and sucking air and water are controlled by the electric method, a controlling apparatus consisting of electromagnetic valves or the like is required. This controlling apparatus has been provided integrally with a light source apparatus and therefore has become very expensive. Therefore, in case a user having a mechanical controlling method light source apparatus and endoscope wants to buy and use an electric controlling method endoscope, he will have to buy a light source apparatus integral with a controlling apparatus consisting of electromagnetic valves or the like.

Also, in endoscopes of the prior art, as the endoscope is inserted into the body cavity within which the internal pressure is higher than the atmospheric pressure, in case the endoscope is pulled out of the body cavity, the obstructions deposited near the nozzle may flow back into the nozzle. When the endoscope is left as it is or is dipped into a chemical liquid, the obstructions and dirt may coagulate within the nozzle or air and water feeding pipelines. If the nozzle and the like are clogged, the observing window will be no longer able to be washed, and it will be very difficult to remove the coagulated dirt and the endoscope observation will be likely to be greatly obstructed.

Further, as described above, in the endoscope, in order to make the endoscope observation easy, air is constantly fed through an air feeding pipeline to inflate the body cavity wall. So that the body cavity wall may not be varied or damaged by the excess air feed in such case, according to the related art mentioned in the publication of Japanese Patent Application Laid Open No. 22243/1989, the excess air feed is prevented and the pressure within the body cavity is always kept constant lest the pressure within the body cavity be reduced in excess by the sucking operation.

Now, the endoscope inspection applying position can be of such comparatively thick position as a body wall or at such a very thin position as a membrane. In spite of such differences in the body cavity tissue, the air feeding pressure, water feeding pressure and sucking pressure are set to be constant. The above-mentioned pressures are set to be rather low to secure the safety in the very thin body wall position, that is, to prevent a body cavity rupture or mucous membrane adsorption. However, in case a thick body wall position is to be inspected with such a low setting, even if air is fed to secure the visual field, the body cavity interior will not be easily inflated and, when the inspection ends, even in case the fed air is sucked, it will not be easily sucked and the inspection time will be unduly long.

On the other hand, various kinds of endoscopes are prepared in conformity with the applying positions of the examined body to be observed, and the respective inserted position diameters, optical systems, pipeline inside diameters and pipeline lengths are different.

Further, in the endoscope in which the pipeline is controlled by the electric method shown in the above described Japanese Patent Application Laid Open No. 75131/1981, in order to improve the evacuation of water droplets on the objective lens surface after feeding water, as shown in the publication of Japanese Patent Application Laid Open No. 220833/198, air is automatically fed after feeding water or, as shown in the publication of Japanese Patent Application Laid Open No. 277931/1987, the air feeding pipeline is automatically made to vent to the atmosphere after feeding water.

Now, in the endoscope in which, as shown in FIG. 27, the air feeding pipeline 33 and water feeding pipeline 34 join with each other on the insertable section tip side and communicate with the nozzle 36 through the air and water feeding joint pipeline 35, when water is fed to the water feeding pipeline 2 from the state shown in FIG. 27(A), as shown in FIG. 27(B), the pressure of the pump which is a water feeding means, that is, the water feeding pressure will compress the gas within the air feeding pipeline and therefore the washing water from the joining point 35 will flow back into the air feeding pipeline 33. When the water feeding is stopped, the above-mentioned compressed air will expand and will push out the washing water which has flowed back into the air feeding pipeline 33, as shown in FIG. 27(C). However, even if the washing water thus having flowed back into the air feeding pipeline 33 is pushed out, water drops will remain on the inside wall of the air feeding pipeline 33, as shown in FIG. 27(D). Even if air is fed to blow away the water drops on the observing window after feeding water, as shown in FIG. 27(E), the remaining water drops will fly out successively. Thus, the water drops on the observing window will not be easily removed. In the case of the control by making the air feeding pipeline 33 leak to the atmosphere after feeding water, as shown in FIG. 27(C'), the water having flowed back into the above-mentioned air feeding pipeline 33 will remain as it is. If feeding air is repeated several times, water will be likely to spread out of the leaking pipeline.

Also, as described above, the air feeding pipeline and water feeding pipeline of the endoscope join with each other on the tip side of the insertable section and communicate with the nozzle opening toward the objective lens provided in the tip part so that, in case the objective lens is stained by the mucous liquid and dirt within the body cavity, air and water will be fed toward the objective lens from the above-mentioned lens so as to be able to remove the stain. Further, the endoscope has a function of automatically sucking after feeding water to improve the water cut of the water drops deposited by the water feeding on the objective lens surface.

However, in the above-mentioned conventional endoscope air and water feeding and sucking apparatus, particularly one in which sucking occurs automatically after feeding water, a comparatively high suction will be required in order to suck and remove the water drops on the objective lens with a momentary suction after feeding water. However, the sucker usually used for the endoscope sucks the mucous liquid or the like obstructing the observation in the endoscope inspection and is set to be under such pressure so as to not damage the tissue even if the body cavity wall or the like is sucked by mistake during the inspection.

Therefore, the suction pump used for suction shall be a safe pump low in the closing pressure and shall make the sucking pipeline on the sucker side leak to the atmosphere also from the suction controlling valve when no suction is made in order to increase safety. Even if such a sucking means low in suction is used to momentarily suck after feeding air, as just after the leaking state, the sucking pressure will not be transmitted to the channel opening provided at the tip of the insertable section of the endoscope. It has been difficult to suck the water drops on the objective lens.

Further in the above-described endoscope apparatus, in feeding air and water by one pump, at the time of feeding water, if spray water is fed by opening both the air feeding pipeline and the water feeding pipeline, in case the operator carelessly tumbles the water feeding tank during the inspection, a liquid surface will be made in the opening 5 of the water feeding pipeline and air and washing liquid may be simultaneously sucked up. Then, an air layer and a washing liquid layer will be alternately formed within the water feeding pipeline. In such a state, the pipeline resistance of the water feeding pipeline will become so large that, in case spray water is to be fed again, the entire pressure of the pump will escape to the air feeding pipeline side having a lower pipeline resistance than the water feeding pipeline, and water will no longer come out of the nozzle. In the case of such a state, the inspection will be stopped at once and the spray water feeding control will have to be switched over to the ordinary water feeding control. In the above, resumption of feed water becomes complicated, long and inflicts pain upon the patient.

SUMMARY OF THE INVENTION

An object of the present invention is to provide an endoscope pipeline controlling apparatus wherein, when an endoscope having electric control of feeding and sucking air and water, even a light source apparatus lacking a pipeline controlling apparatus such as electromagnetic valves, will be able to be used.

Another object of the present invention is to provide an endoscope pipeline controlling apparatus wherein, even in case dirt or the like flows back into the nozzle, air feeding pipeline or water feeding pipeline, such dirt or the like will be able to be discharged out without becoming coagulated and becoming unremovable.

Further, another object of the present invention is to provide an endoscope pipeline controlling apparatus wherein, irrespective of the differences of the endoscope pipeline diameter and length and the applied inspected position, the endoscope observation and inspection can be made safely under an always optimum set pressure, without needlessly lengthening the inspecting time.

Furthermore, another object of the present invention is to provide an endoscope pipeline controlling apparatus wherein, at the time of feeding water, the washing water will be prevented from flowing back into the air feeding pipeline from the joining point and, even if air is fed after feeding water, water drops will not continue to come out and the evacuation of water droplets will be improved.

Further, another object of the present invention is to provide an endoscope pipeline controlling apparatus wherein, even in case a safe pump having a comparatively low closing pressure, the water drops on the observing window will be able to be well blown away by feeding air after feeding water and the evacuation of water droplets will be able to be improved.

Furthermore, another object of the present invention is to provide an endoscope pipeline controlling apparatus wherein, through a system in which the suction can be made after feeding water by the safe suction pump low in the closing pressure, the water drops on the observing window can be positively sucked and removed.

Further an object of the present invention is to provide an endoscope pipeline controlling apparatus wherein, through a system in which air and water can be fed by one pump, spray water can be positively fed without losing the ability to feed water.

The endoscope pipeline controlling apparatus of this invention comprises a pipeline controlling means for controlling feeding and sucking air and water, a leading pipeline connecting the above-mentioned pipeline controlling means to an air feeding pump provided outside the endoscope and a connecting pipeline connecting a pipeline provided within the endoscope to the above-mentioned pipeline controlling means.

The endoscope system of this invention includes a light source apparatus internally provided with a light source feeding an illuminating light to the endoscope and provided with an air feeding pump, a pipeline controlling means controlling feeding and sucking air and water and provided separately from the above-mentioned light source apparatus and an endoscope connected to the above-mentioned light source apparatus and pipeline controlling apparatus.

The other features and advantages of this invention will become apparent enough with the following explanation.

BRIEF DESCRIPTION OF THE DRAWINGS

FIG. 1 is a pipeline diagram of an air and water feeding apparatus.

FIG. 2 is a timing chart showing operation timings of respective switches and valves.

FIG. 3 is a schematic explanatory view showing an electronic endoscope.

FIG. 4 is a perspective view showing a connector and an adapter to be combined with this connecter.

FIG. 5 is an explanatory view showing the connector and adapter as combined with each other.

FIG. 6 is a schematic general formation view of an endoscope and endoscope air and water feeding apparatus.

FIG. 7 is a formation view of a locking mechanism of the apparatus shown in FIG. 1.

FIG. 8 is an explanatory view showing the operation of the apparatus shown in FIG. 1.

FIG. 9 is a pipeline diagram for sensing the air and water feeding pipelines as clogged.

FIG. 10 is a timing chart showing operation timings of respective valves and pressure sensors.

FIG. 11 is a general formation view of an integral type endoscope air and water feeding controlling apparatus.

FIG. 12 is an appearance view of an endoscope connector.

FIG. 13 is an appearance view of an adapter for the integral type apparatus in FIG. 11 and the endoscope connector.

FIG. 14 is an appearance view of an adapter for the separate type apparatus in FIG. 3 and the endoscope connector.

FIG. 15 is an appearance view of the adapter in FIG. 13 as fitted to the connector in FIG. 12.

FIG. 16 is an appearance view of the adapter in FIG. 14 as fitted to the connector in FIG. 12.

FIGS. 17 to 23 relate to the third embodiment.

FIG. 17 is a general formation view of an endoscope and an endoscope fluid controlling pipeline system and controlling system.

FIG. 18 is a timing chart for feeding, sucking and refluxing air and water.

FIG. 19 is a timing chart for stopping feeding, sucking and refluxing air after feeding water.

FIG. 20 is a schematic formation view of a controlling part and code memorizing part.

FIG. 21 is a schematic formation diagram showing a modification.

FIG. 22 is a schematic formation diagram of an endoscope and video processor showing a modification.

FIG. 23 is an appearance view of a tip part of a connector of an endoscope.

FIG. 24 is a pipeline diagram of an air and water feeding apparatus.

FIG. 25 is a time chart showing operation timings of respective switches and valves.

FIG. 26 shows explanatory views showing the case of feeding air for a fixed time simultaneously with feeding water.

FIG. 27 shows explanatory views for explaining a prior art example.

FIGS. 28 and 29 relate to a modification of the apparatus of the fourth embodiment.

FIG. 28 is a pipeline diagram of an air and water feeding apparatus.

FIG. 29 is a timing chart showing operation timings of respective switches and valves.

FIGS. 30 and 31 relate to another modification of the fourth embodiment.

FIG. 31 is a time chart of respective switches and valves.

FIGS. 32 and 33 relate further to another modification.

FIG. 32 is a pipeline diagram.

FIG. 33 is a time chart showing operating states.

FIGS. 34 and 35 relate to another modification.

FIG. 34 is a pipeline diagram.

FIG. 35 is a time chart showing operation timings of respective switches and valves.

FIG. 36 is a pipeline diagram of an air and water feeding apparatus.

FIG. 37 is a timing chart view for explaining the operation in FIG. 36.

DESCRIPTION OF THE PREFERRED EMBODIMENTS

Figure 1:
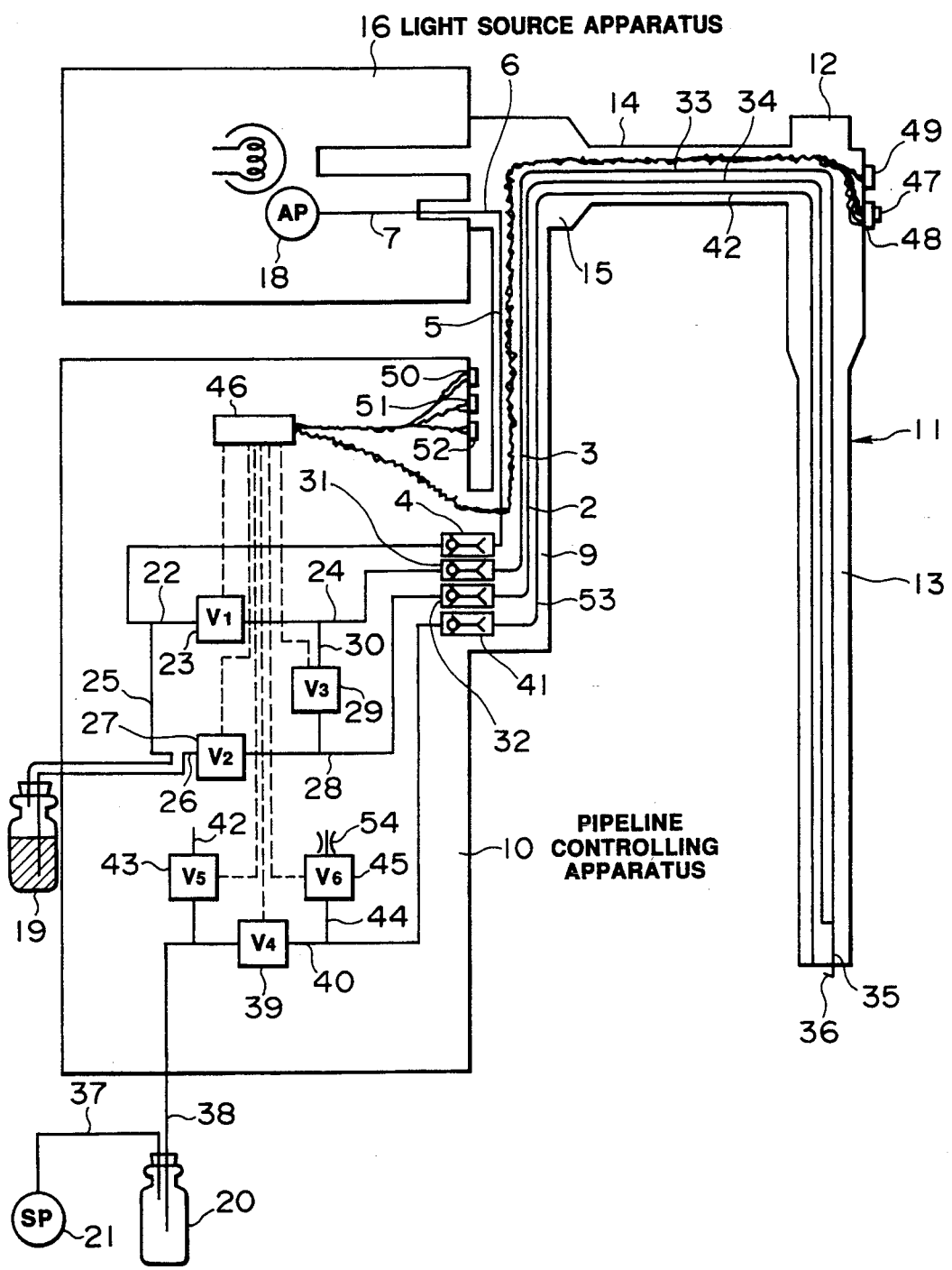
FIGS. 1 to 3 relate to the first embodiment of the present invention.
Figure 2:
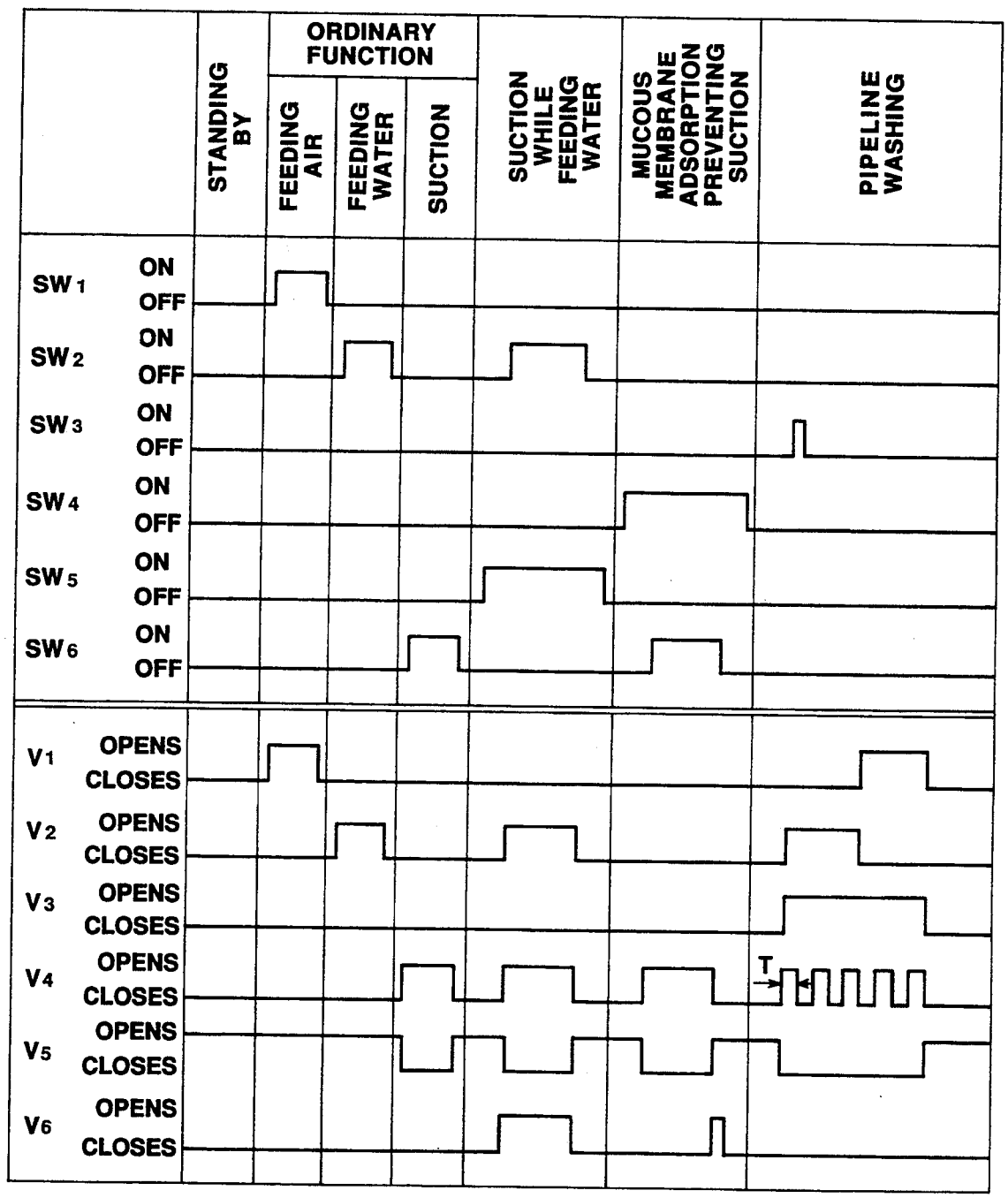
Figure 3:
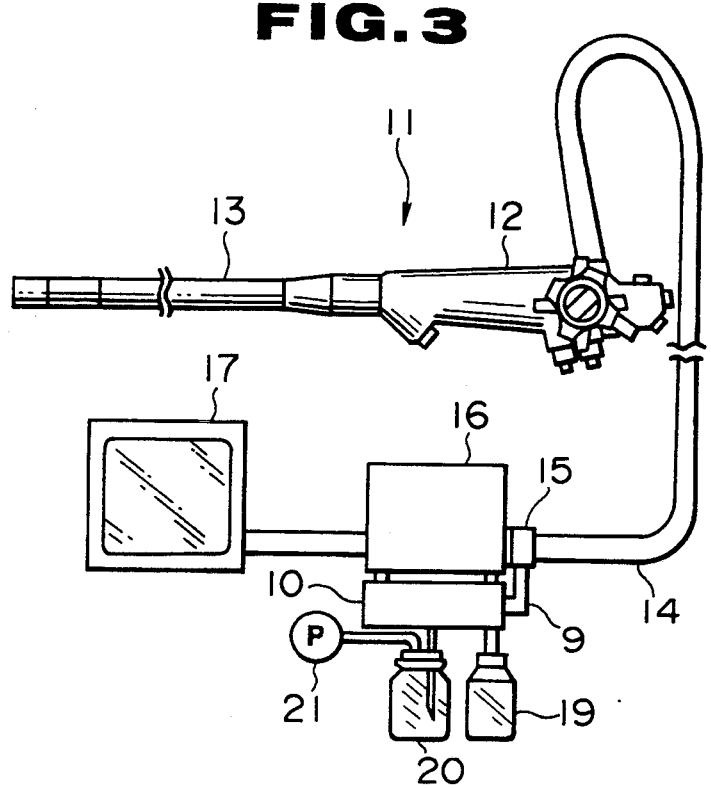

FIGS. 1 to 3 show a first embodiment of the apparatus of the present invention.

In FIG. 3, the reference numeral 11 represents an electronic endoscope as an example to which the apparatus of this embodiment is applied. An elongate insertable section 13 having a tip forming part and curvable part is extended forward of an operating section 12 which is also a holding part on the hand base side. On the other hand, a universal cord 14 is extended from the side of this operating section 12 and is connected through a connector 15 to a light source apparatus 16 provided internally with, for example, a video processor. The above-mentioned light source apparatus 16 has a signal processing circuit processing an imaging signal from the electronic endoscope 11, transmits the processed video signal to a connected monitor 17 to display the image and is internally provided with an air feeding pump 18. The connector 15 is removably provided with a connecting part 9 connecting a later described pipeline provided within a pipeline controlling apparatus 10 controlling feeding and sucking air and water and respective pipelines provided within the endoscope 11. The controlling apparatus 10 is fitted with a water feeding tank 19 connected through a later described pipeline and storing a washing liquid. The pipeline controlling apparatus 10 is further fitted with a suction bottle 20 and suction pump 21 connected also through later described pipelines. By the way, the endoscope to which is applied the apparatus of the present invention is not limited to the above-mentioned endoscope. The apparatus of the present invention can be naturally applied also to a fiber endoscope and the like.

In the pipeline diagram shown in FIG. 1, an air feeding pipeline 7 within the light source apparatus is connected to the air feeding pump 18 provided within the light source apparatus 16 and a first fed air leading pipeline 6 provided within the connector 15 of the endoscope 11 and a second fed air leading pipeline 5 provided within the connecting part 9 are connected through a joint 4 to a first air feeding pipeline 22 within the pipeline controlling apparatus 10. This first air feeding pipeline 22 is provided with a first electromagnetic valve (V1) 23 to which is connected a second air feeding pipeline 24. A water feeding air feeding pipeline 25 is branched and is connected in the course of the above-mentioned air feeding pipeline 22 and to the water feeding tank 19. A first water feeding pipeline 26 is connected to the above-mentioned water feeding tank 19 to which is connected a second water feeding pipeline 28 through a second electromagnetic valve (V2). The above-mentioned second air feeding pipeline 24 and second water feeding pipeline 28 are connected with each other through an air feeding pipeline washing pipeline 30 having a third electromagnetic valve (V3) 29 interposed in the course. The above-mentioned second air feeding pipeline 24 and second water feeding pipeline 28 are fitted at the ends, respectively, with joints 31 and 32 and are connected to an air feeding pipeline 33 and water feeding pipeline 34 on the endoscope side, respectively, through an air feeding pipeline 2 and water feeding pipeline 3 provided within the connecting part 9. The air feeding pipeline 33 and the water feeding pipeline 34 join with each other on the tip side of the endoscope insertable section 13 to form an air and water feeding pipeline 35 which communicates with a nozzle 36 opening toward the observing window in the endoscope tip part. On the other hand, a first sucking pipeline 37 is connected to the suction pump 21 and suction bottle 20 to which is connected a second sucking pipeline 38. A third sucking pipeline 40 is connected to the second sucking pipeline 38 through an electromagnetic valve (V4) 39. This third sucking pipeline 40 is fitted at the end with a joint 41 and is connected to a sucking pipeline 42 on the endoscope side through a sucking connecting pipeline 53 provided within the connecting part 9. A venting pipeline 42 is branched from the second sucking pipeline 38 and communicates with the atmosphere through a fifth electromagnetic valve (V5) 43. A sucked amount adjusting pipeline 44 is branched from the third sucking pipeline 40 and communicates with the atmosphere through a sixth electromagnetic valve (V6) 45 and variable orifice 54. Further, the above-mentioned first to sixth electromagnetic valves 23, 27, 29, 39, 43 and 45 are respectively electrically connected to a controlling part 46. On the other hand, to this controlling part 46 are connected switches (SW1) 47, (SW2) 48 and (SW6) 49 provided in the operating section 12 of the endoscope 11 and switches (SW3), 50, (SW4) 51 and (SW5) 52 provided in the sheath of the pipeline controlling apparatus 10.

The operation shall be explained in the following. First of all, air and water are fed by switching on the switches 47 and 48 provided in the operating section 12. That is to say, in the case of feeding air, when the switch 47 is switched on, the first electromagnetic valve 23 will be opened by the controlling part 46 and air will be fed through the air feeding connecting pipeline 3 and air feeding pipeline 33. On the other hand, in the case of feeding water, when the switch 48 is switched on, the second electromagnetic valve 27 will be opened in the same manner by the controlling part 46 and washing water will be fed to the water feeding connecting pipeline 2 and water feeding pipeline 34.

Then, a suction is made by switching on the switch 49 provided in the operating section 12. That is to say, while usually only the fifth electromagnetic valve 43 is opened and is standing by, when the switch 49 is switched on, by the operating part 46, as operatively connected with switching on the switch 49, the fifth electromagnetic valve 43 will be closed, the fourth electromagnetic valve 39 will be opened and the venting pipeline 42 and sucking connecting pipeline 53 will be opened to suck.

In the case of sucking while feeding water, first the switch 52 will be switched on. This switch is used to switch usual feeding water and feeding water while sucking during feeding water over to each other. Therefore, while switch 52 is on, and the switch 48 feeding water is switched on, the controlling part 46 will sense the signal, will open the second electromagnetic valve 27 and will simultaneously automatically open the fourth electromagnetic valve 40 and sixth electromagnetic valve 45. When the switch 48 is switched off at the time when feeding water ends, the fourth electromagnetic valve 40, sixth electromagnetic valve 45 and second electromagnetic valve 27 will be closed together.

In the case of sucking while feeding water, if the sucked amount is adjusted in advance by the variable orifice 54 so that the fed water amount=sucked amount, the body cavity volume will not vary while feeding water and it will be safe.

In order to control the mucous membrane adsorption preventing sucking for preventing the mucous membrane from being adsorbed, first of all, the switch 51 is switched on. This switch 51 switches the ordinary suction and mucous membrane adsorption preventing suction over to each other. When this switch 51 is on, if the switch 49 is switched on, by the controlling part 46, the fifth electromagnetic valve 43 standing by will be closed and, at the same time, the fourth electromagnetic valve 39 will be opened for sucking. When the switch 49 is switched off, as operatively connected with it, the fifth electromagnetic valve 43 will be opened, at the same time, the fourth electromagnetic valve 39 will be closed and further the sixth electromagnetic valve 45 will be opened for a fixed time and will then return to stand by so that a mucous membrane adsorption releasing pipeline may be temporarily made to communicate with the atmosphere, the negative pressure within the pipeline may be removed and the mucous membrane adsorption may be prevented.

The pipelines of the endoscope are washed by momentarily switching on the switch 50. That is to say, when the switch 50 is switched on, the controlling part 46 will sense it and will automatically make such control as in the following. First of all, the third electromagnetic valve 29 and second electromagnetic valve 26 will be simultaneously opened, the air feeding pipeline 33 and water feeding pipeline 34 will be washed for a fixed time and then the second electromagnetic valve 26 will be closed so that the washing of the air feeding pipeline 33 and water feeding pipeline 34 may end. Then, both pipelines will be controlled to remove water, the first electromagnetic valve 23 will be opened, the water feeding pipelines 34 and air feeding pipeline 33 will have water removed and then will e closed so that both pipelines may be washed and have water removed by a one-touch operation of pushing the switch 50.

On the other hand, on the sucking pipeline side, when the switch 50 is switched on, while the fifth electromagnetic valve 43 and sixth electromagnetic valve 45 remain both closed, the fourth electromagnetic valve 39 will be intermittently opened, washing water will be sucked up form the insertable section tip, the pipelines will be washed for a fixed time and then the fourth electromagnetic valve 39 will return to stand by to complete the washing.

Figure 4:
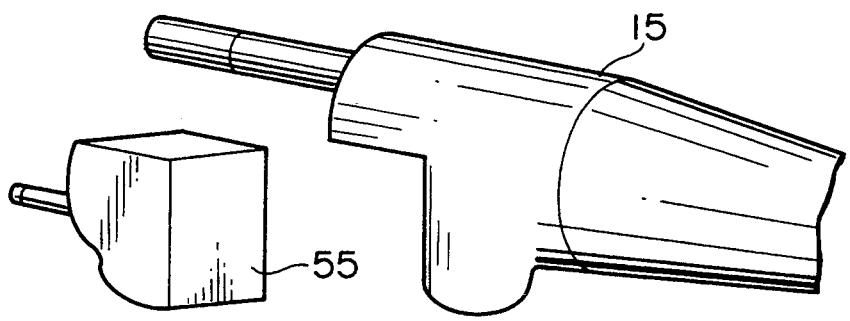
FIGS. 4 and 5 relate to a modification of the apparatus of the first embodiment.
Figure 5:
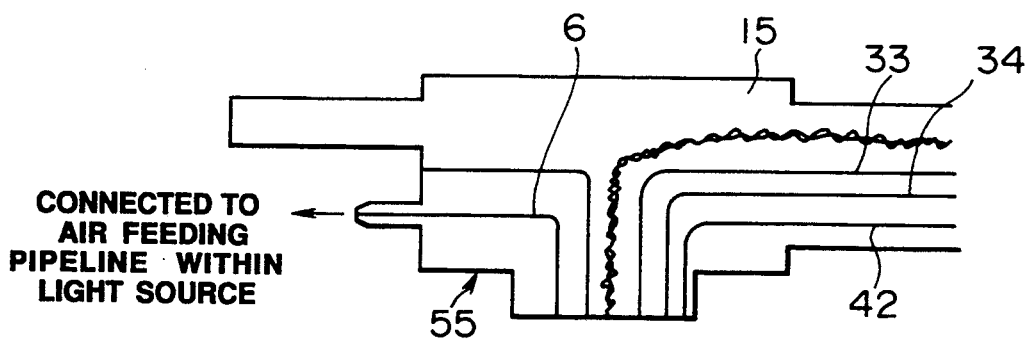

FIGS. 4 and 5 relate to a modification. FIG. 4 is a perspective view showing a connector and an adapter to be combined with this connector. FIG. 5 is an explanatory view showing the connector and adapter as combined with each other.

In the above-described embodiment, the first fed air leading pipeline 6 is housed in the connector 15 but, as shown in Figs. 4 and 5, the first fed air leading pipeline 6 may be provided within an adapter 53 provided separately from the connector 15 and used as combined with connector 15.

FIGS. 6 to 16 show the second embodiment of the present invention.

Figure 6:
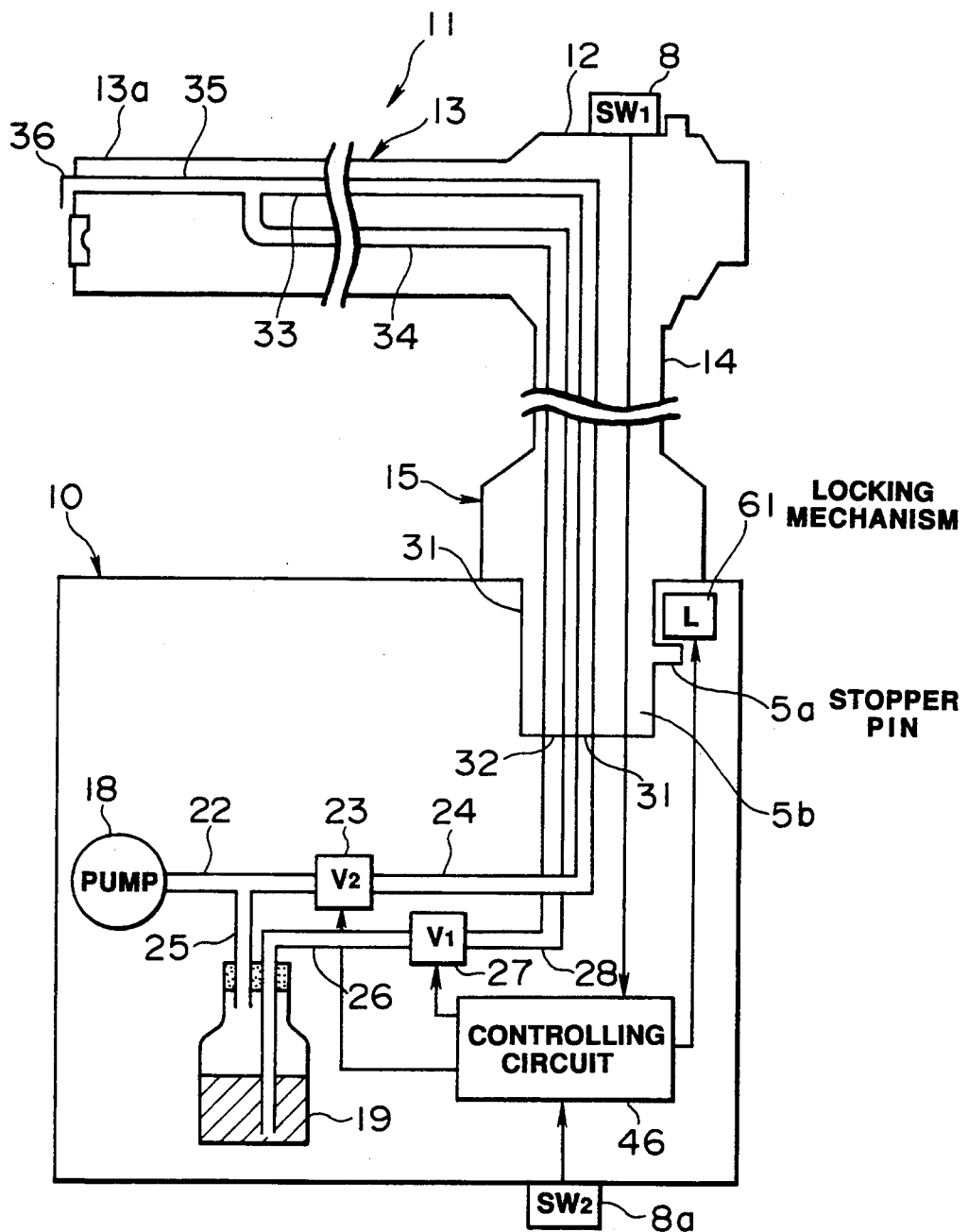
FIGS. 6 to 16 relate to the second embodiment.

The endoscope apparatus shown in FIG. 6 comprises an electronic endoscope 11, an endoscope air and water feeding controlling apparatus 10 for feeding air and water to the endoscope 11 as removably engaged with this endoscope 11 and a light source apparatus not illustrated separate from this controlling apparatus.

As shown in FIG. 6, the endoscope 11 comprises an elongate flexible insertable section 13 and an operating section 12 provided at the rear end of this insertable section. A flexible universal cord 14 is extended sidewise from the above-mentioned operating section 12 and is provided at the end with a connector 15 which is removably engageable with the above-mentioned endoscope air and water feeding controlling apparatus 10.

The insertable section 13 of the above-mentioned endoscope 11 has a rigid tip part 13a which is provided with an illuminating window and observing window not illustrated and an air and water feeding nozzle 36.

A light distributing lens not illustrated is fitted inside the above-mentioned illuminating window and a light guide not illustrated consisting of a fiber bundle is provided at the rear end of this light distributing lens so that an illuminating light may be fed from a light source apparatus, not illustrated.

A solid state imaging device, not illustrated, is arranged inside the above-mentioned observing window and outputs an electric signal to a video processor, not illustrated, and a monitor, not illustrated, displays an endoscope image by a signal output by the video processor. By the way, the endoscope 11 may be an optical fiber endoscope instead of the electronic endoscope.

An air and water feeding pipe 35 is connected to the nozzle 36 on the rear end side and is separated in the midway of the insertable section 13 into two pipelines of an air feeding pipe 33 and water feeding pipe 34 which are inserted through the insertable section 13, operating section 12, universal cord 14 and connector 15 and communicate respectively with the nozzle 36.

This operating section 12 is provided with an air and water feeding switch (SW1) 8 giving an instruction of feeding air or water to a pipeline controlling apparatus 10.

On the other hand, the pipeline controlling apparatus 10 is internally provided with an air feeding pump 18 which is a pressurized air feeding source and is provided with a water feeding tank 19 communicating with the air feeding pump 18 through a later described pipeline. A first air feeding pipeline 22 is connected to this air feeding pump 18 and is provided with a second electromagnetic valve (V2) 23 which connects a second air feeding pipe 24 fitted at the end with a first joint 31 and connected with the air feeding pipe 33 of the endoscope 11 through this first joint 31. A water feeding pressurized pipeline 25 is branched and connected to the above-mentioned first air feeding pipeline 22 in the midway and is connected to the above-mentioned water feeding tank 19 to communicate with the space above the stored water surface within the tank 19. A first water feeding pipeline 26 is connected to the water feeding tank 19 with the sucking port dipped in the stored water. A second water feeding pipeline 28 is connected to this first water feeding pipeline 26 through a first electromagnetic valve (V1) 27, is fitted at the end with a second joint 32 and is connected with the water feeding pipe 34 of the endoscope 11 through this second joint 32. The first joint 31 and second joint 32 are removably connected, respectively, to the air feeding pipe 33 and water feeding pipe 34 of the endoscope 11.

The pipeline controlling apparatus 10 is provided with a controlling circuit 46 as a controlling means for controlling feeding air and water. This controlling circuit 46 electrically connects the above-mentioned second electromagnetic valve 23 and first electromagnetic valve 27 to control opening and closing the valves.

Also, this controlling circuit 46 connects the air and water feeding switch 8 of the endoscope 11 and a releasing switch 8a as a releasing instruction means provided, for example, in the sheath of the pipeline controlling apparatus 10. Further, the pipeline controlling circuit 10 has a locking mechanism (L) 61 engaging with the connector 15 of the endoscope 11 and locking the connector 15 lest it should drop from the engagement. The controlling circuit 46 connects this locking mechanism 61 and controls locking and unlocking this locking mechanism 61.

Figure 7:
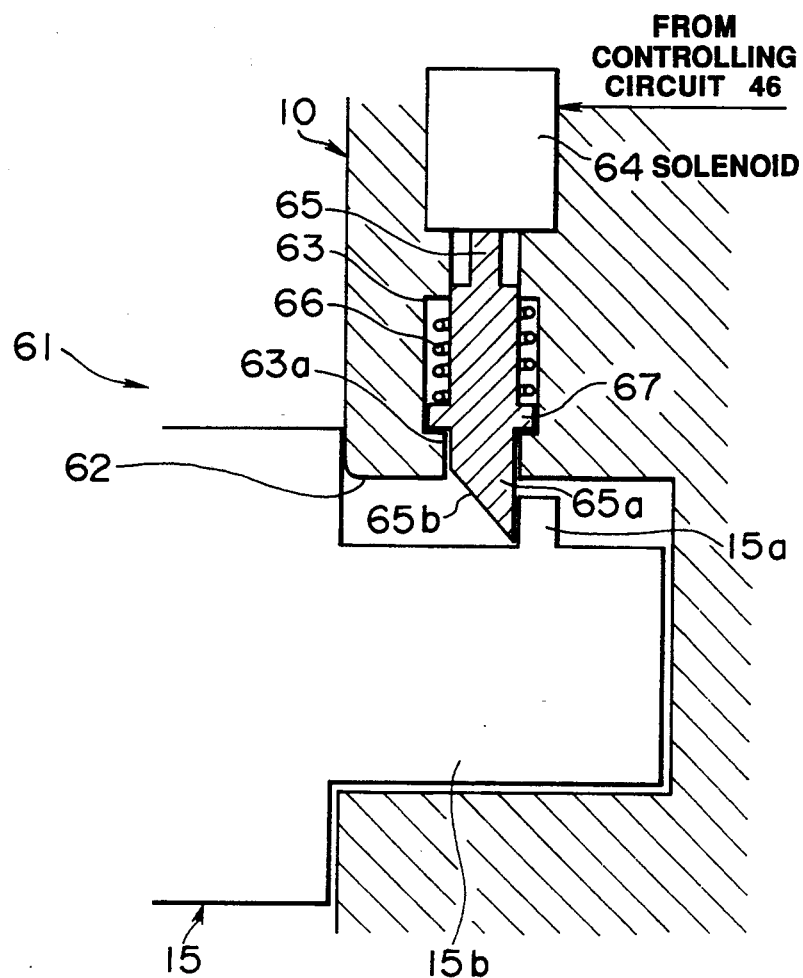

As shown in FIGS. 6 and 7, the connector 15 of the endoscope 11 has a stopper pin 15a projecting out on the side so that, in case the engaging part 15b of the above-mentioned connector 15 and the engaging hole 62 of the pipeline controlling apparatus 10 are engaged with each other, the stopper pin 15a may act to prevent them from being disengaged.

As shown in FIG. 7, the locking mechanism 61 of the pipeline controlling apparatus 10 is internally provided in a side hole 63 provided on the side of the engaging hole 62 and is provided with a solenoid 64 driven and controlled by the controlling circuit 46, a vertically moving pin 65 vertically moved by the operation of the solenoid 64 and an energizing spring 66 loosely fitted on the outer peripheral side of the vertically moving pin 65. The vertically moving pin 65 has in the course a flange part 67 contacting the edge side of the projecting part 63a of the above-mentioned side hole 63 and preventing the vertically moving pin 65 from being pulled out of the side hole 63. This flange part 67 prevents also the energizing spring 66 from dropping off the vertically moving pin 65. The vertically moving pin 65 has on the tip side a tip part 65a contacting the stopper pin 15a of the above-mentioned connector 15 to lock the connector 15 and having a slope 65b.

In this formation, when the air and water feeding switch 8 is pushed, the pipeline controlling apparatus 10 will issue an instruction from the controlling circuit 46 and the first electromagnetic valve 27 and second electromagnetic valve 23 will open or close to feed air or water.

Figure 8:
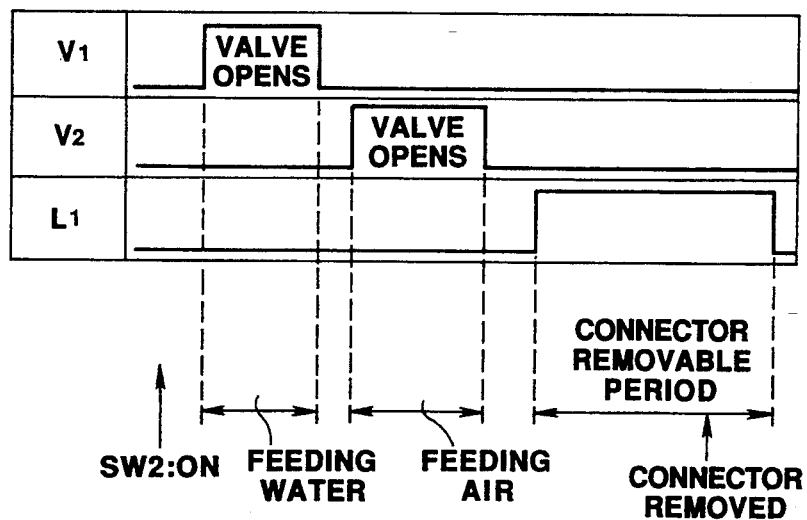

It is programmed, for example, that, when the releasing switch 8a is pushed, as shown in FIG. 8, the controlling circuit 46 will operate the first electromagnetic valve 27, second electromagnetic valve 23 and locking mechanism in the order mentioned. After water and air are fed within a predetermined time, the lock will be released and the connector 15 of the endoscope 11 will be removable. It shall be explained in the order in the following.

When the releasing switch 8a is pushed, first of all, the controlling circuit 46 will give an instruction, the second electromagnetic valve 23 will be opened and air will be fed from the pump 18 through the air feeding pipe 33, air and water feeding pipe 35 and nozzle 36 of the endoscope 11. At this time the first electromagnetic valve 27 will be closed. Then, the first electromagnetic valve 27 will be opened and water will be fed through the water feeding pipe 34, air and water feeding pipe 35 and nozzle 36. At this time, the second electromagnetic valve 23 will be closed.

After the predetermined time for feeding air and water ends, the pipeline controlling apparatus 10 will give a lock releasing instruction to the locking mechanism 61 from the controlling circuit 46 and the solenoid 64 of the locking mechanism 61 will operate to pull up the vertically moving pin 65. Therefore, the tip part 65a of the vertically moving pin 65 will not contact the stopper pin 15a of the connector 15 and the endoscope 11 will be removable from the pipeline controlling apparatus 10. The period while this connector 15 is removable will continue for a fixed time. After this fixed time elapses, the solenoid 64 will be again inoperative and the vertically moving pin 65 will return below. In this state, the energizing spring 66 will bias the vertically moving pin 65 to the projecting part 63a of the side hole 63.

When the connector 15 of the endoscope 11 is fitted to the pipeline controlling apparatus 10, the stopper pin 15a of the connector 15 will contact the slope 65b of the vertically moving pin 65 and will push up the vertically moving pin 65. When the connector 15 is fitted, the vertically moving pin 65 will be biased to the projecting part 63a of the side hole 63 by the energizing spring 66, the stopper pin 15a of the connector 15 will contact the vertically moving pin 65 at the front end 65a and will lock the endoscope 11 so as not to be pulled out.

In this embodiment, when the releasing switch 8a is pushed in order to unlock the locking mechanism 61, air and water will be first fed and therefore, even if the respective pipelines and nozzle 36 are clogged with dirt such dirt will be discharged out. After air and water are fed, the locking mechanism will be unlocked and therefore, even if the endoscope 11 is pulled out of the pipeline controlling apparatus 10 and is left alone, no dirt will coagulate, air and water will be able to be kept always ready to be fed and buildup of coagulated dirt will be prevented.

By the way, in this embodiment, the locking mechanism 61 is locked/unlocked by the vertical movement of the vertically moving pin 65 but, instead of the vertically moving pin 65, for example, a disk provided with an incision may be rotated to operate the same without being limited to the illustrated examples.

Figure 9:
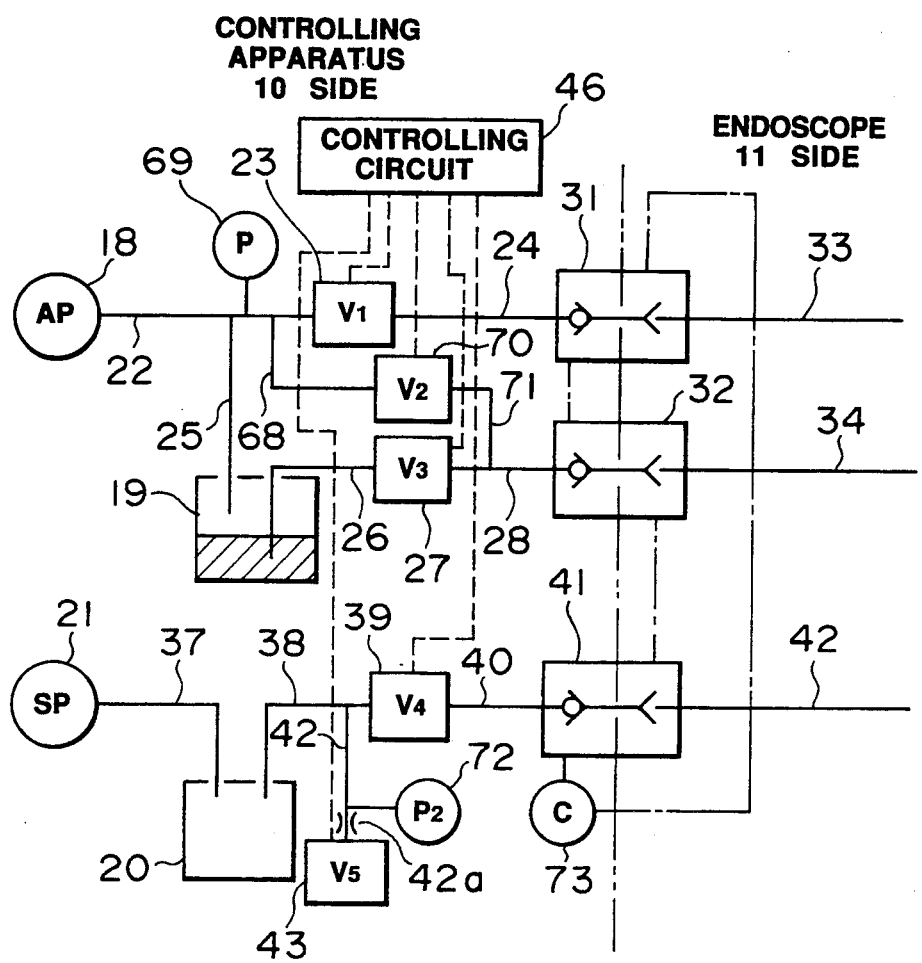
Figure 10:
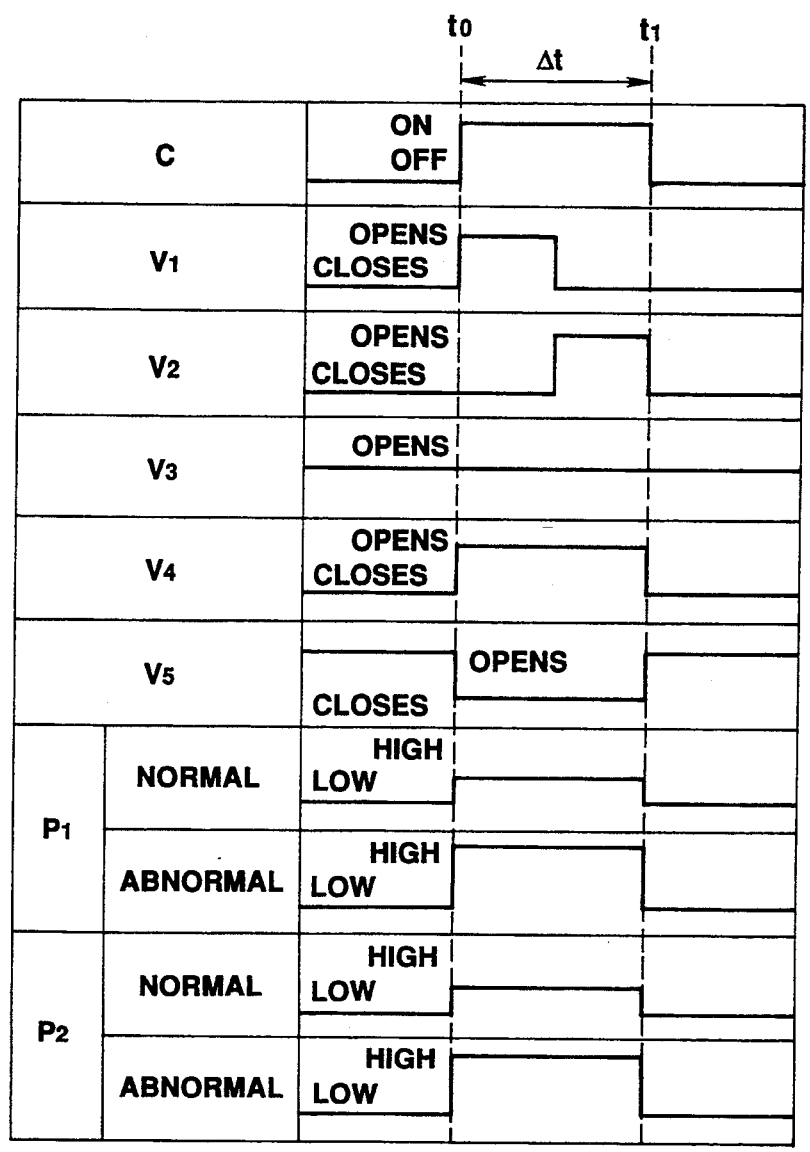

FIG. 9 is a pipeline diagram for sensing air and water feeding pipelines as clogged with dirt or the like. FIG. 10 is a timing chart showing operation timings of respective valves and pressure sensors.

The endoscope apparatus shown in FIG. 9 is provided with an endoscope 11 and a controlling apparatus 10. The controlling apparatus 10 is internally provided with an air feeding pump 18, suction pump 21, water feeding tank 19 and suction bottle 20. A first air feeding pipeline 22 is connected to the air feeding pump 18 and is provided with a first electromagnetic valve (V1) 23 to which is connected a second air feeding pipeline 24. A water feeding pressurized pipeline 25 is branched and connected in the course of the above-mentioned first air feeding pipeline 22 and is connected to communicate with the space above the stored water surface within the above-mentioned water feeding tank 19. A first water feeding pipeline 26 with the sucking port dipped in the stored water is connected to the above-mentioned water feeding tank 19 and a second water feeding pipeline 28 fitted with a third electromagnetic valve (V3) 27 is connected to this first water feeding pipeline 26. Further, a first water removing pipeline 68 is branched and connected midway between the above-mentioned water feeding pressurized pipeline 25 and first electromagnetic valve 23. A first pressure sensor 69 is provided between the branching point of the water feeding pressurized pipeline 25 and a first water removing pipeline 68 which connects a second water removing pipeline 71 fitted with a second electromagnetic valve (V2) 70. The second water removing pipeline 71 is connected in the course of the above-mentioned second water feeding pipeline 28.

On the other hand, a first sucking pipeline 37 is connected to the above-mentioned suction pump 21 and communicates with the space within the above-mentioned suction bottle 20. A second sucking pipeline 38 communicates with the space within the suction bottle 20 and a third sucking pipeline 40 fitted with a fourth electromagnetic valve 39 is connected to this second sucking pipeline 38. A venting pipeline 42 is branched and connected in the course of the above-mentioned second sucking pipeline 38, communicates with the atmosphere through a fifth electromagnetic valve 43 and is provided with an orifice 42a so that, even at the time of venting, a negative pressure may be kept from the suction pump 20 to the second sucking pipeline 38. A second pressure sensor 72 is provided between the orifice 42a and the branching point of the venting pipeline 42.

The above-mentioned second air feeding pipeline 24, second water feeding pipeline 28 and third sucking pipeline 40 are fitted at the respective ends with respective joints 31, 32 and 41 so as to be removably connected respectively to the air feeding pipeline 33, water feeding pipeline 34 and venting pipeline 42 on the endoscope 11 side. These air feeding pipeline 33 and water feeding pipeline 34 open through the air and water feeding pipe 35 and the venting pipeline 42 opens directly to the tip part of the endoscope 11.

The above-mentioned first to fifth electromagnetic valves 23, 70, 27, 39 and 43 are electrically connected to a controlling circuit 46 so as to be controlled to open and close. On the other hand, this controlling circuit 46 is connected to an air and water feeding switch, not illustrated, provided in the operating section of the endoscope 11 and a switch, not illustrated, provided the sheath of the light source apparatus. The joints 31, 32 and 41 are connected in series to a sensing circuit 73 which senses the jointing of the joints 31, 32 and 41. By the way, the sensing circuit 73 may be provided on the endoscope 11 side.

In this formation, as shown in the timing chart in FIG. 10, when the power source of the pipeline controlling apparatus 10 is on, in case the connection is normal from the time point when the pipeline controlling apparatus 10 starts connecting the endoscope 11 to the controlling apparatus 10, that is, from the time t0 to the time t1 (during the time Δt) in the chart, the sensing circuit 73 will be on and will make it known by a lamp or buzzer that the connection is normal. During the time Δt from the time t0, the first to fifth electromagnetic valves 23, 70, 27, 39 and 43 will be respectively opened or closed by the controlling circuit 46. In such case, the first and second pressure sensors 69 and 72 will sense the variation of the internal pressure within the pipeline and, in case the internal pressure is above the set pressure, that is, abnormal, the abnormal state will be made known by buzzers or lamps provided in the first and second pressure sensors 69 and 72.

In the endoscope apparatus in FIG. 9, when the endoscope 11 is fitted to the pipeline controlling apparatus 10, it will be able to be sensed on the controlling apparatus 10 side or endoscope 11 side whether the fitting is normal or not and, when the fitting is normal, the internal pressure within the respective pipelines will be automatically sensed and the clogging of the pipeline will be able to be detected by the variation of the pressure. Therefore, before the endoscope inspection, it will be able to be inspected whether air and water will be able to be normally fed or sucked and it will be safe. By the way, the endoscope to be used may be not only an electronic endoscope but also an optical fiber endoscope.

Figure 11:
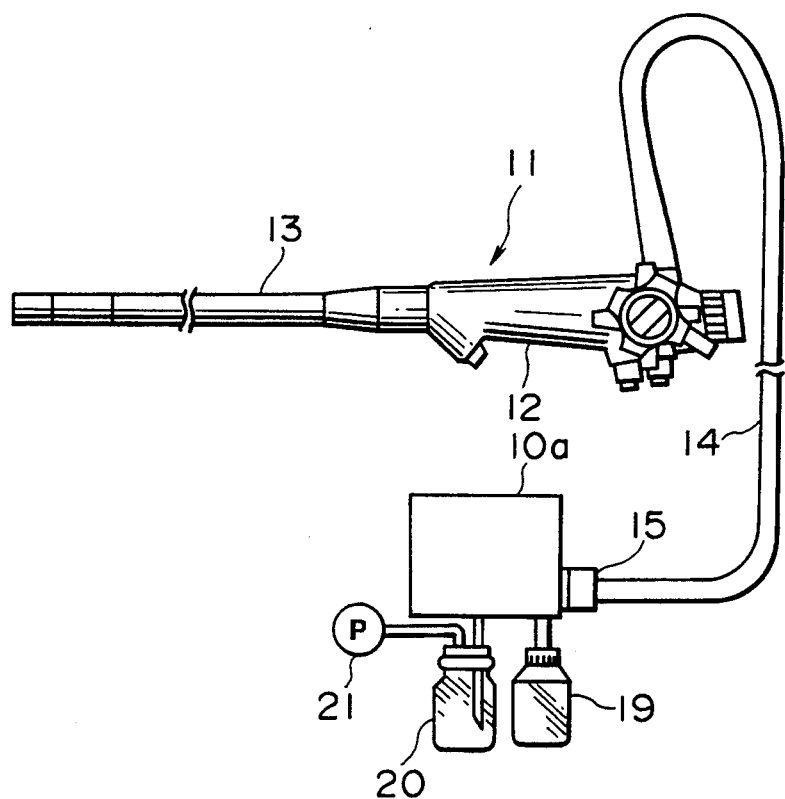

Now, the pipeline controlling apparatus 10a may be not only separate from the light source apparatus 16 shown in FIG. 3 but also of an integral type having the light source or the like built-in as shown in FIG. 11.

Figure 12:
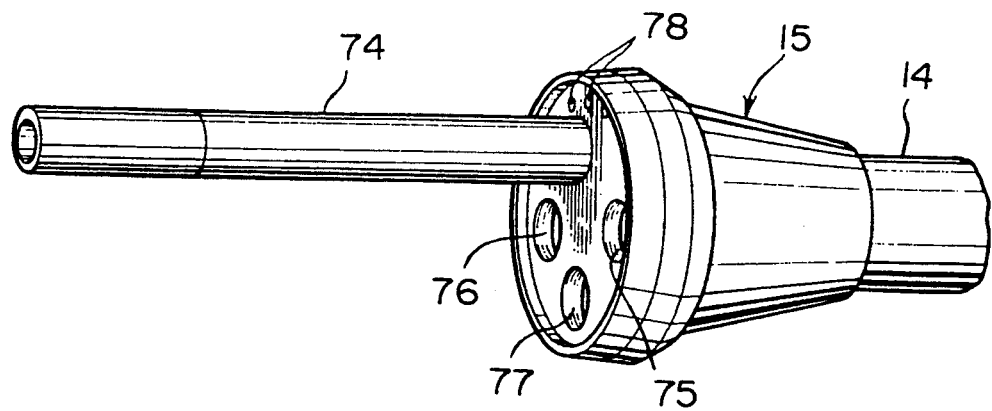

In the type in FIG. 11, as shown in FIG. 12, the connector 15 of the endoscope 11 is provided to project with a light guide connecting pipe 74 internally provided with a light guide fiber bundle transmitting the illuminating light from the light source apparatus 10a and has respective openings as of an air feeding pipe 75, water feeding pipe 76 and sucking pipe 89 communicating with respective pipelines of the pipeline controlling apparatus. Also, this connector 15 is provided with a plurality of relay receiving terminals 78 for transmitting imaging signals from the electronic endoscope 11. This connector 15 is used as combined with an adapter 79 shown in FIG. 13.

Figure 13:
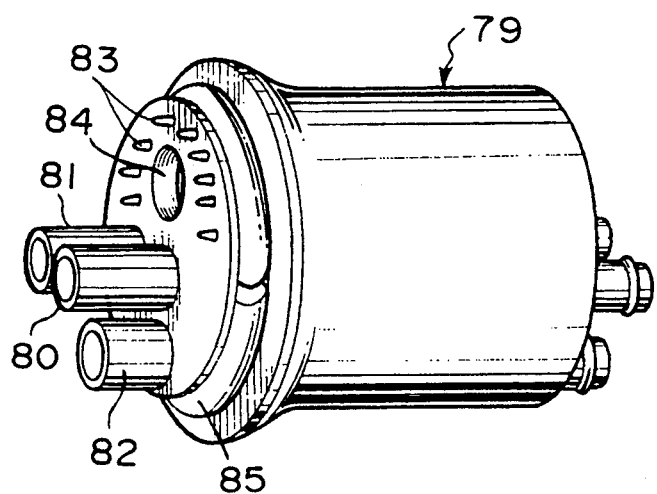

As shown in FIG. 13, the substantially cylindrical adapter 79 fits the controlling apparatus 10a which is also an integral type light source apparatus and the connector 15 of the endoscope 11 and connects the respective pipelines and signal wires as relayed. This adapter 79 is provided with an air feeding connecting pipe 80, water feeding connecting pipe 81 and sucking connecting pipe 82 in the positions opposed to the respective openings of the air feeding pipe 75, water feeding pipe 76 and sucking pipe 77 provided in the connector 15 of the endoscope 11 and in the axial direction and is also provided at both ends respectively with a plurality of relay contacts 83 which are connected with a plurality of signal wires not illustrated so as to electrically connect the endoscope 11 and light source apparatus 10a with each other. The adapter 79 is provided in the axial direction with a fitting hole 84 through which is inserted the light guide connecting pipe 74 of the connector 15 and is further fitted with a C ring 85 on the outer periphery near the apparatus side end to elevate the fittability to the controlling apparatus 10a. Therefore, when the adapter 79 is fitted to the connector 15 of the endoscope 11 and is further fitted to the controlling apparatus 10a, the respective pipelines of the endoscope 11 and controlling apparatus 10a will communicate with the air feeding connecting pipe 80, water feeding connecting pipe 81 and sucking connecting pipe 82.

Figure 14:
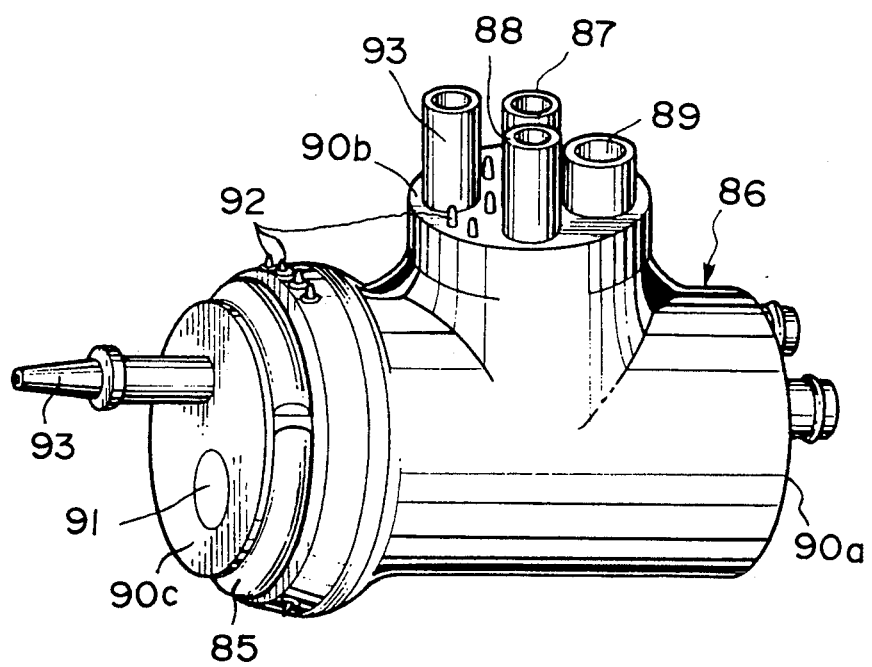
Figure 15:
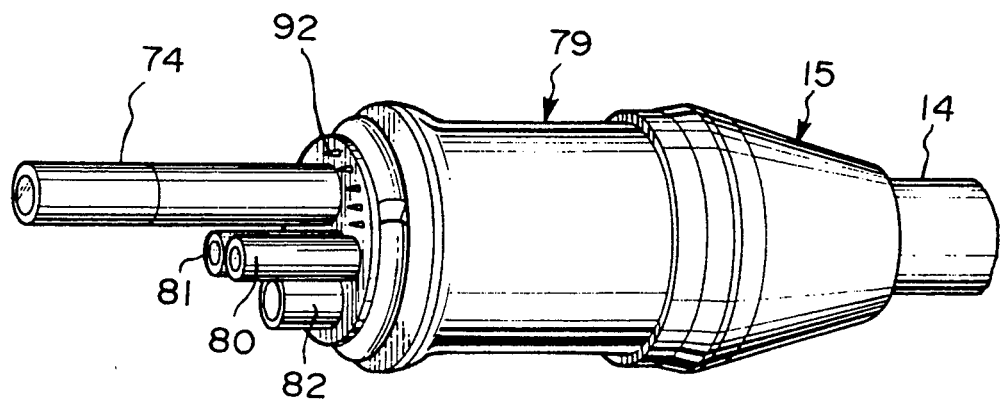
Figure 16:
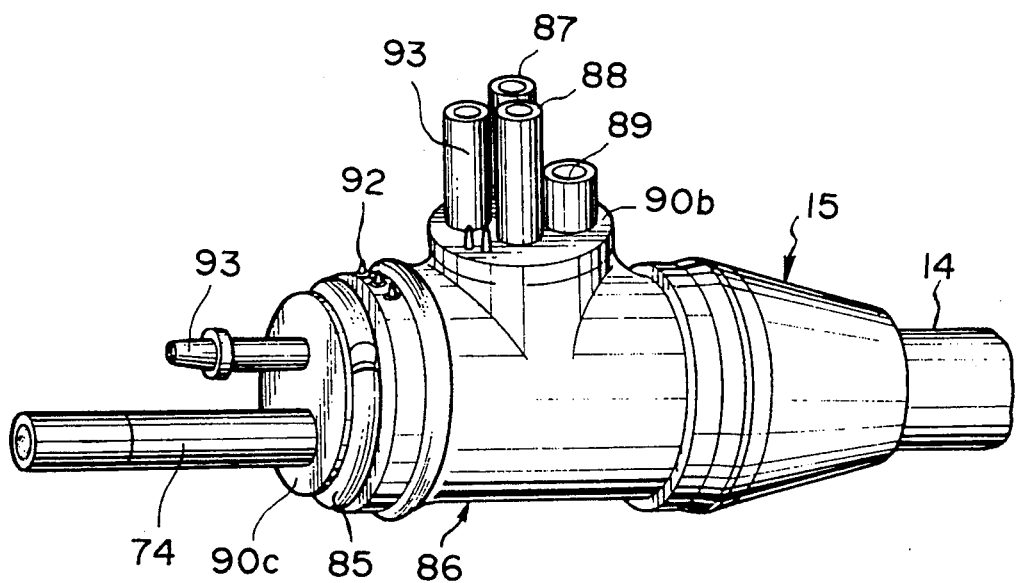

The substantially cylindrical adapter 86 shown in FIG. 14 fits the light source apparatus 16 and endoscope 11 shown in Fig. 3 and connects to the separate type pipeline controlling apparatus 10 through the above-mentioned connecting part 9 to relay and connect the respective pipelines and signal wires. On the endoscope end side 90a, this adapter 86 is provided with an air feeding connecting pipe 87, water feeding connecting pipe 88 and sucking pipe 89 to project in the positions opposed to the respective openings of the air feeding pipe, water feeding pipe and sucking pipe provided in the connector 15 of the endoscope 11, and the air feeding connecting pipe 87, water feeding connecting pipe 88 and sucking pipe 89 are provided to project on the pipeline controlling apparatus side end 90b provided in the course of the side of the adapter 86 and communicate with the respective pipelines of the above-mentioned connecting part 9. Also, the adapter 86 is provided in the axial direction with a fitting hole 91 through which is inserted the light guide connecting pipe of the connector 15. The adapter 86 is further provided at the respective ends with a plurality of relaying contacts 92 which are connected with a plurality of signal wires not illustrated so as to be electrically connected with the endoscope 11, light source apparatus 16 and pipeline controlling apparatus 10, and is further fitted with a C ring 85 on the light source apparatus side end 90c side outer periphery so as to elevate the fittability to the light source apparatus 16 and is provided with an air feeding pipeline 93 inserted between the light source apparatus side end 90c and the air and water feeding apparatus side end 90b and provided to project at both ends. When this adapter 86 is fitted to the connector 15 of the endoscope 11 and is further fitted to the pipeline controlling apparatus 10 through the connecting part 9, the respective pipelines of the endoscope 11 and pipeline controlling apparatus 10 will communicate with the air feeding connecting pipe 87, water feeding connecting pipe 88 and sucking connecting pipe 89. By the way, FIGS. 15 and 16 show the adapters 79 and 86 as, respectively, fitted to the connector 15 of the endoscope 11. By these adapters 79 and 86, the endoscope 11 can be connected to either of the integral type and separate type pipeline controlling apparatus, two kinds of endoscopes need not be purchased and it is economically advantageous.

FIGS. 17 to 23 show the third embodiment.

Figure 17:
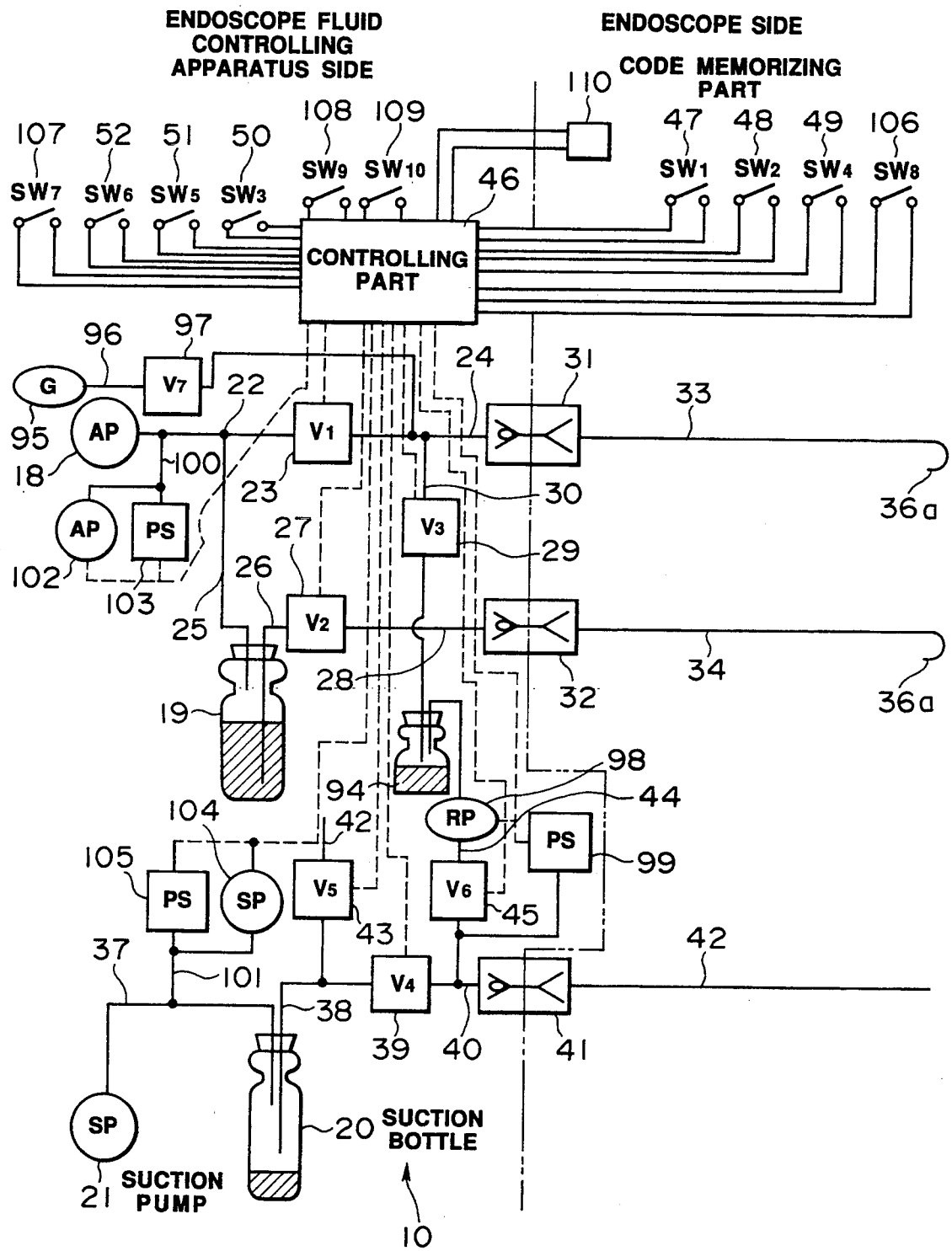

As shown in the pipeline diagram in FIG. 17, the pipeline controlling apparatus 10 is internally provided with an air feeding pump 18 which is a pressurized air feeding source and is provided outside with a water feeding tank 19 communicating through a pipeline. A first air feeding pipeline 22 is connected to this air feeding pump 18 and is provided with a first electromagnetic valve (V1) 23 to which is connected a second air feeding pipe 24. An air feeding pressurized pipeline 25 is branched and connected in the course of the above-mentioned first air feeding pipeline 22 and is connected to communicate with the space above the stored water surface within the above-mentioned water feeding tank 19 to which is connected a first water feeding pipeline 26 with the sucking port dipped in the stored water. A second water feeding pipeline 28 is connected to this first water feeding pipeline 26 through a second electromagnetic valve (V2) 27.

A refluxing air feeding pipeline 30 is branched and connected to the above-mentioned second air feeding pipeline 24 and is connected to a refluxing suction bottle 94 through a third electromagnetic valve (V3) 29. The above-mentioned second air feeding pipeline 24 and second water feeding pipeline 28 are fitted at the ends with respective joints 31 and 32 so as to be removably connected, respectively, to an air feeding pipeline 33 and water feeding pipeline 34 on the endoscope side. The air feeding pipeline 33 and water feeding pipeline 34 communicate respectively with nozzles 36a opening toward an observing window, not illustrated, of the endoscope tip part. By the way, as shown in the drawing, an air feeding pump is provided in the light source apparatus and the air feeding pipeline 33 and water feeding pipeline 34 are joined with each other on the tip side.

A first gas pipeline 96 is connected to a gas tank 95 storing a nonflammable gas and is connected to the second air feeding pipeline 24 through a seventh electromagnetic valve (V7) 97. On the other hand, a first sucking pipeline 37 is connected to a suction pump 21 and is connected to a suction bottle 20 to which is connected a second sucking pipeline 38. A third sucking pipeline 40 is connected to the second sucking pipeline 38 through a fourth electromagnetic valve (V4) 39 and is fitted at the end with a joint 41 so as to be removably connected with a sucking pipeline 42 on the endoscope side. A venting pipeline 42 fitted with a fifth electromagnetic valve (V5) 43 is branched in the course of the second sucking pipeline 38.

A refluxing sucking pipeline 44 is branched in the course of the third sucking pipeline 40 and is fitted with a sixth electromagnetic valve (V6) 45 and refluxing roller pump (mentioned as a refluxing pump hereinafter) 98. The above-mentioned refluxing suction bottle 94 is connected to this pump 98 on the delivery side and a pressure sensor 99 is connected through the above-mentioned sixth electromagnetic valve (V6) 45 to the pump 98 on the suction side.

Pressure adjusting pipelines 100 and 101 are branched and connected respectively to the above-mentioned first air feeding pipeline 22 and first sucking pipeline 37. An auxiliary air feeding pump 102 and a pressure sensor 103 are connected to the pressure adjusting pipeline 100. An auxiliary suction pump 104 and a pressure sensor 105 are connected to the pressure adjusting pipeline 101.

The above-mentioned refluxing pump 98, auxiliary air feeding pump 102, auxiliary suction pump 104 and pressure sensors 99, 103 and 105 are, respectively, electrically connected to a controlling part 46 to which are electrically connected the above-mentioned first to seventh electromagnetic valves 23, 27, 29, 39, 43, 45 and 97 to be controlled to open and close. Further, to this controlling circuit 46 are connected switches (SW1) 47, (SW2) 48, (SW4) 49 and (SW8) 106 of the endoscope 11 and switches (SW3) 50, (SW5) 51, (SW6) 52, (SW7) 107, (SW9) 108 and (SW10) 109 provided in the sheath of the controlling apparatus 10. Further, to the controlling part 46 is connected a code memorizing part 110 as a distinguished means provided in the endoscope 11.

Figure 20:
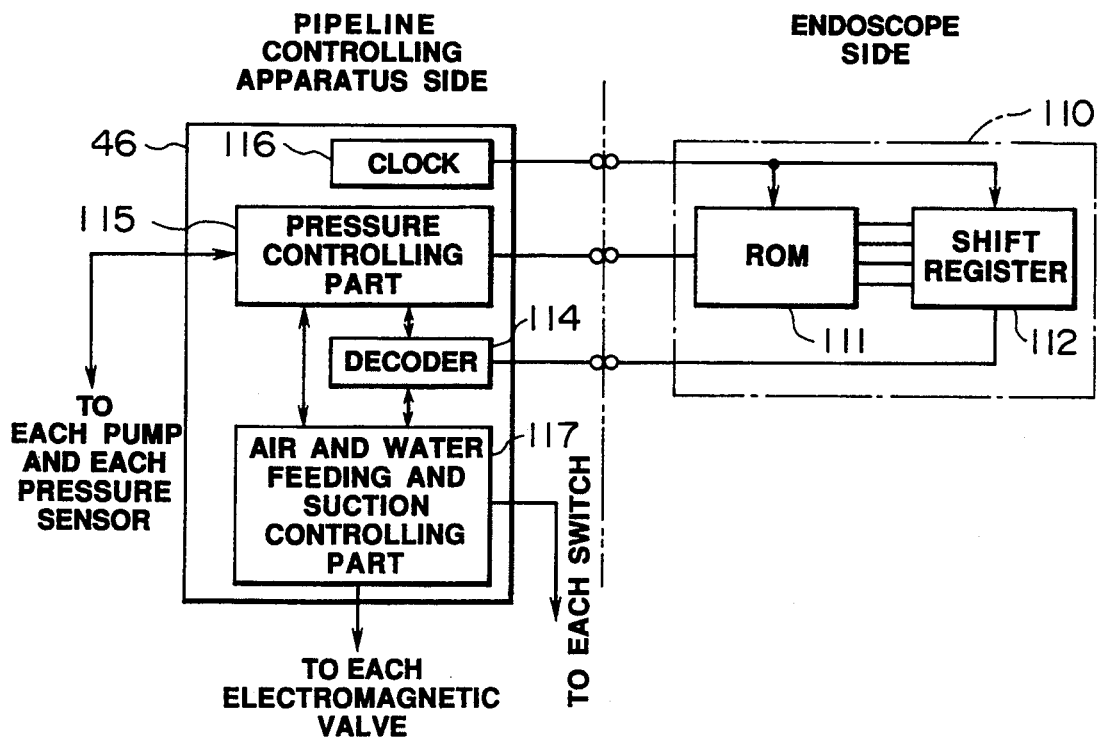

As shown in FIG. 20, the above-mentioned code memorizing part 110 is formed from a ROM memorizing the kind of code of the endoscope and a shift register 112 converting to serial signals the parallel data output by this ROM 111. On the other hand, the controlling part 46 of the controlling apparatus 10 is formed of a decoder 114 as a sensing means distinguishing the serial data transmitted from the shift register 112 of the endoscope 11, a pressure controlling part 115 as a pressure switching means monitoring the pressure values shown by the above-mentioned respective pressure sensors, 99, 103 and 105 and switching and adjusting the above-mentioned respective pumps as pressure adjusting means to be under the preset pressure in response to the data (of the kinds) read by the decoder 114, a clock 116 controlling the reading timing of the ROM 111 and shift register 113 of the endoscope 11 and an air and water feeding and sucking controlling part 117 controlling feeding, sucking and refluxing air and water by opening and closing the respective electromagnetic valves in response to the setting of the above-mentioned respective switches.

In this formation, when the connector of the endoscope 11 is inserted into the pipeline controlling apparatus 10, as an initial adjustment, the data memorized in advance in the ROM 111 will be converted to serial data through the shift register 112 and will be input into the decoder 114. Then, the decoder 114 will read the kind of the fitted endoscope 11 from the transmitted serial data and the pressure controlling part 115 will adjust the auxiliary air feeding pump 102 and auxiliary suction pump 104 to make initially set air feeding pressures of the respective parts and initially set sucking pressures of the respective parts (shown in FIG. 18) adapted to the applying positions, pipeline inside diameters and pipeline lengths so that the inspection may be possible. In the same manner, the pressure controlling part 115 will be able to set the refluxing pump 98 under the initially set refluxing pressure adapted to the kind of the endoscope. That is to say, in this embodiment, the optimum initially set pressure can be made in response to the kind of the endoscope and air and water can be fed and sucked safely without taking useless time.

The control of feeding air, feeding water, sucking air, sucking while refluxing, feeding water while refluxing and feeding a gas while refluxing shall be explained in the order mentioned with reference to the timing chart in the following.

Figure 18:
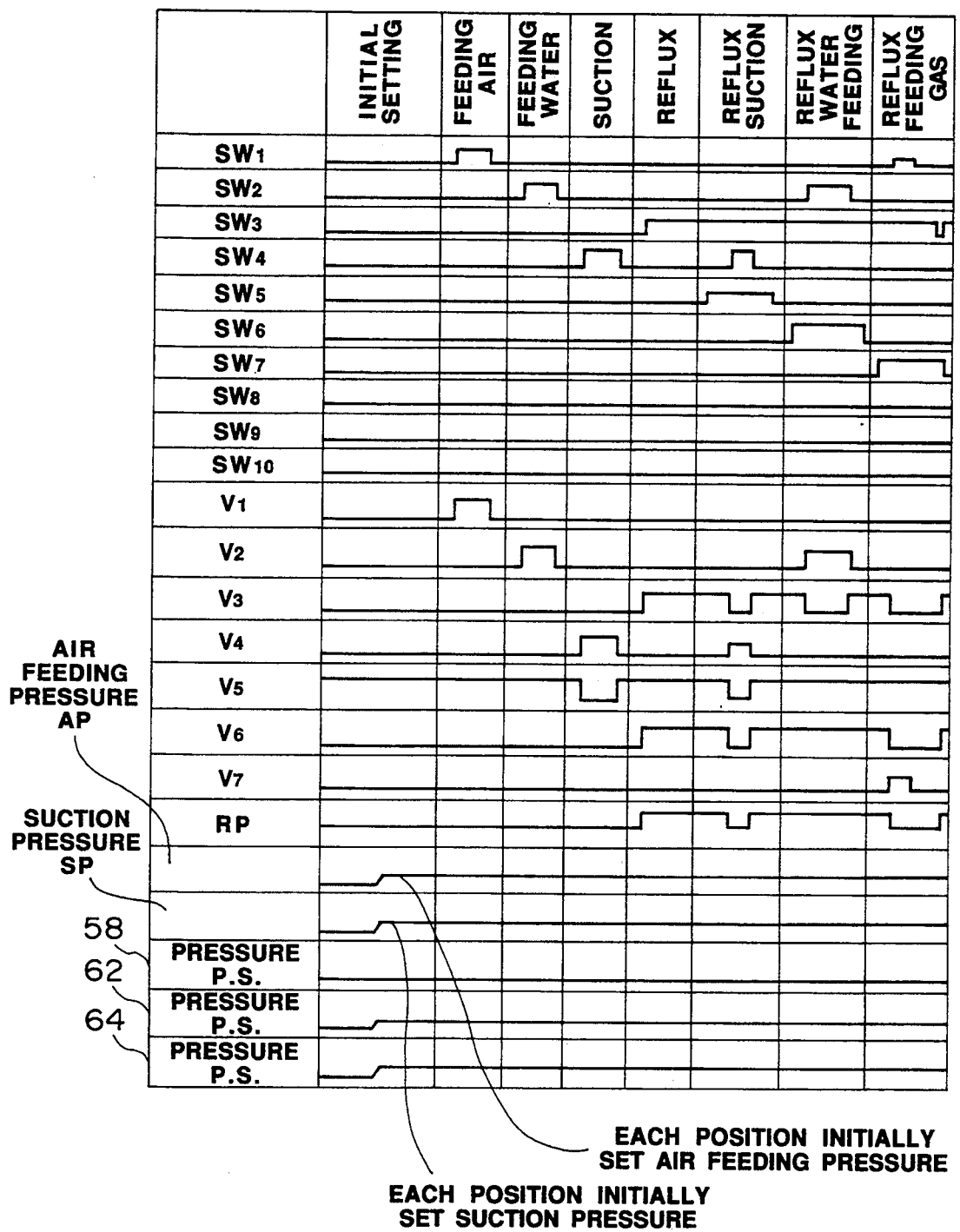

As shown in the timing chart in FIG. 18, air and water are fed during the ordinary endoscope inspection by switching on/off the switches 47 and 48 provided in the operating section. That is to say, in the case of feeding air, when the switch (SW1) 47 is switched on, the first electromagnetic valve 23 will be opened by the controlling part 46 and air will be fed through the air feeding pipeline 33. On the other hand, in feeding water, when switch (SW2) 48 is switched on, the controlling part 46 will open the second electromagnetic valve 27 in the same manner and washing water will be fed to the water feeding pipeline 34.

Then, sucking will be made by switching on/off the switch (SW4) 49 provided in the operating section. That is to say, when the switch (SW4) 49 is switched on, by the controlling part 46, only the fifth electromagnetic valve 43 will be opened, the switch 49 will be operatively connected from the ordinary standing by, the fifth electromagnetic valve 43 will be closed and the fourth electromagnetic valve 39 will be opened to suck.

Further, refluxing will be made as follows. When the switch (SW3) 50 switching the operation and stop of the reflux is switched on, the sixth electromagnetic valve 45 and third electromagnetic valve 20 will be opened, the refluxing pump 98 will operate, the fluid or the like within the body cavity will be sucked through the sucking pipeline 42, third sucking pipeline 40 and refluxing sucking pipeline 44, the fluid having flowed into the refluxing suction bottle 94 will be separated into such fluid as a mucous liquid and air and only air (of the same amount as the sucked amount) will be fed from the nozzle 36a through the refluxing air feeding pipeline 30, second air feeding pipeline 24 and air feeding pipeline 33. In stopping the reflux, when the switch 50 is switched off, the refluxing pump 98 will stop and the third electromagnetic valve 29 and sixth electromagnetic valve 45 will be closed to stop the reflux.

Sucking and feeding water and air while refluxing shall be explained in the following.

First of all, in the case of sucking while refluxing, when the switch (SW5) 51 is switched on, the control not stopping the reflux when the switch 49 is on (while sucking) will be switched over to the control stopping the reflux. While the switch (SW5) 51 is on, further the refluxing operation switching switch (SW3) 50 is on, the third and sixth electromagnetic valves 29 and 45 are opened and the refluxing pump 98 is operating, when the sucking switch (SW4) 49 is switched on, the fifth electromagnetic valve 43 will be closed and the fourth electromagnetic valve 39 will be closed to start sucking. At the same time, the third and sixth electromagnetic valves 29 and 45 will close and the refluxing pump 98 will stop. When the switch (SW4) 49 is switched off, the fifth electromagnetic valve 43 will be opened, the fourth electromagnetic valve 39 will be closed to stop the suction, the third and sixth electromagnetic valves 29 and 45 will be opened and the refluxing pump 98 will operate and will return to the refluxing operation.

Feeding water while refluxing shall be explained in the following.

As in this embodiment, in the endoscope of a type in which the air feeding nozzle 36a and water feeding nozzle 36b are separately provided, if water is fed while air is being refluxed and fed, as air is being always jetted out of the air feeding nozzle 36a, the fed water will be blown away and the lens surface of an observing window, not illustrated, will inconveniently go unwashed. Therefore, in this apparatus, there is taken a means of closing the air sucking pipeline 30 only while feeding water to feed no air. In order to feed water during the reflux, while the switch (SW6) 52 for stopping refluxing feeding air while feeding water is on and the switch (SW3) 50 is on, that is to say, the third and sixth electromagnetic valve 29 and 45 are opened and the refluxing pump 98 is operating, if the switch (SW2) 48 is switched on, the second electromagnetic valve 27 will be opened to feed water. At the same time, the third electromagnetic valve 29 will be closed to stop refluxing feeding air. When the above-mentioned switch (SW2) 48 is switched off, the second electromagnetic valve 27 will be closed, the third electromagnetic valve 29 will be opened to stop feeding water and refluxing feeding air will be resumed. In this apparatus, as the operation is controlled, even if water is fed while refluxing, the observing window will be able to be positively washed.

The case of feeding gas while refluxing shall be explained in the following.

In this embodiment, in order to elevate the gas density within a short time, there is made a control whereby, when a gas is fed, the reflux will automatically stop. In order to feed the gas while refluxing, first of all, when the air feeding/gas feeding switching switch (SW7) 107 is switched on and, in this state, the switch (SW1) 47 is switched on, the seventh electromagnetic valve 97 will open, at the same time as the gas is fed, the third and sixth electromagnetic valves 29 and 45 will close, the refluxing pump 98 will stop and the gas will be fed. When the switch (SW1) 47 is switched off, only the seventh electromagnetic valve 97 will be closed to stop feeding the gas and will remain closed. In order to make the reflux again, when the refluxing switch (SW3) 50 is again switched on, the reflux will be resumed. Even if the gas is fed, the gas will not be rarefied by the reflux and will be safe.

Figure 19:
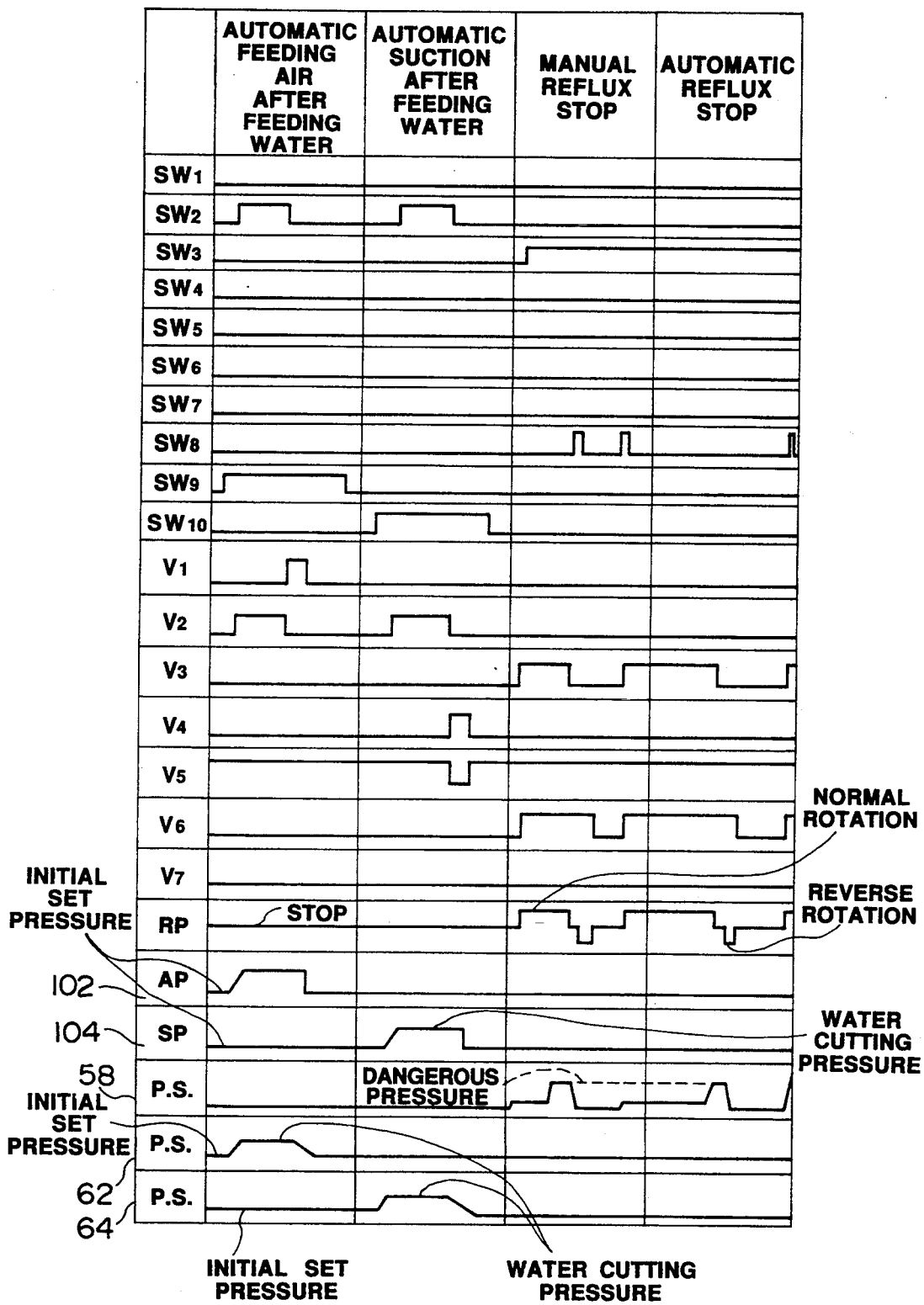

Stopping the reflux, feeding air after feeding water and the sucking operation shall be explained in the following with reference to the time chart in FIG. 19.

First of all, manually stopping the reflux in order to avoid danger in case a mucous membrane is adsorbed in the reflux shall be explained. In case a mucous membrane adsorption is generated while refluxing (while SW3 is on), when the switch (SW8) 106 provided in the operating section is pushed, the refluxing pump 98 will momentarily stop, the third electromagnetic valve 29 will be closed and the back flow from the nozzle 36 will be prevented, the refluxing pump 98 will be reversely rotated for several seconds, air within the refluxing suction bottle 94 will be fed into the sucking pipeline 42, the adsorbed substance will be removed and then the refluxing pump 98 will stop. In the case of resuming the reflux, the switch (SW8) 106 will be switched on again. In this embodiment, the switch (SW8) 106 for stopping the reflux is provided in the operating section, and therefore can be immediately safely pushed.

Also, in this embodiment, in case the endoscope user fails to notice the adsorption generation, such operation as in the following will be automatically made. Before starting the inspection, a decoder 114 will read the kind of the fitted endoscope from the serial data transmitted from a cord memorizing part 110. The decoder 114 has judged the pipeline diameter and pipeline length of the endoscope and the applying position of the inspected object and has read out and memorized the safe suction pressure preset for each endoscope and applying position. During the inspection, when the mucous membrane is adsorbed, the sucking pipeline internal pressure rises and the pressure of the refluxing pressure sensor 99 becomes higher than the preset suction pressure, the controlling part 46 will automatically control the same as when the above-mentioned switch (SW8) 106 is switched on. Therefore, the refluxing pump 13 will reversely rotate, the adsorption will be able to be released and it will be safe. When the switch 106 is switched on, the reflux will be resumed.

The control for improving the evacuation of water droplets after feeding water shall be described in the following. First of all, automatic feeding air after feeding water shall be explained.

First, while the switch (SW9) 108 for switching automatic feeding air after feeding water and ordinary feeding water over to each other is switched on, when the switch 48 for feeding water is switched on, the second electromagnetic valve 27 will open and an auxiliary pump 102 will make the air feeding pressure best in the evacuation of water droplets. When the switch 48 is switched off, the second electromagnetic valve 27 will close, at the same time, the first electromagnetic valve 23 will open and will close after air is fed for a predetermined time (for example, of 0.1 to 1 second), an auxiliary air feeding pump 102 will also return to the initially set air feeding pressure and feeding air will end. Thereby, after feeding water, water cutting air will be able to be fed under a pressure higher than usual, the evacuation of water droplets will improve and, after automatically feeding air after feeding water, air will be able to be fed under a predetermined initially set pressure for the respective positions as ordinary feeding air and therefore it will be safe.

On the other hand, in the automatic suction after feeding water, when the switch (SW10) 109 for switching ordinary feeding water and automatic suction after feeding water over to each other is switched on and, in this state, further the switch (SW2) 48 for feeding water is switched on, the second electromagnetic valve 27 will open and will feed water and, at the same time, the auxiliary suction pump 104 will operate and will adjust the suction pressure to be a predetermined initially set pressure under which the water cuttability is best. When the switch (SW2) 48 is switched off, the second electromagnetic valve 27 and fifth electromagnetic valve 43 will close, the fourth electromagnetic valve 39 will open for a predetermined time (for example, of 0.1 to 1 second), a suction will be made, then the fourth electromagnetic valve 39 will close, the fifth electromagnetic valve 43 will open, the auxiliary suction pump 104 will return to the initially set suction pressure and the suction will end. Therefore, after feeding water, a suction to evacuate water droplets will be possible under a pressure higher than usual and, after automatic feeding air after feeding water, a suction under a predetermined initially set pressure which is an ordinary suction will be able to be made and therefore will be safe.

Figure 21:
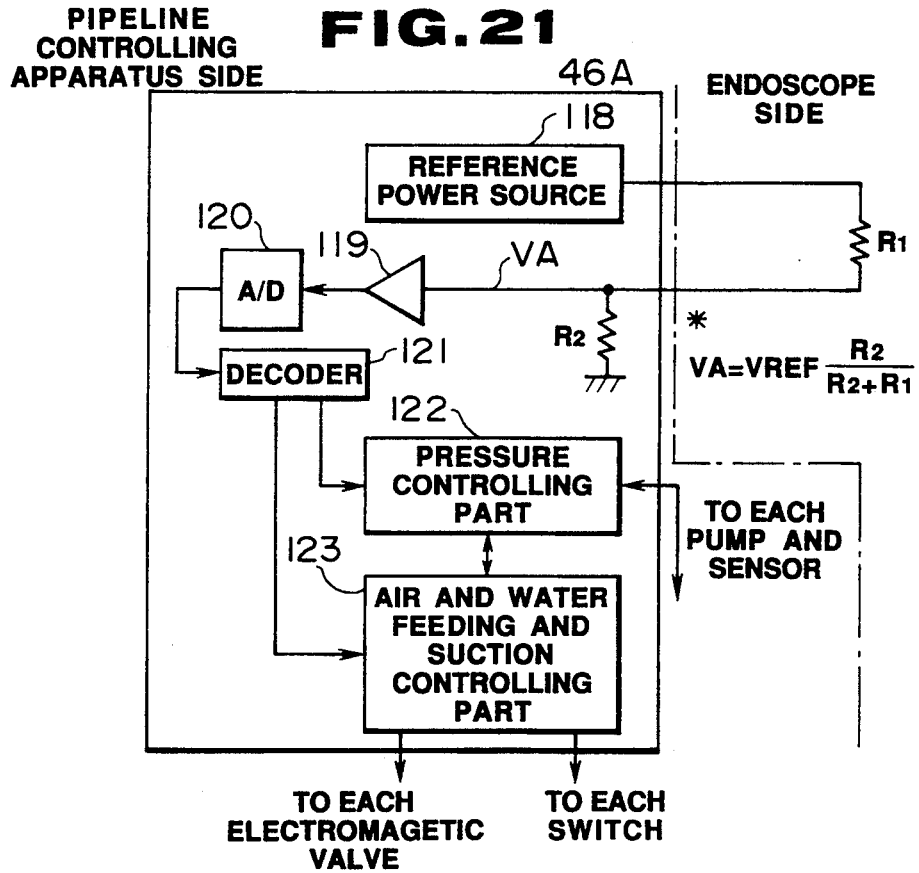

FIG. 21 is a schematic formation diagram relating to a modification of the third embodiment.

In this modification, the kind of the endoscope is discriminated by using a resistor incorporated in the endoscope as a distinguishing means instead of the code memorizing part.

The other same formations and operations as of the embodiment shall not be illustrated.

As shown in FIG. 21, the above-mentioned register R1 is provided on the endoscope side and, on the other hand, the endoscope pipeline controlling apparatus has a controlling part 46A. The resistor R1 is different for each endoscope and indicates information regarding the kind of endoscope. This operating part 46A comprises a reference power source 118 applying a reference voltage V ref to the resistor R1 of the endoscope, a voltage dividing resistor R2 dividing the reference voltage V ref into a voltage VA together with the resistor R1 of the endoscope, a buffer 119 inputting the divided voltage VA obtained by dividing the reference voltage V ref, an analog/digital (A/D) converter 120 analog/digital-converting the signal output by the buffer 119 and a decoder 121 sensing the digital signal output by the A/D converter, sensing the kind of the endoscope and outputting various kinds of set signals. This controlling apparatus comprises a pressure controlling part 122 as of a pressure switching output setting the pressure of each above-mentioned pump at a predetermined value in response to the set signal output by the above-mentioned decoder 121 and monitoring the pressure signals of respective pressure sensors and an air and water feeding and sucking controlling part 123 opening and closing respective electromagnetic valves in response to the switching on/off of the above-mentioned respective switches and controlling feeding, sucking and refluxing air and water.

In this formation, the decoder 121 reads the digital signals, senses the kind of the endoscope and feeds the result into the pressure controlling part 122 and the pressure controlling part 122 adjusts the pressures of the above-mentioned respective pumps so as to be water and air feeding, sucking and refluxing pressures optimum to the pipeline inside diameters and pipeline lengths of the endoscope and the applied positions of the inspected object.

The other formations, operations and effects are the same as in the embodiment and shall not be explained here.

FIGS. 22 and 23 further show another modification.

This modification has bar codes distinguishing means instead of the code memorizing part of the above-mentioned embodiment. The same formations and operations of the above-mentioned embodiment shall not be illustrated here.

As shown in FIG. 23, the endoscope connector 15A is provided at the end to project in the axial direction with a light guide connecting pipe 74 to be inserted through the light guide. Bar codes 124 which indicate information regarding the kind of the endoscope are formed on the outer periphery of the light guide connecting pipe 74.

On the other hand, the endoscope pipeline controlling apparatus has a controlling part 6B which comprises an optical mark reader (OMR) 125 converting the bar codes 124 of the endoscope to an electric signal to be output, a signal reading part 126 sensing the kind of the endoscope from the signal output by this OMR 125 and outputting respective set signals, a pressure controlling part 127 setting the pressures of the above-mentioned respective pumps at predetermined values in response to setting signals output by the signal reading part 126 and monitoring the pressure signals of the respective pressure sensors and an air and water feeding and sucking controlling part 128 opening and closing the respective electromagnetic valves in response to switching on/off the above-mentioned respective switches and controlling feeding, sucking and refluxing air and water.

In this formation, the signal reading part 126 reads digital signals, senses the kind of the endoscope and feeds the result into the pressure controlling part 127 which adjusts the pressures of the above-mentioned respective pumps so as to be water and air feeding, sucking and refluxing pressures optimum to the pipeline inside diameters and pipeline lengths of the endoscope and the applied positions of the inspected object. The other formations, operations and effects are the same as in the previous embodiment and shall not be explained here.

By the way, in the above-mentioned third embodiment and modification, the desired pressure adapted to the endoscope is set by using the air feeding auxiliary pump 102 and the sucking auxiliary pump 104 but, for example, the opening of the electromagnetic valve may be controlled to obtain a desired pressure lower than the pressure of the air feeding pump 18 and suction pump 21 set to be rather high. In such case, the air feeding auxiliary pump and sucking auxiliary pump will be unnecessary.

It is needless to say that this embodiment can be used for a fiber endoscope. By the way, in the fiber endoscope, the kind sensing means may be used not only for adjusting the air feeding pressure, water feeding pressure and suction pressure but also for automatically correcting the exposure of an externally fitted camera corresponding, for example, to the maskability of the endoscope.

FIGS. 24 to 35 show the fourth embodiment.

Figure 24:
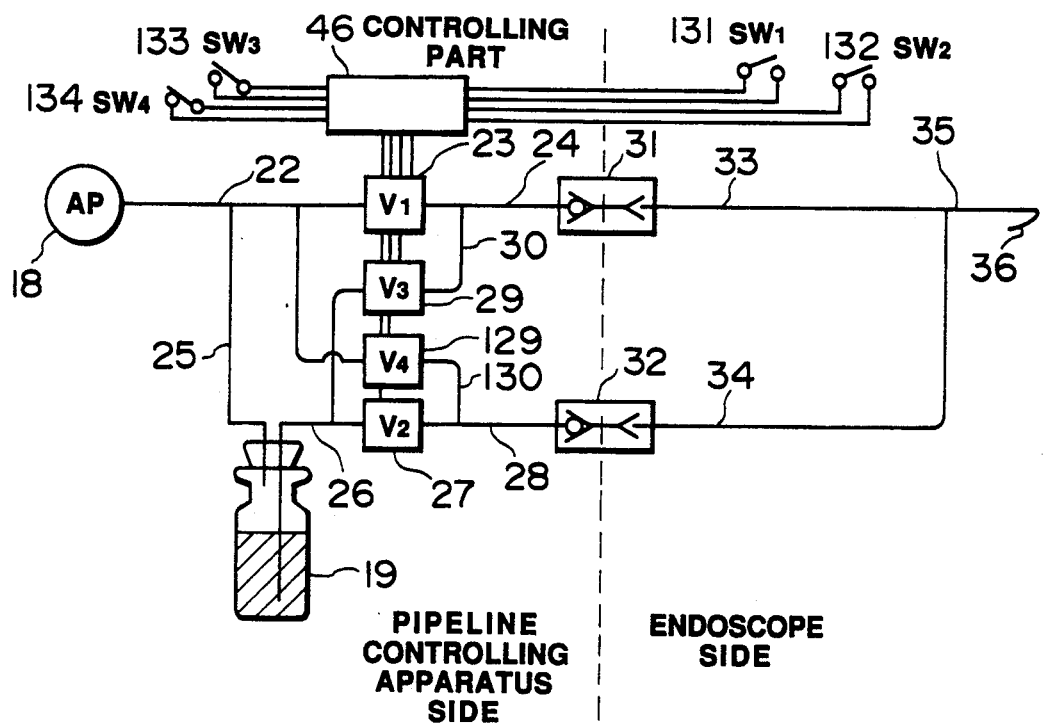
FIGS. 24 to 35 relate to the fourth embodiment.

In the pipeline diagram shown in FIG. 24, a first air feeding pipeline 22 is connected to an air feeding pump 18 and is provided with a first electromagnetic valve (V1) 23 to which is connected a second pipeline 24. A water feeding pressurized pipeline 25 is branched and connected in the course of the above-mentioned first air feeding pipeline 22 and is connected to communicate with the space above the stored water surface within a water feeding tank 19. A first water feeding pipeline is connected to the above-mentioned water feeding tank 19 with the sucking port dipped in the stored water. A second water feeding pipeline 28 is connected through a second electromagnetic valve (V2) 27 to this first pipeline 26. The above-mentioned second air feeding pipeline 24 and the first water feeding pipeline 26 are connected with each other through an air feeding pipeline washing pipeline 30 fitted with a third electromagnetic valve (V3) 29 in the course. On the other hand, the first air feeding pipeline 22 and second water feeding pipeline 28 are connected with each other through a water feeding pipeline water removing pipeline 130 fitted with a fourth electromagnetic valve (V4) 129 in the course. The above-mentioned second air feeding pipeline 24 and second water feeding pipeline 28 are fitted at the ends with respective quick joints 31 and 32 so as to be removably connected by one touch, respectively, to an air feeding pipeline 33 and water feeding pipeline 34 on the endoscope side. These air feeding pipeline 33 and water feeding pipeline 34 join with each other on the tip side of the endoscope insertable section 13 to form an air and water feeding pipeline 35 which communicates with a nozzle 36 opening toward an observing window in the endoscope tip part. Further the above-mentioned first electromagnetic valve 23, second electromagnetic valve 27, third electromagnetic valve 29 and fourth electromagnetic valve 129 are, respectively, electrically connected to a controlling part 46. On the other hand, to this controlling part 46 are connected switches (SW1) 131 and (SW2) 132 provided in the operating section of the endoscope 11 and switches (SW3) 133 and (SW4) 134 provided in the sheath of the pipeline controlling apparatus 10.

Figure 25:
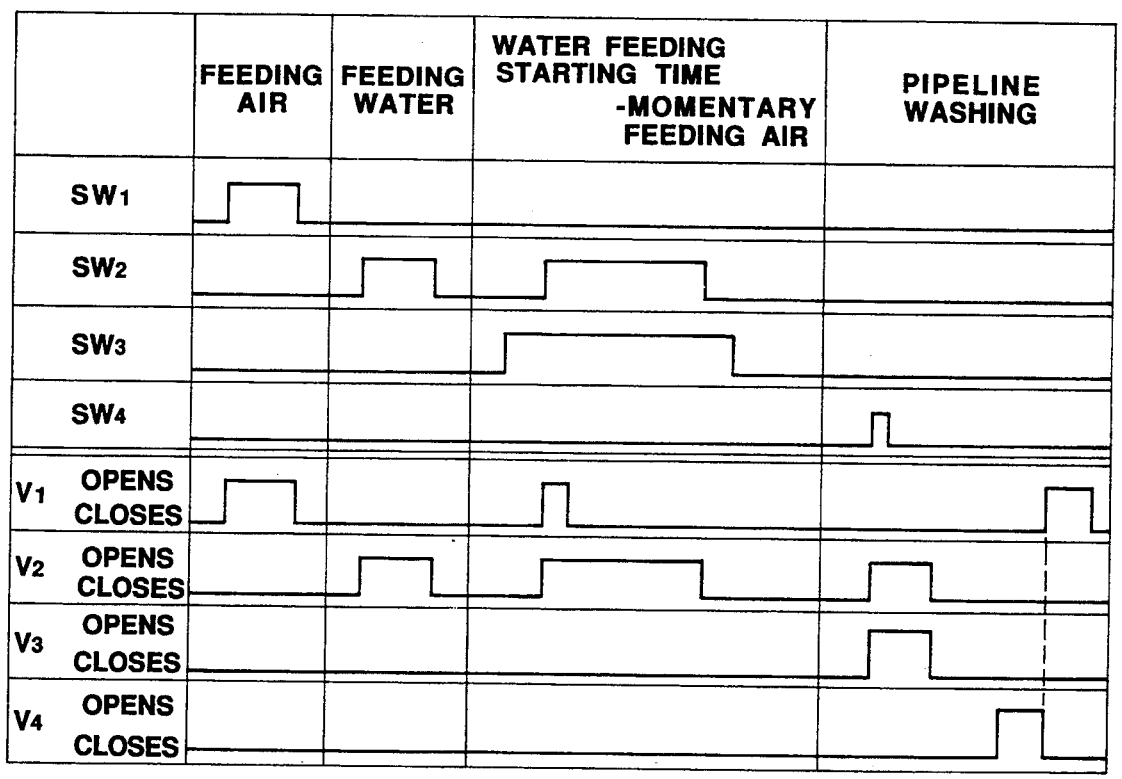

In such formation, as shown in the time chart in FIG. 25, during the usual endoscope inspection, air and water are fed by switching on/off the switches 131 and 132 provided in the operating section 12. That is to say, in the case of feeding air, when the switch 131 is switched on, the first electromagnetic valve 23 will be opened by the controlling part 46 and air will be fed through the air feeding pipeline 33. On the other hand, in feeding water, when the switch 132 is switched on, in the same manner, the controlling part 46 will open the second electromagnetic valve 27 and washing water will be fed to the water feeding pipeline 35.

In this embodiment, it is controlled to momentarily feed air simultaneously with starting the above-mentioned feeding water. In this control, first the switch 133 is switched on. This switch 133 switches ordinary feeding water and momentarily feeding air simultaneously with starting feeding water over to each other. Therefore, while this switch 133 is on, if the water feeding switch 132 is switched on, the controlling part will sense the signal, will open the second electromagnetic valve 27 and will simultaneously automatically open the first electromagnetic valve 23. Then, after a fixed time elapses, only the first electromagnetic valve 23 will be closed. When feeding water ends and the switch 132 is switched off, the second electromagnetic valve 27 will close.

Figure 26A:
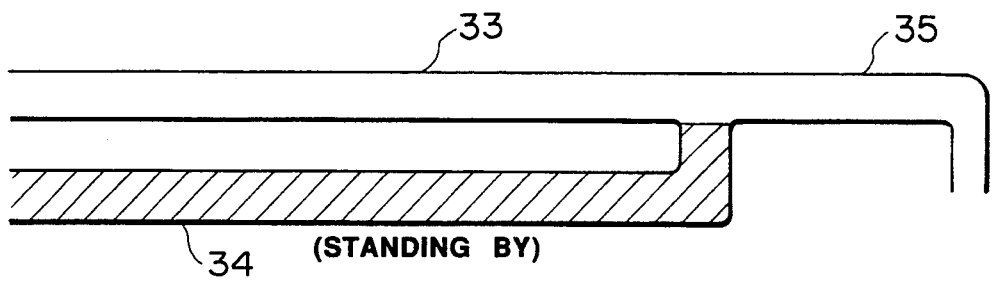
Figure 26B:
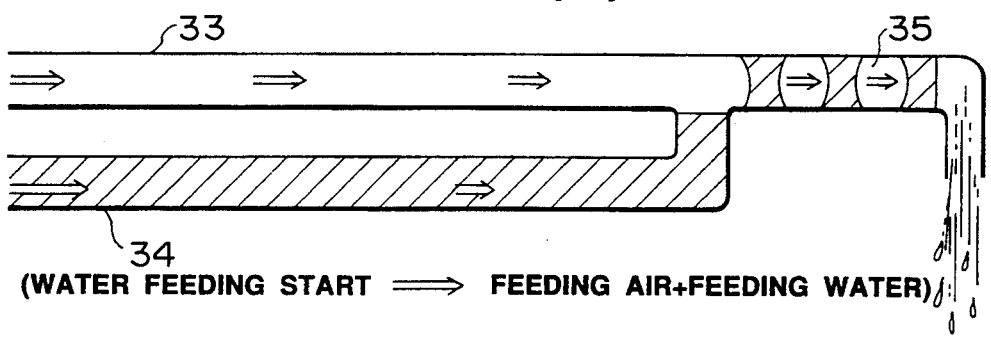
Figure 26C:
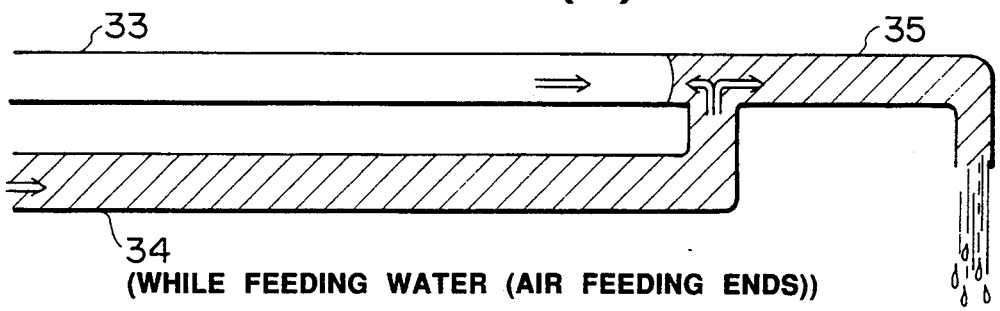
Figure 26D:
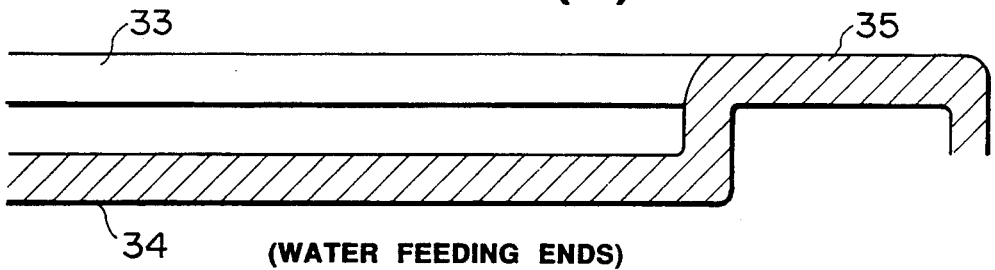
Figure 27A:
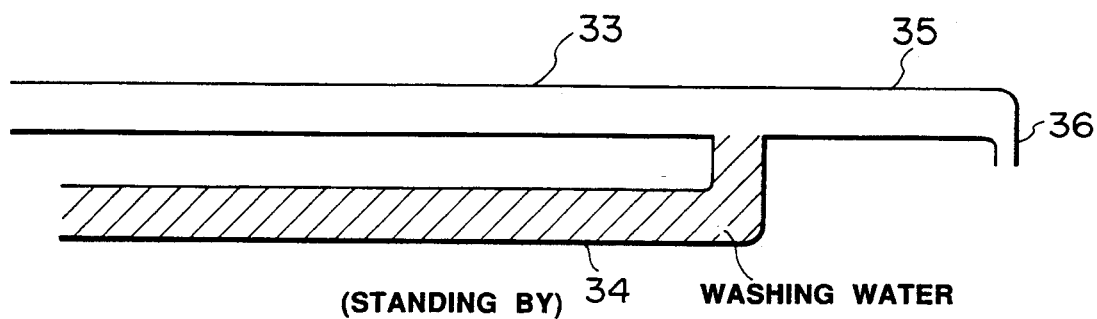
Figure 27B:
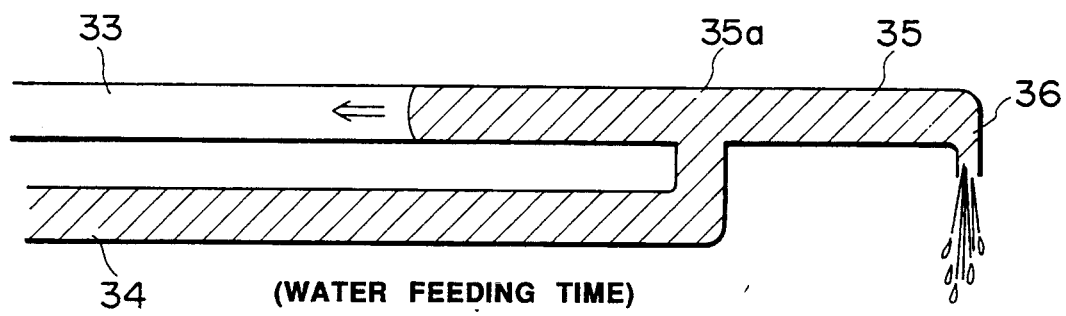

According to this embodiment, as shown in FIG. 26(B), from the standing by status shown in FIG. 26(A), simultaneously with starting feeding water, when air is fed for a fixed time, as in FIG. 26(C), the internal pressure in the air feeding pipeline 33 will be elevated and, even if feeding air is stopped, the pipeline internal pressure substantially the same as the fed water pressure will be maintained and therefore the washing water will not flow back into the air feeding pipeline 33. Therefore, as shown in FIG. 26(D), after feeding water ends, no water drops will remain within the air feeding pipeline 33.

Then, after the endoscope inspection ends, the pipeline will be washed by switching the switch 134 on. That is to say, when the switch 134 is switched on, the controlling part 46 will sense it and will automatically make the following control. First of all, the third electromagnetic valve 29 and the second electromagnetic valve 27 will be simultaneously opened, the air feeding pipeline 33 and water feeding pipeline 34 will be washed for a fixed time and then will be closed to end the washing of the air feeding pipeline 33 and water feeding pipeline 34. Then, both pipelines will be controlled to remove water. First, the fourth electromagnetic valve 129 will be opened to remove water in both pipelines and then will be closed. Then, the first electromagnetic valve 23 will be opened to remove water in the air feeding pipeline 33 and then will be closed. Thus, both pipelines will be washed and have water removed by the one-touch operation of pushing the switch 134.

Figure 28:
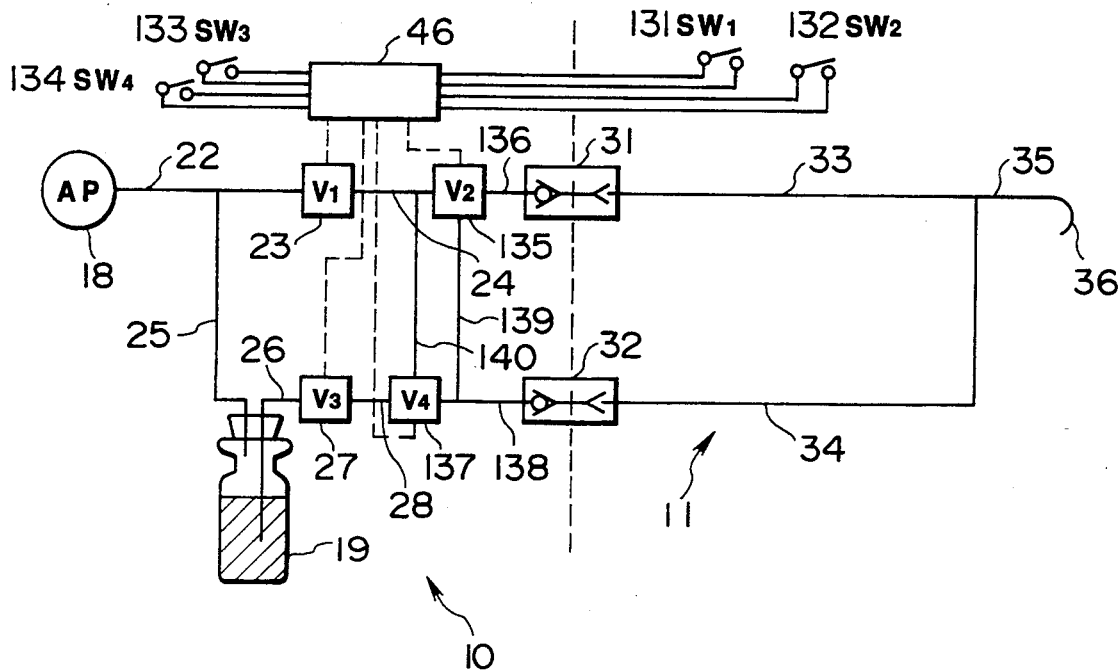
Figure 29:
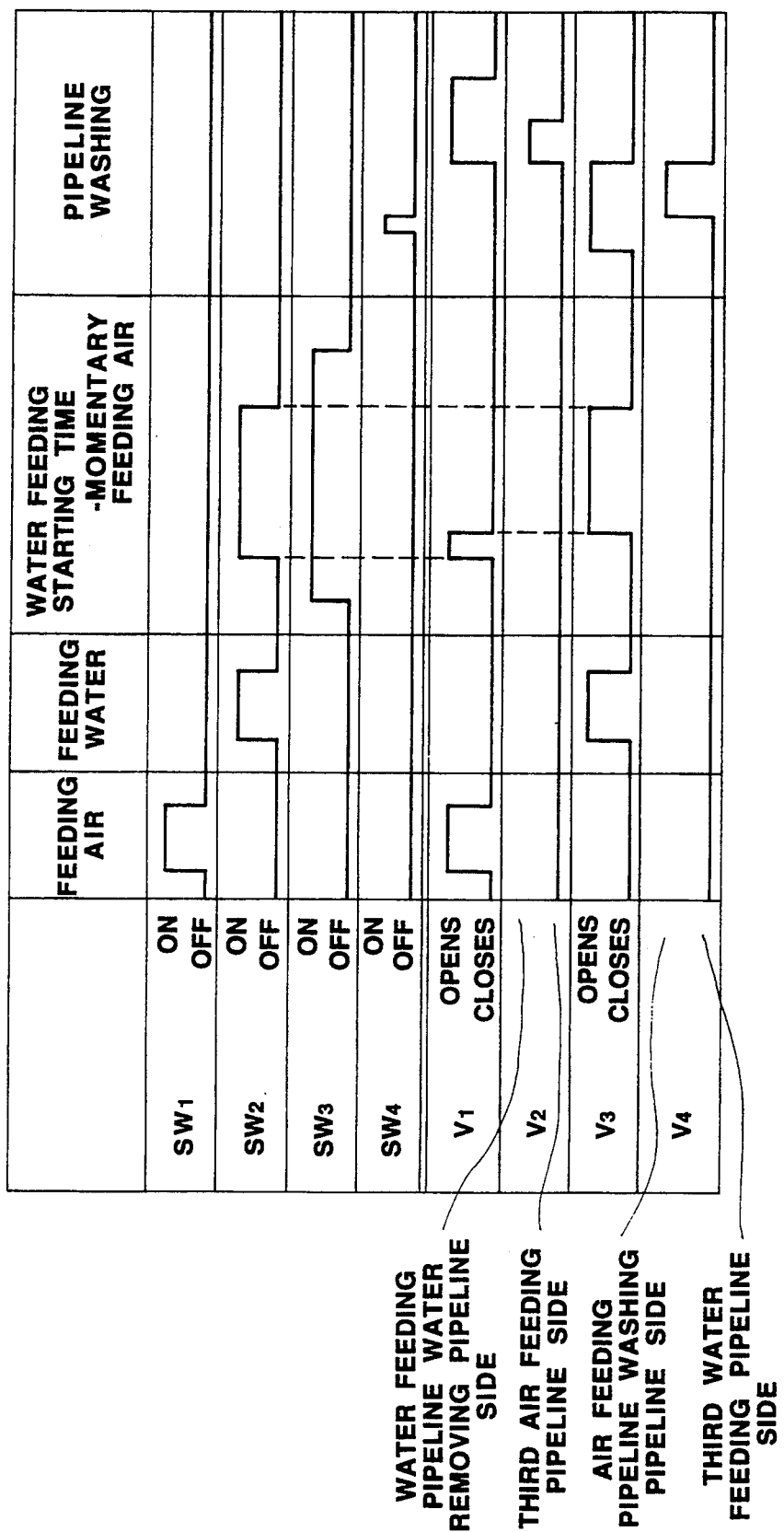

FIGS. 28 and 29 illustrate a modification of the fourth embodiment.

In the pipeline diagram shown in FIG. 28, a first air feeding pipeline 33 is connected to an air feeding pump 18 and is provided with a first electromagnetic valve (V1) 23 to which is connected a second air feeding pipeline 24, Further, to this second air feeding pipeline 24 is connected a third air feeding pipeline 136 through a second electromagnetic valve (V2) 135. An air feeding pressurized pipeline 25 communicating with the upper space within an air feeding tank 19 is branched and connected in the course of the above-mentioned first air feeding pipeline 22. A first water feeding pipeline 26 is connected to the above-mentioned water feeding tank 19 and to this first water feeding pipeline 26 is connected a second water feeding pipeline 28 through a third electromagnetic valve (V3) 27. Further, to this second water feeding pipeline 28 is connected a third water feeding pipeline 138 through a fourth electromagnetic valve (V4) 137. Each of the above-mentioned second electromagnetic valve 135 and fourth electromagnetic valve 137 is a three-way valve and has another outlet. The second electromagnetic valve 135 is joined and connected with the third water feeding pipeline 138 through a water feeding pipeline water removing pipeline 139. The other fourth electromagnetic valve 137 is joined and connected with the second air feeding pipeline 24 through an air feeding pipeline washing pipeline 140. The above-mentioned third air feeding pipeline 136 and third water feeding pipeline 138 are, respectively, connected to communicate with an air feeding pipeline 33 and water feeding pipeline 34 provided within the endoscope 11, respectively, through quick joints 31 and 32. These water feeding pipelines 33 and 34 join with each other in the course to form an air and water feeding pipeline 35 which communicates with the nozzle 36.

The first electromagnetic valve 23, second electromagnetic valve 135, third electromagnetic valve 27 and fourth electromagnetic valve 137 are all electrically connected with the controlling part 46. Further, the controlling part 46 is connected with the switches (SW1) 131 and (SW2) 132 provided in the operating section 12 and the switches (SW3) 133 and (SW4) 134 provided in the sheath of the controlling apparatus 10.

In such formation, as shown in the time chart in FIG. 29, during the usual endoscope inspection, air and water are fed by switching on/off the switches 131 and 132. While standing by, the first electromagnetic valve 23 and third electromagnetic valve 27 will be closed and the second electromagnetic valve 136 and fourth electromagnetic valve 137 will be opened, respectively, on the third air feeding pipeline 136 side and the third water feeding pipeline 138 side. In feeding air, when the switch 131 is switched on, as operatively connected with it, the controlling part 46 will open the first electromagnetic valve 23 and, when the switch 131 is switched off, the valve 23 will be closed. In feeding water, in the same manner, when the switch 132 is switched on, the controlling part 46 will open the third electromagnetic valve 27 and, when the switch 132 is switched off, the valve 27 will be closed.

In this modification, a control of momentarily feeding air just before starting feeding water is made as follows. First of all, the switch 133 switching usually feeding water and momentarily feeding air just before starting feeding water over to each other is switched on. In this state, when the switch 132 is switched on, the controlling part 46 will sense those signals and will automatically make the following control from the standing by status. First, the first electromagnetic valve 23 will be opened for a fixed time and then will be closed. Simultaneously with closing the third electromagnetic valve 23, the third electromagnetic valve 27 will be opened. The valve 27 will be kept open until the switch 132 is switched off. When the switch 132 is switched off, it will be operatively connected to close the third electromagnetic valve 27 so that air will be momentarily fed when water is fed. In the above-described fourth embodiment, air will be momentarily fed simultaneously with starting feeding water but, in this modification, air will be fed for a fixed time just before starting feeding water in the control. The effect will not be different from that of the fourth embodiment. The time for feeding air just before feeding water may be freely set to be, for example, 0.1 to 2 seconds.

On the other hand, after the endoscope inspection ends, when the switch 134 is momentarily switched on, the controlling part 46 will automatically control the pipelines to be washed as follows. That is to say, when the third electromagnetic valve 26 is first opened from standing by, the water feeding pipeline 24 will be washed. Then, when the third electromagnetic valve 27 is kept open and the outlet of the fourth electromagnetic valve 137 is switched over to the air feeding pipeline washing pipeline 139 side, the air feeding pipeline 33 will be washed. After the washing ends, when the third electromagnetic valve 27 is closed, the outlet of the fourth electromagnetic valve 137 is switched over to the third water feeding pipeline 138 side, then the first electromagnetic valve 23 is opened and the outlet of the second electromagnetic valve 135 is switched over to the water feeding pipeline water removing pipeline 139 side, the water in the water feeding pipeline 34 will be removed. When the outlet of the second electromagnetic valve 135 is switched over to the third air feeding pipeline 136 side, the water in the pipeline 33 will be removed and standing by will return. In these steps, the air feeding pipeline 33 and water feeding pipeline 34 will be separately washed and have water removed.

Figure 30:
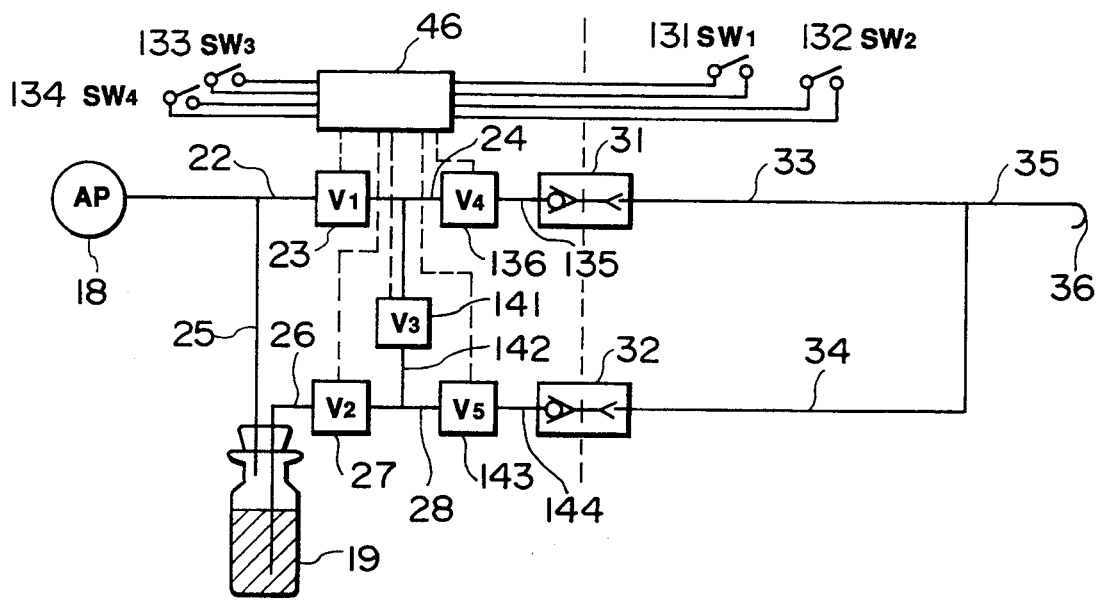
Figure 31:
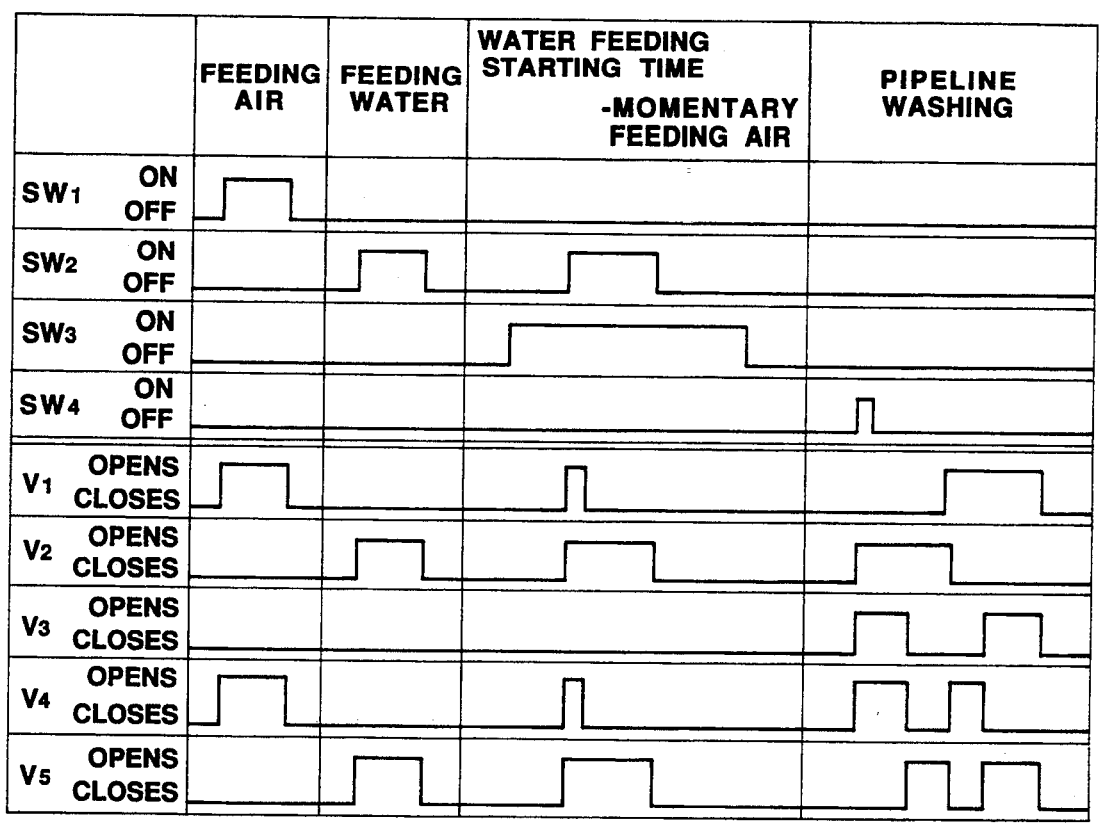

FIGS. 30 and 31 are of further another modification.

In FIG. 30, the reference numeral 18 represents an air feeding pump. A first air feeding pipeline 22 is connected to this air feeding pump 18 and is provided with a first electromagnetic valve (V1) 23 through which a second air feeding pipeline 24 is connected to the first air feeding pipeline 22. In the course of the first air feeding pipeline 22, a water feeding pressurized pipeline 25 is branched and connected to communicate with a water tank 19 to which is connected a first water feeding pipeline 26. To the above-mentioned first water feeding pipeline 26 is connected a second water feeding pipeline 28 through a second electromagnetic valve (V2) 27. The above-mentioned second air feeding pipeline 24 and second water feeding pipeline 28 communicate with a washing water removing pipeline 142 fitted with a third electromagnetic valve (V3) 141. Further, a third air feeding pipeline 135 is connected to the above-mentioned second air feeding pipeline 24 through a fourth electromagnetic valve (V4) 136. On the other hand, to the second water feeding pipeline 28 is connected a third water feeding pipeline 144 through a fifth electromagnetic valve (V5) 143. The third air feeding pipeline 135 and third water feeding pipeline 144 are fitted respectively with quick joints 31 and 32 so as to be connected by one touch respectively with an air feeding pipeline 33 and water feeding pipeline 34 of the endoscope. The air feeding pipeline 33 and the water feeding pipeline 34 join with an air and water feeding pipeline 35 to communicate with the nozzle 36.

On the other hand, the first electromagnetic valve 23, second electromagnetic valve 27, third electromagnetic valve 141, fourth electromagnetic valve 136 and fifth electromagnetic valve 143 are respectively electrically connected to the controlling part 46. This controlling part 46 is connected to switches (SW1) 131 and (SW2) 132 provided in the operating section and switches (SW3) 133 and (SW4) 134 provided in the controlling apparatus.

In such formation, as shown in the time chart in FIG. 31, while standing by during the endoscope inspection, all the first to fifth electromagnetic valves will be closed. Air will be usually fed when the controlling part 46 opens and closes the first electromagnetic valve 23 and fourth electromagnetic valve 136 by switching on/off the switch 131. On the other hand, water will be fed when the controlling part 46 simultaneously opens and closes the second electromagnetic valve 27 and fifth electromagnetic valve 143 by switching on/off the switch 132.

A control of momentarily feeding air simultaneously with starting feeding water shall be shown in the following.

First of all, while the switch 133 switching usual feeding air and feeding water while feeding air simultaneously with starting feeding water over to each other is on, when the switch 132 is switched on, simultaneously with the operation of switching on the switch 132, the controlling part 46 will open the first electromagnetic valve 23, second electromagnetic valve 26, fourth electromagnetic valve 136 and fifth electromagnetic valve 143 and, after a fixed time elapses, the controlling part 46 will close the first electromagnetic valve 23 and fourth electromagnetic valve 136. This state is automatically controlled to be maintained until the switch 132 is switched off and, when the switch 132 is switched off, as operatively connected with it, the second electromagnetic valve 27 and fifth electromagnetic valve 143 will be closed. Thereby, simultaneously with starting feeding water, air will be fed for a fixed time. By the way, the time of feeding air at the time of starting feeding water can be freely set to be, for example, 0.1 to 2 seconds. Further, as in this embodiment, when air and water are fed for a fixed time from starting feeding water, as a result, spray water will be fed for a fixed time and an effect of improving the observing window washing force will be seen.

When the endoscope inspection ends, the pipeline will be washed as follows. First of all, when the switch 134 is switched on, the second electromagnetic valve 27, third electromagnetic valve 141 and fourth electromagnetic valve 136 will be opened, the air feeding pipeline 33 will be washed by feeding water for a fixed time, then the second electromagnetic valve 27 will be left open, the third electromagnetic valve 141 and fourth electromagnetic valve 136 will be closed and the fifth electromagnetic valve 143 will be opened so that the pipeline 34 will be washed by feeding water. Then, the second electromagnetic valve 27 and fifth electromagnetic valve 143 will be closed and then the first electromagnetic valve 23 and fourth electromagnetic valve 136 will be opened so that water in the air feeding pipeline 33 will be removed. Then, the fourth electromagnetic valve 136 will be closed and the third electromagnetic valve 141 and fifth electromagnetic valve 143 will be opened so that water in the water feeding pipeline 34 will be removed. After removing water ends, standing by status will return. When such control is automatically made by the controlling part, both pipelines will be separately washed by feeding water and will have water removed.

Figures 32, 33:
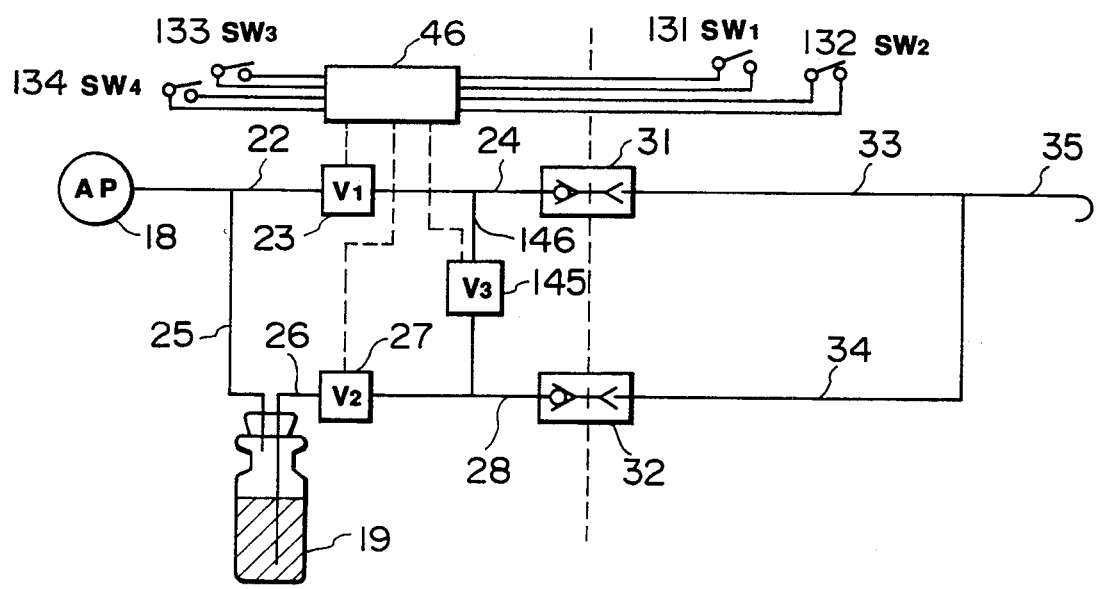

FIGS. 32 and 33 show another modification of the fourth embodiment.

In FIG. 32, the reference numeral 18 represents an air feeding pump. A first air feeding pipeline 22 is connected to the air feeding pump 18. To this first air feeding pipeline 22 is connected a second air feeding pipeline 24 through a first electromagnetic valve (V1) 23. A water feeding pressurized pipeline 25 is branched and connected to the first air feeding pipeline 22 and communicates with a water feeding tank 19. A first water feeding pipeline 26 is connected to the water feeding tank 19 and communicates with a second water feeding pipeline 28 through a second electromagnetic valve (V2) 27. The above-mentioned second air feeding pipeline 24 and second water feeding pipeline 28 communicate with each other through a washing pipeline 146 fitted with a third electromagnetic valve (V3) 145. The second air feeding pipeline 24 and second water feeding pipeline 28 communicate respectively with an air feeding pipeline 33 and water feeding pipeline 34 of the endoscope, respectively, through quick joints 31 and 32 and join with each other on the tip side of the insertable section to form an air and water feeding pipeline 35. By the way, the first electromagnetic valve 23, second electromagnetic valve 27 and third electromagnetic valve 145 are electrically connected to the controlling part 46 to which are connected switches (SW1) 131 and (SW2) 132 provided in the endoscope operating section and switches (SW3) 133 and (SW4) 134 provided in the sheath of the controlling apparatus.

The operation shall be explained in the following on the basis of the time chart shown in FIG. 33. First of all, the operations of usual feeding air and water shall be explained. In usual feeding air, when the switch 131 is switched on/off, the controlling part 46 will sense the signal and will open and close the first electromagnetic valve 23. That is to say, when the switch 131 is switched on, the first electromagnetic valve 23 will be opened and, when the switch 131 is switched off, the valve 23 will be operatively connected to be closed. The same as in feeding water, the controlling part 46 will be operatively connected with the switch 132 being on/off to open and close the second electromagnetic valve to feed water. Now, the operation of momentarily feeding air simultaneously with starting feeding water shall be explained. First, the switch 133 switched to the control of feeding air simultaneously with starting feeding water from usual feeding air is switched on. While this switch 133 is on, when the switch 132 is switched on, the controlling part 6 will sense the signal, will open the first electromagnetic valve 23 simultaneously with opening the second electromagnetic valve 27 and will close only the first electromagnetic valve 23 after a fixed time elapses. This state is maintained until the switch 132 becomes off. When the switch 132 is switched off, a control of closing the second electromagnetic valve 27 will be made so that air will be momentarily fed simultaneously with starting feeding water.

By the way, when the switch 134 is on, the first electromagnetic valve 23, second electromagnetic valve 27 and third electromagnetic valve 145 will be controlled to open and close so that the pipelines may be washed after the endoscope inspection ends.

Figures 34, 35:
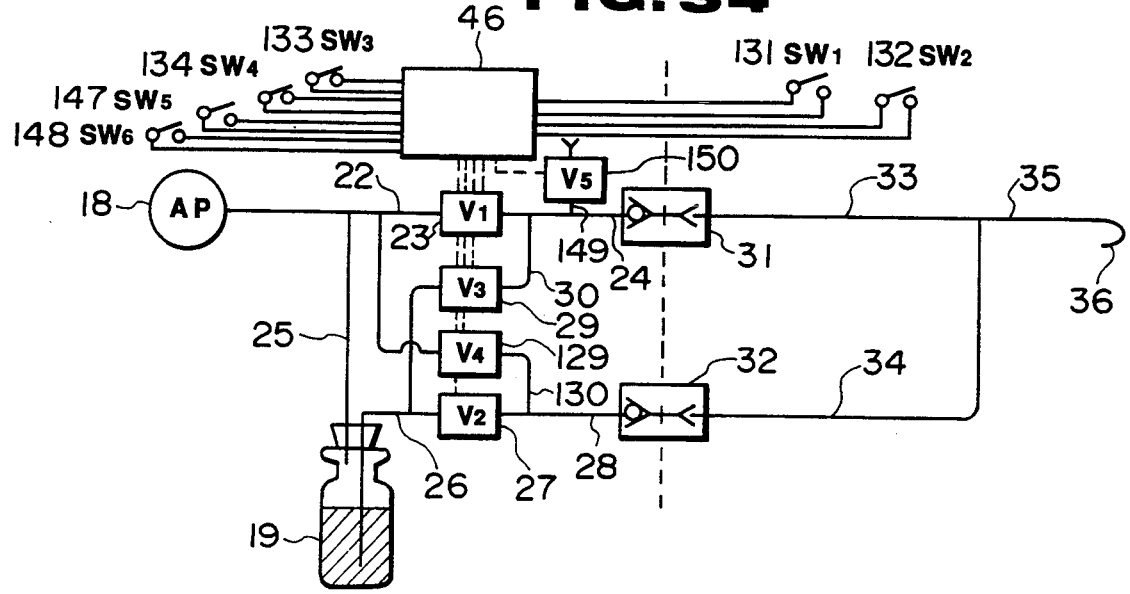

FIGS. 34 and 35 show further another modification of the fourth embodiment.

In this modification, in order to improve the water cuttability, the control of momentarily feeding air after feeding water and the control of venting air feeding pipelines after feeding water are both used. This modification is formed by a little modifying the above described fourth embodiment. Only the differences from the fourth embodiment shall be explained.

In this modification, a venting pipeline 149 is branched from the second air feeding pipeline 24 and is connected with a fifth electrode 150 which is opened at the outlet to the atmosphere and is electrically connected to the controlling part 46. Switches (SW5) 147 and (SW6) 148 provided in the sheath of the controlling apparatus are connected to this controlling part 46.

This formation operates as shown in the flow chart in FIG. 35.

The operation of combining the use of the control of automatically feeding air after feeding water shall be shown. First of all, the switch 133 momentarily feeding air simultaneously with starting feeding water and the switch 147 automatically feeding air after feeding water are switched on. When the switch 132 is switched on while these both switches are on, the controlling part 46 will open the second electromagnetic valve, will simultaneously open the first electromagnetic valve 23 and will close the valve 23 after a fixed time elapses. This state is maintained until the switch 132 is off. When the switch 132 is switched off, as operatively connected with it, the second electromagnetic valve 27 will be closed and, simultaneously with it, the first electromagnetic valve 23 will be opened for a fixed time and then will be closed, such control being made automatically. Thereby, the evacuation of water droplets will be better than by only the control of automatically feeding air after feeding water. Now, the operation in the case of the combined use of the control of venting the air feeding pipeline after feeding water shall be explained. First, the switches 148 and 133 for venting the air feeding pipeline after feeding water are switched on. When the switch 132 provided in the operating section is switched on in this state, simultaneously with it, the controlling part 46 will open the second electromagnetic valve 27 and first electromagnetic valve 23 and will close the first electromagnetic valve 23 after a fixed time elapses. When the switch 132 is then switched off, the second electromagnetic valve 27 will be closed and simultaneously the fifth electromagnetic valve 150 will be opened and will be closed after a fixed time elapses, such control being made automatically. Thereby, the washing water will not jet out of the venting pipeline 149, the response to stopping feeding water will improve and the evacuation of water droplets will improve.

Figure 36:
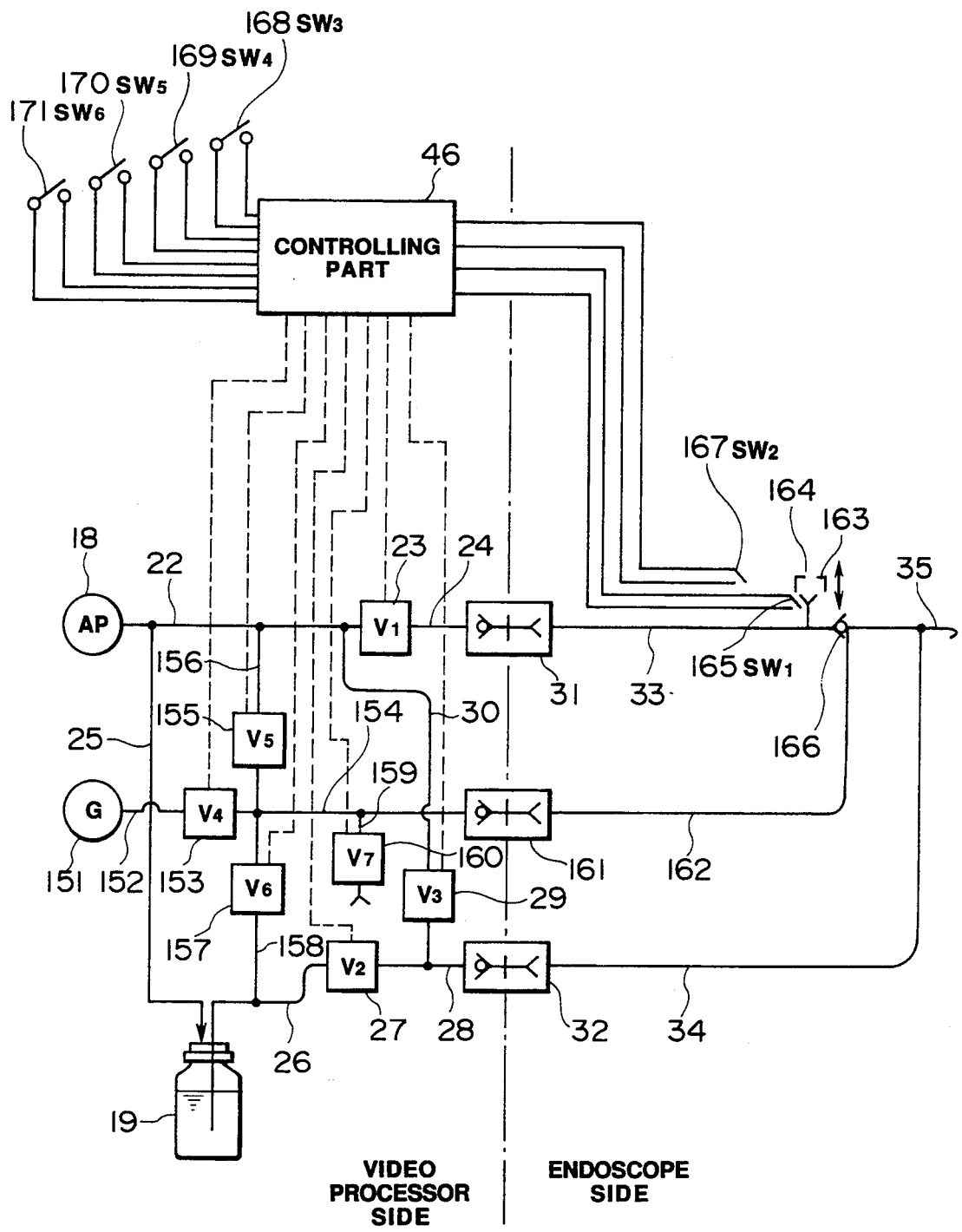
FIGS. 36 and 37 relate to the fifth embodiment of the present invention.
Figure 37:
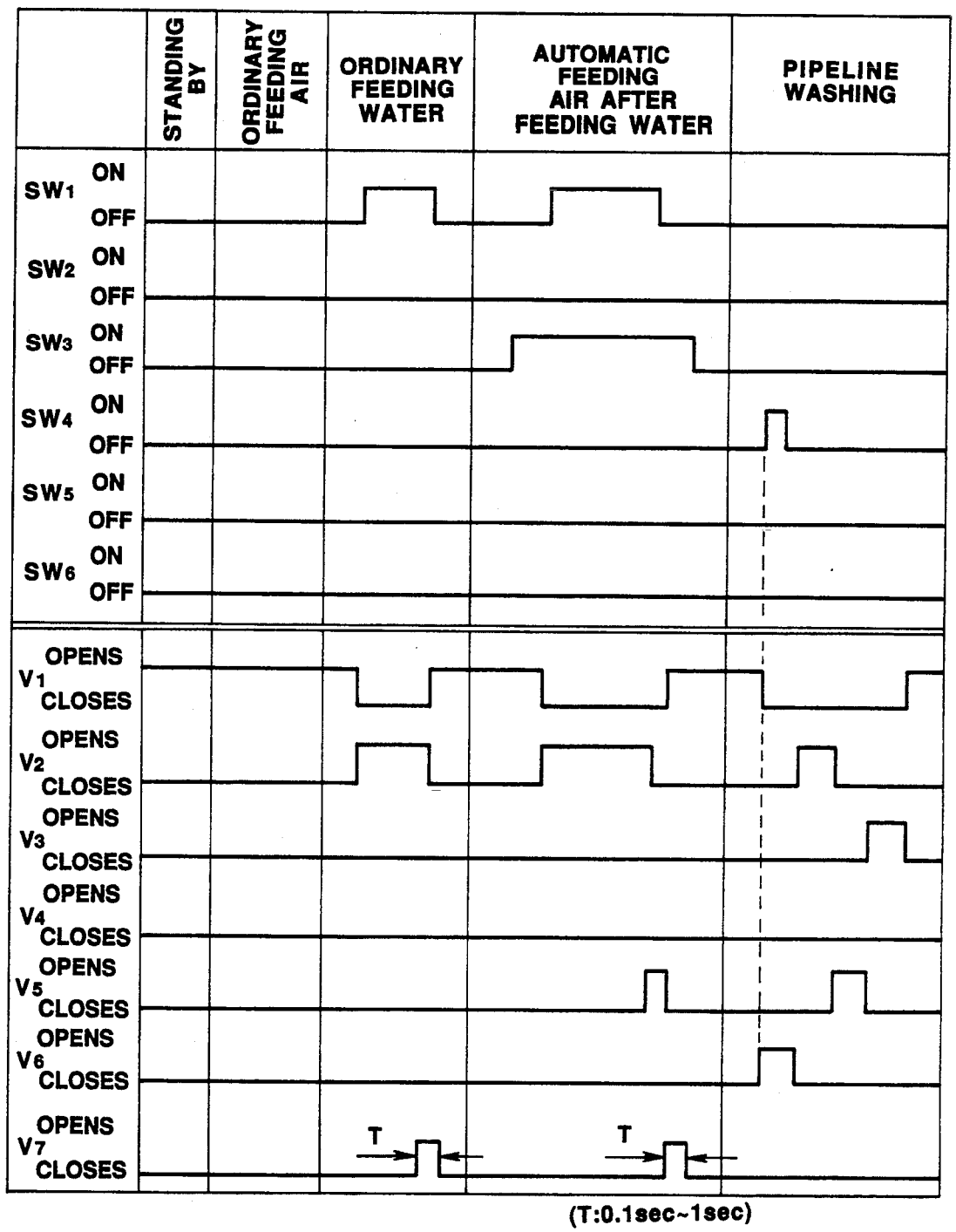

FIGS. 36 to 37 show the fifth embodiment.

In the pipeline diagram shown in FIG. 36, a first air feeding pipeline 22 is connected to an air feeding pump 18 and is connected with a second air feeding pipeline 24 through a first electromagnetic valve (V1) 23. Further, in the course of the first air feeding pipeline 22, a water feeding air feeding pipeline 25 is branched and connected and is connected to a water feeding tank 19 to which is further connected a first water feeding pipeline 26 and is connected a second water feeding pipeline 28 through a second electromagnetic valve (V2) 27. The above-mentioned first air feeding pipeline 22 and second water feeding pipeline 28 communicate with a water feeding pipeline water removing pipeline 30 having a third electromagnetic valve (V3) 29 which is provided near the branching part of the second water feeding pipeline 28 and the water feeding pipeline water removing pipeline 30. To a gas bottle 151 filled with a nonflammable gas is connected a first pipeline 152 and is further connected through a fourth electromagnetic valve (V4) 153 a second gas pipeline 154 used also as an air feeding pipeline feeding a gas and air. The above-mentioned second gas pipeline 154 and first air feeding pipeline 22 communicate with each other through a gas pipeline water removing air feeding pipeline 156 having a fifth electromagnetic valve (V5) 155. Further, the second gas pipeline 154 and first water feeding pipeline 26 communicate with each other through a gas pipeline (also an air feeding pipeline) washing pipeline 158 having a sixth electromagnetic valve (V6). By the way, in order to positively remove water, the gas pipeline water removing air feeding pipeline 156 communicates with the second gas pipeline 154 on the side of the gas bottle 151 rather than the gas pipeline washing pipeline 158.

Further, the second gas pipeline 154 is provided with a venting pipeline 159 so as to be able to vent to the atmosphere through a seventh electromagnetic valve (V7) 160. Also, the second air feeding pipeline 24, second gas pipeline 154 and second water feeding pipeline 28 are fitted at the ends respectively with joints 31, 161 and 32 so as to be connected respectively to an air feeding pipeline 33, gas pipeline 162 and water feeding pipeline 34 on the endoscope side. In the course within the endoscope, the air feeding pipeline 33 communicates with a button 163 provided in the operating section and opens in a venting hole 164 provided in the upper part of the button 163. A switch (SW1) 165 which will be switched on when this button 163 is pushed in is provided. The air feeding pipeline 33 is provided with a check valve 166 in a position on the side of the insertable section rather than the button 163 provided in the operating section. Further, a gas pipeline 162 communicates with the check valve 166 on the insertable section tip side.

Further, the air feeding pipeline 33 and water feeding pipeline 34 join with each other to form an air and water feeding pipeline 35 on the tip side of the endoscope insertable section. The above-mentioned first to seventh electromagnetic valves 23, 27, 29, 153, 155, 157 and 160 are, respectively, electrically connected to the controlling part 46. On the other hand, to this controlling part 46 are connected switches (SW1) 165 and (SW2) 167 provided in the operating section of the endoscope and switches (SW3) 168, (SW4) 169, (SW5) 170 and (SW6) 171 provided in the sheath of a controlling apparatus, not illustrated.

By the way, the water feeding pipeline 34 has an inside diameter substantially the same as that of the air feeding pipeline 33 and gas pipeline 162 but the water feeding pipeline 34 is made of a material having a higher friction coefficient against water or washing water than the other pipelines.

In such formation, as shown in the time chart in FIG. 37, usually air and water are fed by the operations of the button 13 and switch 165 provided in the operating section. That is to say, in feeding air, while standing by with only the first electromagnetic valve 23 opened, when the venting hole 164 provided in the button 163 is clogged with a finger, the check valve 166 will be opened by the pressure of the air feeding pump 18 and air will be fed to the insertable section at the tip. On the other hand, in feeding water, when the switch 165 is switched on, this switch 165 will be on and the controlling part 46 will sense the signal, will close the first electromagnetic valve 23 and will simultaneously open the second electromagnetic valve 27 so that washing water will be fed to the water feeding pipeline 34 and water will be fed. When the switch 165 is switched off, the second electromagnetic valve 27 will be closed, the first electromagnetic valve 23 will be opened and, at the same time, the seventh electromagnetic valve 160 will be momentarily opened to end feeding water.

The pipeline is washed by switching the switch 169 on momentarily. That is to say, when this switch 169 is switched on, the controlling part 46 will sense it and will automatically make the following control. First of all, the first electromagnetic valve 23 will be closed from standing by status. At the same time, the sixth electromagnetic valve 157 will be opened, the gas pipeline 162, check valve 166 and air feeding pipeline 33 on the tip side will be washed for a fixed time and then the sixth electromagnetic valve 157 will be closed so that the washing of the gas pipeline 162 and air feeding pipeline will end. Simultaneously with closing the sixth electromagnetic valve 157, the second electromagnetic valve 27 will be opened so that the water feeding pipeline 34 will be washed for a fixed time and the second electromagnetic valve 27 will be closed. When the second electromagnetic valve 27 is closed, the fifth electromagnetic valve 155 will be opened to remove water out of the gas pipeline and will be closed after a fixed time. When the fifth electromagnetic valve 155 is closed, the third electromagnetic valve 29 will be opened to remove water of the water feeding pipeline 34 and will be closed after removing water. Simultaneously with closing the third electromagnetic valve 29, the first electromagnetic valve 23 will be opened and will return to standing by status.

After feeding water, air is automatically fed as follows.

First, the switch 168 is switched on. When the button 163 is pushed in in this state and the switch 165 is switched on, the first electromagnetic valve 23 will close and the second electromagnetic valve 27 will open. When the switch 165 is switched off, the second electromagnetic valve 27 will close and simultaneously with it the fifth electromagnetic valve 155 will momentarily open and then will close so that air will be automatically fed after feeding water.

Here, as the water feeding pipeline 34 is formed of a material higher in the friction coefficient than of the air feeding pipeline 33 and gas pipeline 162, the water feeding resistance will be higher than the air feeding resistance, therefore, while feeding water, the air within the first air feeding pipeline 22, water feeding air feeding pipeline 25 and water feeding tank will be compressed by the air fed from the air feeding pump 18 and the compressed air will be immediately fed to the observing window through the gas pipeline 162 after feeding water and will be able to blow away the water drops remaining on the observing window.

By the way, the means for increasing the water feeding resistance to be higher than the air feeding resistance is not limited to only that of the fifth embodiment but may be to provide the water feeding pipeline with a bend, elbow or orifice or to make the inside surface of the water feeding pipeline rougher than that of the air feeding pipeline.

FIGS. 38 to 42 show the sixth embodiment.

Figure 38:
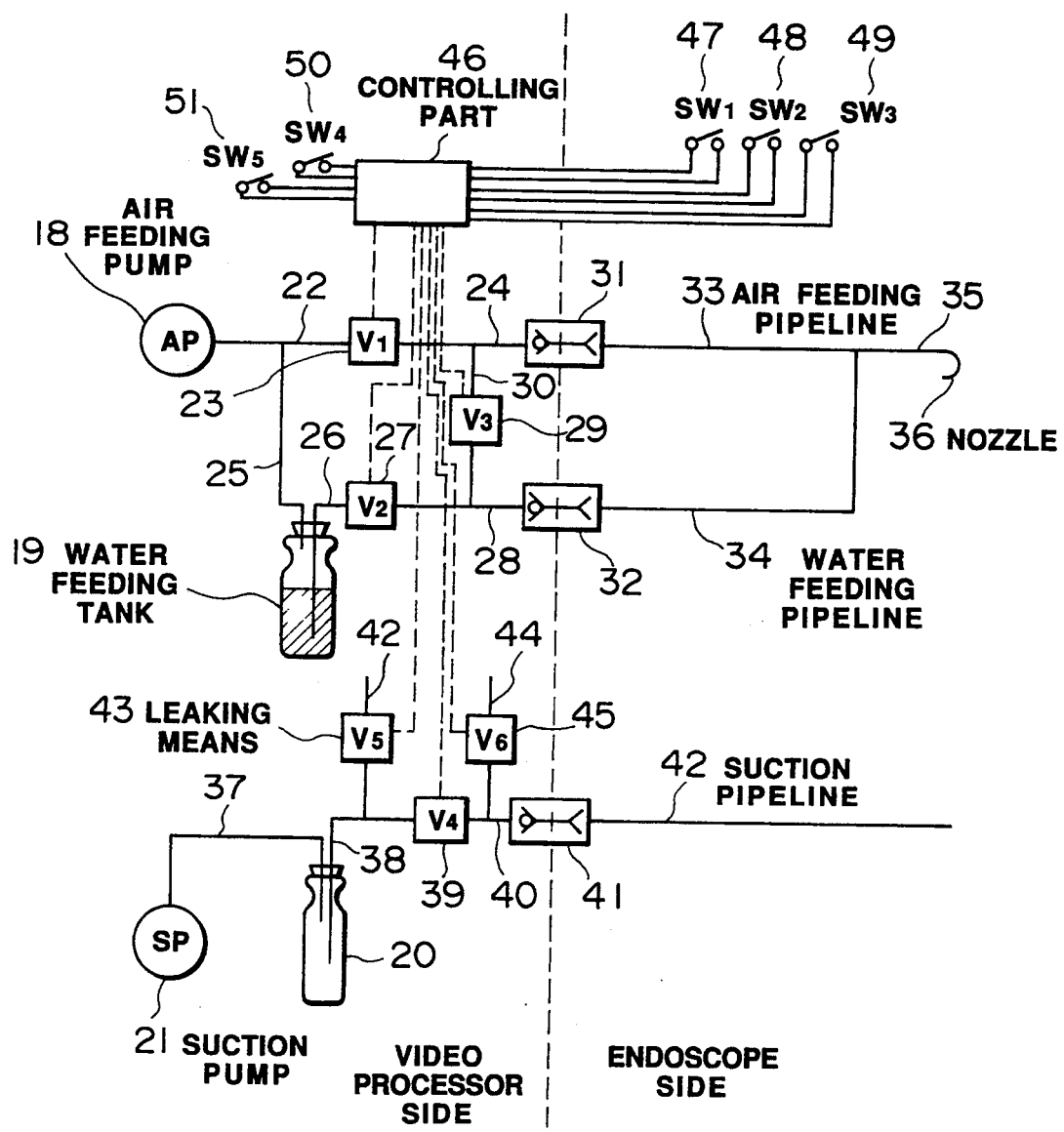
FIG. 38 is a pipeline diagram of an air and water feeding and sucking apparatus showing the sixth embodiment of the present invention.

In the pipeline diagram shown in FIG. 38, a first air feeding pipeline 22 is connected to an air feeding pump 18 and is provided with a first electromagnetic valve (V1) 23 to which is connected a second air feeding pipeline 24. In the course of the above-mentioned air feeding pipeline 22, a water feeding air feeding pipeline 25 is branched and connected to communicate with a water feeding tank 19 to which is connected a first water feeding pipeline 26 and is connected a second water feeding pipeline through a second electromagnetic valve (V2) 27. The above-mentioned second air feeding pipeline 24 and second water feeding pipeline 28 communicate with each other through an air feeding pipeline washing pipeline 30 fitted in the course with a third electromagnetic valve (V3) 29 which is provided in a position very close to the second water feeding pipeline 28. The above-mentioned second air feeding pipeline 24 and second water feeding pipeline 28 are provided at the ends, respectively, with joints 31 and 32 so as to be connected, respectively, with an air feeding pipeline 33 and water feeding pipeline 34 on the endoscope side. These air feeding pipeline 33 and water feeding pipeline 34 join with each other on the tip side of the endoscope insertable section 13 to form an air and water feeding pipeline 35 which communicates with a nozzle 36 opening toward the observing window in the endoscope tip part. On the other hand, to a suction pump 21 is connected a first sucking pipeline 37 which is connected to a suction bottle 20. Further, a second sucking pipeline 38 is connected to the suction bottle 20. A third sucking pipeline 40 is connected to the second sucking pipeline 38 through a fourth electromagnetic valve (V4) 39 which is a suction valve. This third sucking pipeline 40 is fitted at the end with a joint 41 so as to be connected with a venting pipeline 42 on the endoscope side. A venting pipeline 42 is branched from the second sucking pipeline 38 and communicates with the atmosphere through a fifth electromagnetic valve (V5) 43. A mucous membrane adsorption releasing pipeline 44 is branched from the third sucking pipeline 40 and communicates with the atmosphere through a sixth electromagnetic valve (V6) 45. Further, the above-mentioned first to sixth electromagnetic valves 23, 27, 29, 39, 43 and 45 are, respectively, electrically connected to the controlling part 46 controlling feeding and sucking air and water. On the other hand, to this controlling part 46 are connected switches (SW1) 47, (SW2) 48, and (SW3) 49 provided in the operating section of the endoscope and switches (SW4) 50 and (SW5) 51 provided in the sheath of a video processor 16.

Figure 39:
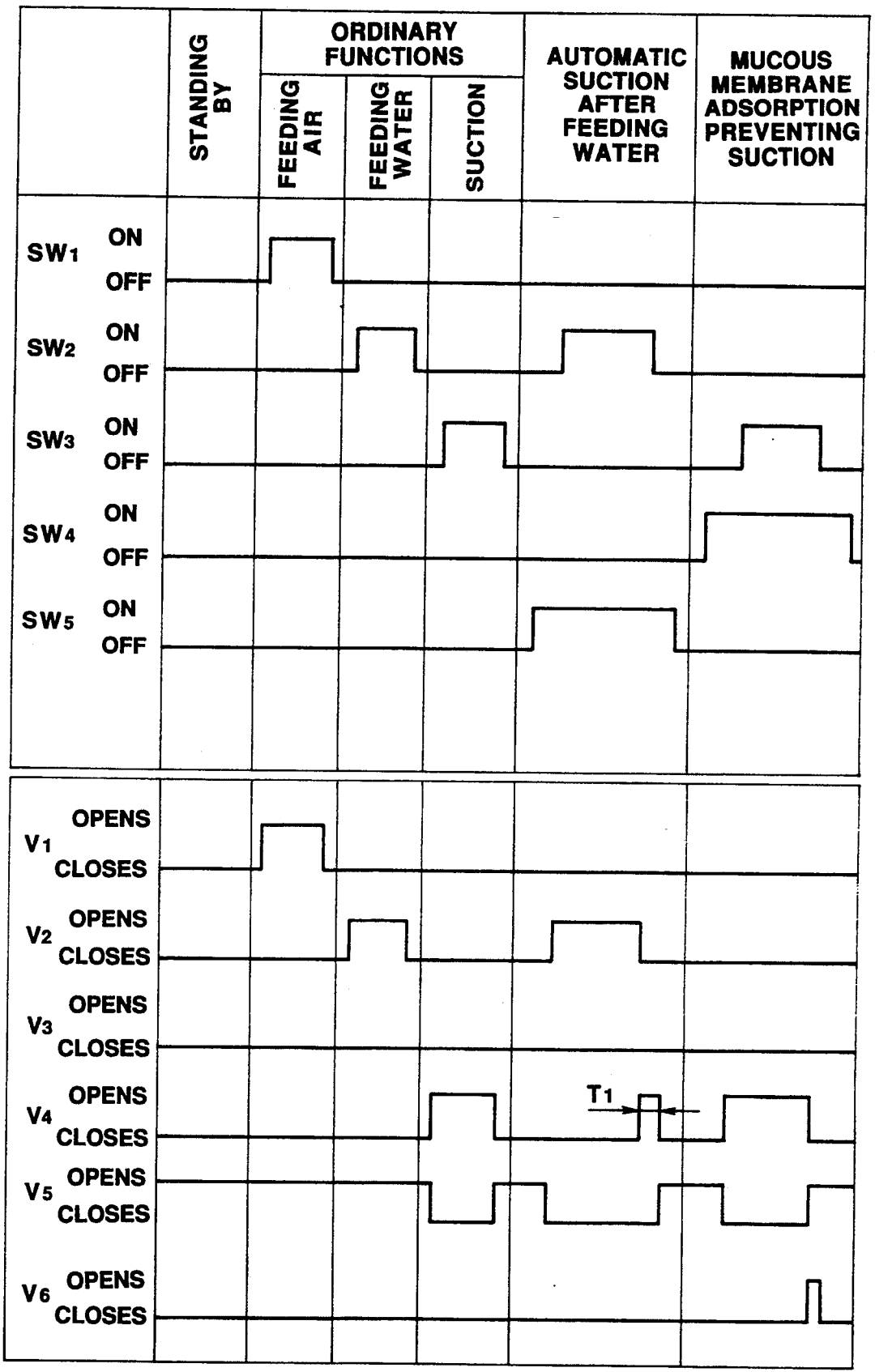
FIG. 39 is a time chart showing operation timings of respective switches and valves.

In such formation, as shown in the timing chart in FIG. 39, during the usual endoscope inspection, air and water are fed by switching on/off the switches 47 and 48 provided in the operating section 12. That is to say, in the case of feeding air, when the switch 47 is switched on, by the controlling part 46, the first electromagnetic valve 23 will be opened and air will be fed through the air feeding pipeline 33. On the other hand, in usually feeding water, when the switch 48 is switched on, the controlling part 46 will open the second electromagnetic valve 27 in the same manner and washing water will be fed to the water feeding pipeline 34.

In controlling the mucous membrane adsorption preventing suction for preventing the mucous membrane adsorption, first of all, the switch 50 is switched on. This switch 50 switches the usual suction and the mucous membrane adsorption preventing suction over to each other. When this switch 50 is on, if the switch 49 is switched on, by the controlling part 46, the fifth electromagnetic valve 43 will be closed from standing by and, at the same time, the fourth electromagnetic valve 39 will be opened to suck. When the switch 49 is switched off, as operatively connected with it, the fifth electromagnetic valve 43 will open, the fourth electromagnetic valve 39 will simultaneously close and further the sixth electromagnetic valve 45 will open for a fixed time and then will return to standing by so that the mucous membrane adsorption releasing pipeline 44 will temporarily communicate with the atmosphere, the negative pressure within the pipeline will be removed and the mucous membrane adsorption will be prevented.

The automatic suction after feeding water is made by the operations shown in the following.

Figure 40:
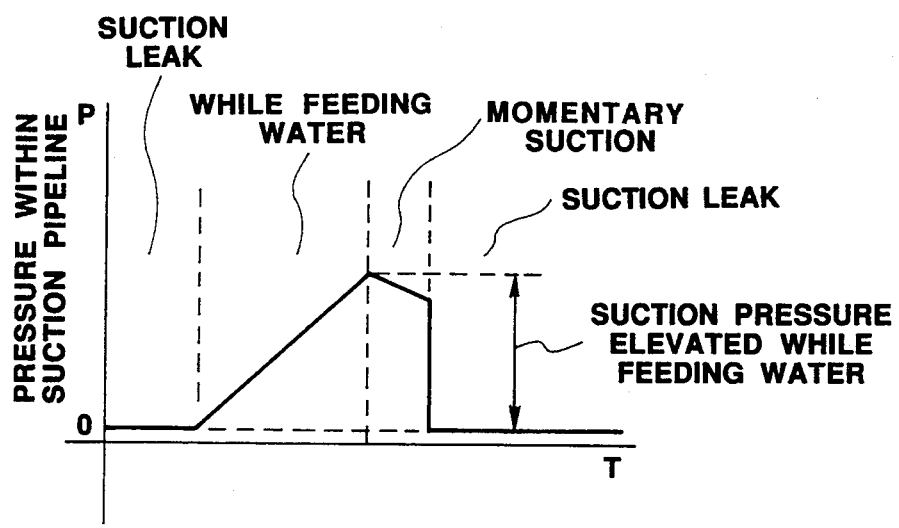
FIG. 40 is an explanatory diagram showing an internal pressure of a sucking pipeline.

First, the switch 51 is switched on. This switch 51 is to switch the usual feeding water and the automatic suction after feeding water over to each other. When this switch 51 is on, if the switch 48 is switched on, by the controlling part 46, the second electromagnetic valve 27 will be opened from standing by and, at the same time, the fifth electromagnetic valve 43 will close to feed water. When the switch 48 is switched off, as operatively connected with it, the second electromagnetic valve 27 will close and the fourth electromagnetic valve 39 will simultaneously momentarily open. Further, when the fourth electromagnetic valve 39 closes, the fifth electromagnetic valve 43 will open to leak to the atmosphere and will return to standing by. Thereby, as shown in FIG. 40, while feeding water, the suction pressure within the sucking pipeline from the suction pump 21 to the second sucking pipeline 38 will be elevated and a momentary suction will be automatically made by the suction pressure elevated after feeding water.

Figure 41:
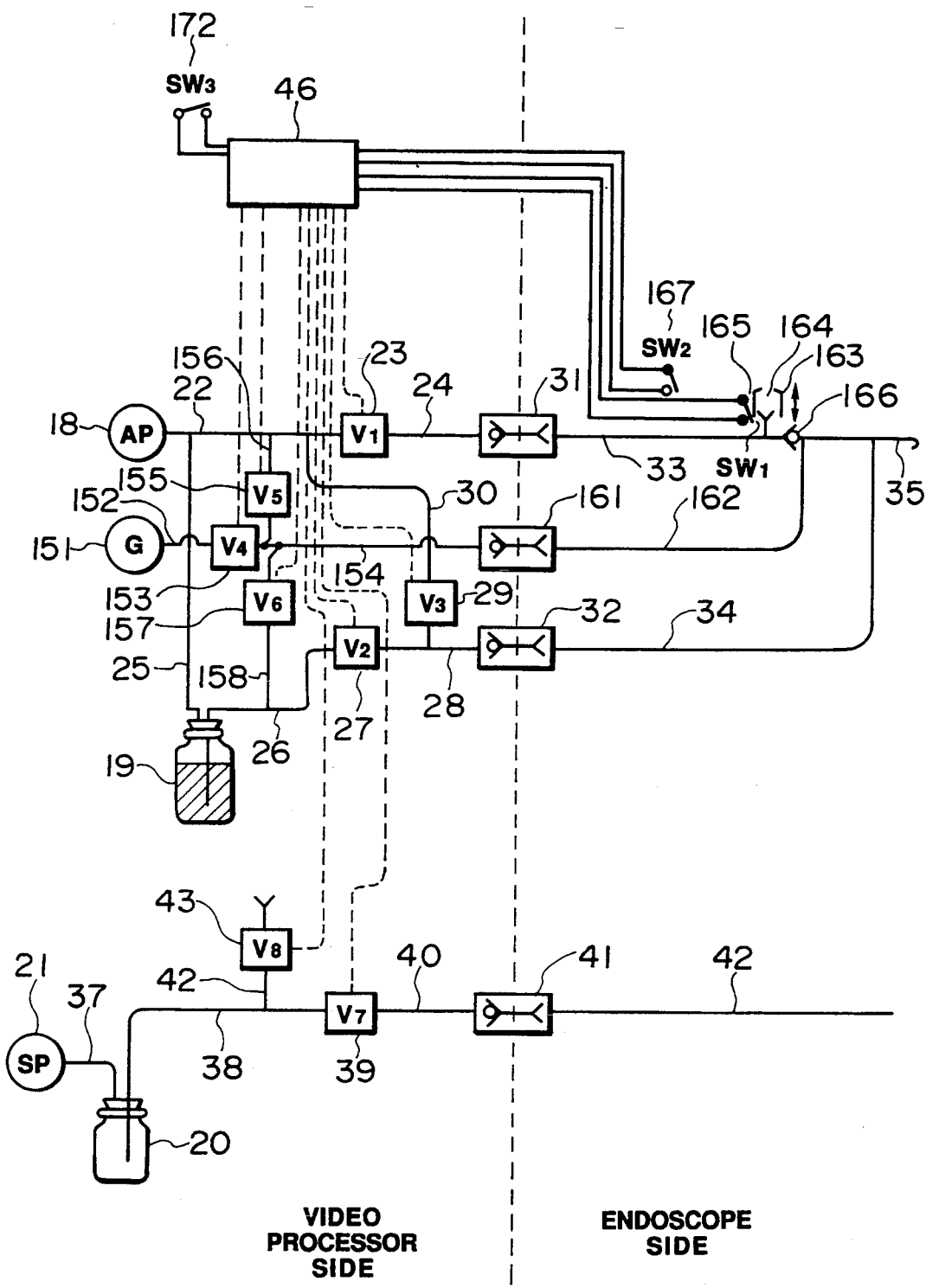
FIG. 41 is a pipeline diagram of an air and water feeding and sucking apparatus showing a modification of the sixth embodiment.

FIG. 41 is of a modification of the sixth embodiment.

In the pipeline diagram shown in FIG. 41, to an air feeding pump 18 is connected a first air feeding pipeline 22 to which is connected a second air feeding pipeline 24 through a first electromagnetic valve (V1) 23. Further, in the course of the first air feeding pipeline 22, a water feeding air feeding pipeline 25 is branched and connected and is connected to a water feeding tank 19 to which is further connected a first water feeding pipeline 26 and is connected a second water feeding pipeline 28 through a second electromagnetic valve (V2) 27. The above-mentioned first air feeding pipeline 22 and second water feeding pipeline 28 communicate with each other through a water feeding pipeline water removing pipeline 30 having a third electromagnetic valve (V3) 29. This third electromagnetic valve 29 is provided near the branching part of the second water feeding pipeline 28 and the water feeding pipeline water removing pipeline 30. To a gas bottle 151 filled with a nonflammable gas is connected a first gas pipeline 152 and is further connected through a fourth electromagnetic valve (V4) 153 a second gas pipeline 154 used also as an air feeding pipeline feeding a gas and air.

The above-mentioned second gas pipeline 154 and first air feeding pipeline 22 communicate with each other through a gas pipeline water removing air feeding pipeline 156 having a fifth electromagnetic valve (V5) 155. Further, the above-mentioned second gas pipeline 154 and first water feeding pipeline 26 communicate with each other through a gas pipeline (an air feeding pipeline) washing pipeline 158 having a sixth electromagnetic valve (V6) 157. By the way, in order to positively remove water, the gas pipeline water removing air feeding pipeline 156 communicates with the second gas pipeline 154 on the side of the gas bottle 151 rather than the gas pipeline washing pipeline 158. The second air feeding pipeline 24, second gas pipeline 154 and second water feeding pipeline are fitted at the ends, respectively, with joints 31, 161 and 32 so as to be connected, respectively, to an air feeding pipeline 33, gas pipeline 162 and water feeding pipeline 34 on the endoscope side. The air feeding pipeline 33 communicates in the course within the endoscope with a button 163 provided in the operating section and opens in a venting hole 164 provided in the upper part of the button 163 which is provided so as to be free to advance and retreat and is further provided with such switch (SW1) 165 as will be on when the button 163 is pushed in. The air feeding pipeline 33 is also provided with a check valve 166 in a position on the side of the insertable section rather than the button 163 provided in the operating section and further communicates with a gas pipeline 162 on the insertable section tip side of the check valve 166. Further, the air feeding pipeline 33 and water feeding pipeline 34 join with each other on the tip side of the endoscope insertable section to form an air and water feeding pipeline 35. On the other hand, the sucking pipeline system is connected with a suction pump 21 and first sucking pipeline 37 and communicates with a suction bottle 20 to which is also connected a second sucking pipeline 38 communicating with a seventh electromagnetic valve (V7) 39. Further, in the course of the second sucking pipeline 38, a sucking venting pipeline 42 is branched and connected and communicates with the atmosphere through an eighth electromagnetic valve (V8) 43. A third sucking pipeline 40 is connected to a seventh electromagnetic valve (V7) 39 and communicates through a joint 41 with the sucking pipeline 42 provided within the endoscope. The sucking pipeline 42 communicates with a channel opening opened in the tip part of the insertable section. The thus connected first to eighth electromagnetic valves 23, 27, 29, 153, 155, 157, 39 and 43 are electrically connected to the controlling part 46. On the other hand, to this controlling part 46 are connected the switches (SW1) 165 and (SW2) 167 provided in the operating section of the endoscope and the switch (SW3) 172 provided in the sheath of the video processor.

Figure 42:
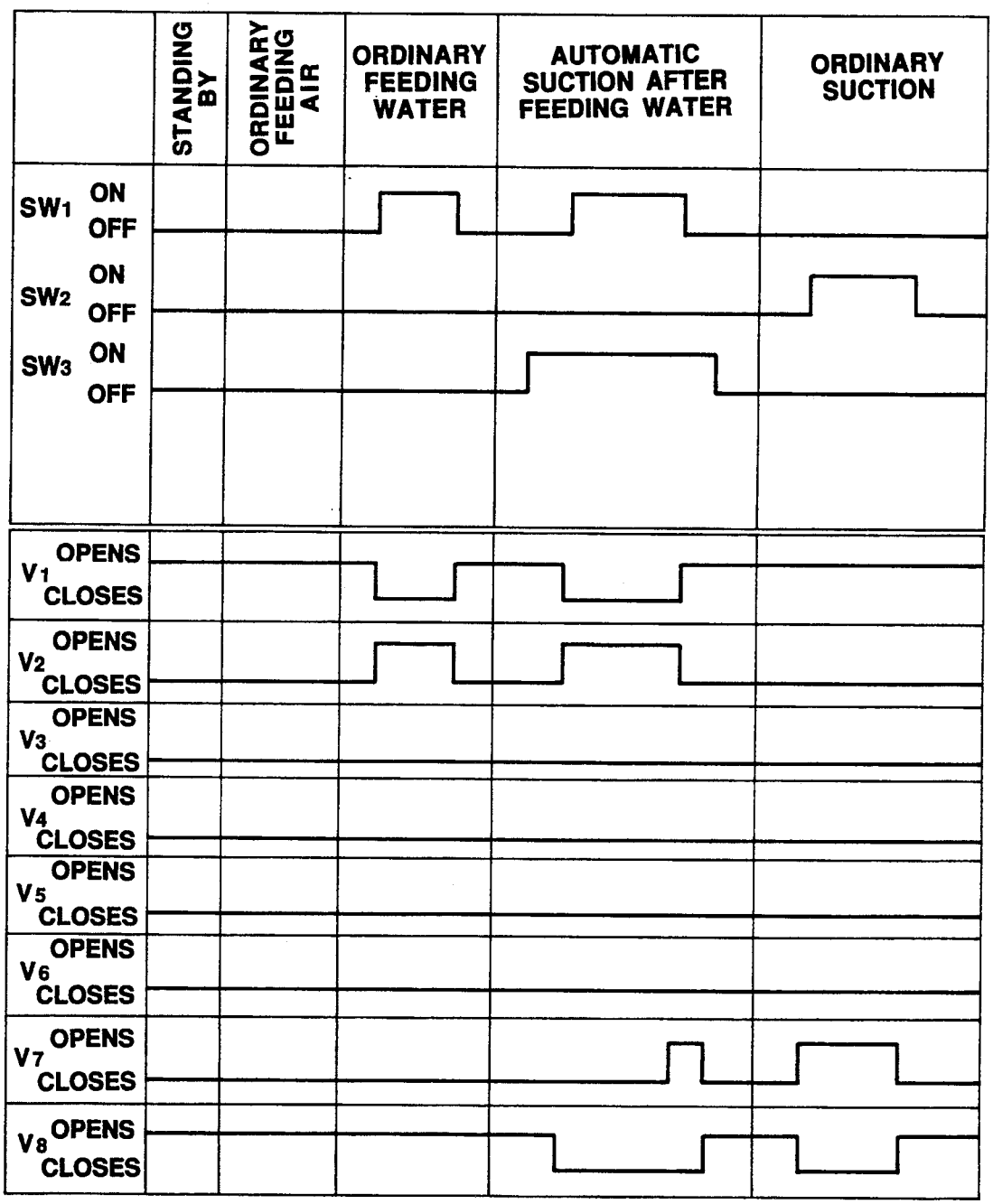
FIG. 42 is a time chart showing operation timings of respective switches and valves.

In such formation, as shown in the time chart in FIG. 42, air and water are usually fed by the operation of the button 163 and switch 165 provided in the operating section. That is to say, while only the first valve 23 is opened while standing by, when the venting hole 164 provided in the button 163 is clogged with a finger, the pressure of the air feeding pump 18 will open the check valve 166 and air will be fed to the insertable section at the tip. On the other hand, water is usually fed by switching the switch 165 on. When the switch 165 is switched on, the controlling part 46 will sense the signal, will close the first electromagnetic valve 23 and will simultaneously open the second electromagnetic valve 27 so that washing water will be fed to the water feeding pipeline 34.

Then, water is sucked by switching the switch 167 on. When the switch 167 is switched on, the controlling part 46 will sense the signal, will open the seventh electromagnetic valve 39 and will simultaneously close the eighth electromagnetic valve 43. In ending the suction, when the switch 167 is switched off, the seventh and eighth electromagnetic valves will return to standing by and the suction will end. By the way, even during the usual endoscope inspection, the suction pump 21 will be continuously operating. Therefore, while standing by, as shown in the timing chart in FIG. 42, the seventh electromagnetic valve 39 will be closed, the eighth electromagnetic valve 43 will be opened and the negative pressure within the sucking pipeline generated by the suction pump will escape to the atmosphere through the venting pipeline 42.

The automatic suction after feeding water is made by switching on the switch 172 which is to switch the usual feeding water and the automatic suction after feeding water over to each other. While the switch 172 is opened, when the button 163 is pushed in to switch the switch 165 on, the first electromagnetic valve 23 will close, at the same time the second electromagnetic valve 27 will open and the eighth electromagnetic valve 43 will also simultaneously close to stop the venting of the sucking pipeline to the atmosphere.

In this state, until the switch 165 is switched off, water will be fed and the suction pressure will be elevated while feeding water. When the switch 165 is switched off, the first electromagnetic valve 23 will open, the second electromagnetic valve 27 will simultaneously close, further the seventh electromagnetic valve 39 will also simultaneously open, will suck for a fixed time and will close after the fixed time elapses, as operatively connected therewith, the eighth electromagnetic valve 43 will open, standing by status will return and the automatic suction after feeding water will end.

Thus, in the modification, even by the automatic suction after feeding water, the same effects as in the sixth embodiment will be obtained.

By the way, in the modification, though controlled by the electromagnetic valves, the operating method is the same as that of the conventional mechanical air and water feeding and sucking controlling apparatus and therefore even an operator skilled in the conventional mechanical operating method can operate the apparatus of the modification without hesitation.

Also, the timing of the momentary automatic suction of these embodiments can be made freely variable. In these embodiments, poor evacuation of water droplets can be prevented after stoppage of feeding water.

FIG. 43 to 46 show the seventh embodiment.

Figure 43:
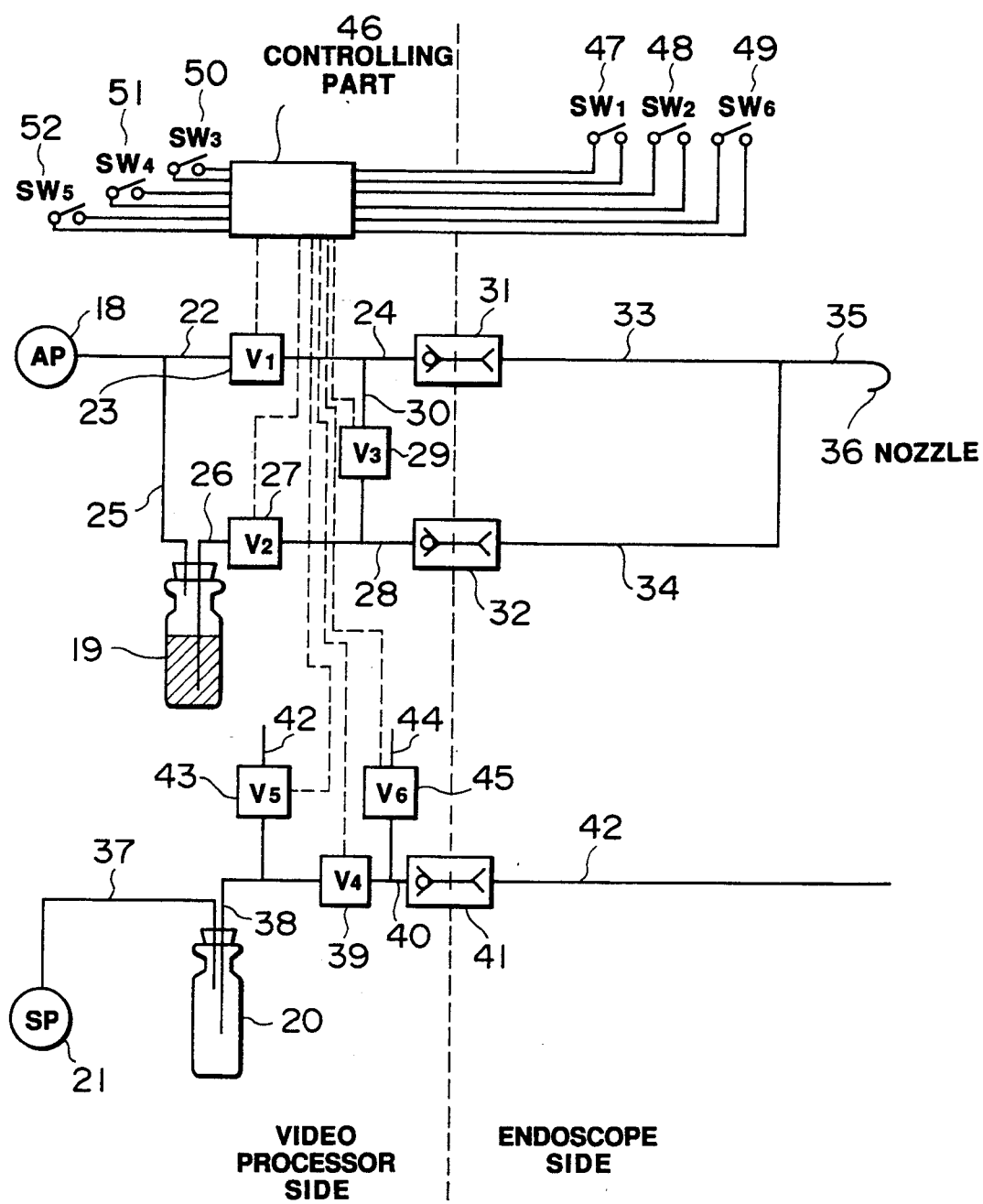
FIG. 43 is a pipeline diagram of an air and water feeding apparatus showing the seventh embodiment of the present invention.

In the pipeline diagram shown in FIG. 43, to a suction pump 18 is connected a first pipeline 22 provided with a first electromagnetic valve (V1) 23 to which is connected a second air feeding pipeline 24. In the course of the above-mentioned air feeding pipeline 22, a feeding water feeding air feeding pipeline 25 is branched and connected and is connected to communicate with a water feeding tank 19 to which is connected a first water feeding pipeline 26 and is connected a second water feeding pipeline 28 through a second electromagnetic valve (V2) 27. The above-mentioned second air feeding pipeline 24 and second water feeding pipeline 28 communicate with each other through an air feeding pipeline washing pipeline 30 fitted in the course with a third electromagnetic valve (V3) 29 provided in a position very close to the second water feeding pipeline 28. This is to prevent the formation of an air layer on the side of the second water feeding pipeline 28 rather than the third electromagnetic valve 29 of the air feeding pipeline washing pipeline 30 and will be compressed by the water feeding pressure while feeding water and, after stopping feeding water, in case the compressed air returns to the original volume, the washing water within the water feeding pipeline 34 and air feeding pipeline 35 will be pushed out and will flow gradually out of a nozzle 36.

The above-mentioned second air feeding pipeline 24 and second water feeding pipeline 28 are fitted at the ends, respectively with joints 31 and 32 so as to be connected, respectively, with an air feeding pipeline 33 and water feeding pipeline 34 on the endoscope side. These air feeding pipeline 33 and water feeding pipeline 34 join with each other on the tip side of the endoscope insertable section 13 to form an air feeding water feeding pipeline 35 which communicates with the nozzle 36 opening toward the observing window in the endoscope tip part. On the other hand, to a suction pump 21 is connected a first sucking pipeline 37 which is connected to a suction bottle 20. Further, to the suction bottle 20 is connects a second sucking pipeline 38 to which is connected a third sucking pipeline 40 through a fourth electromagnetic valve (V4) 39. This third sucking pipeline 40 is fitted at the end with a joint 41 so as to be connected with a sucking pipeline 42 on the endoscope side. A venting pipeline 42 is branched from the second sucking pipeline 38 and communicates with the atmosphere through a fifth electromagnetic valve (V5) 43. A mucous membrane adsorption releasing pipeline 44 is branched from the third sucking pipeline 40 and communicates with the atmosphere through a sixth electromagnetic valve (V6) 45. Further, the above-mentioned first to sixth electromagnetic valves 23, 27, 29, 39, 43 and 45 are respectively electrically connected to a controlling part 46. On the other hand, to this controlling part 46 are connected switches (SW1) 47 and (SW2) 48 provided in the operating section of the endoscope 11 and switches (SW3) 50, (SW4) 51 and (SW5) 52 provided in the sheath of the video processor 16.

Figure 44:
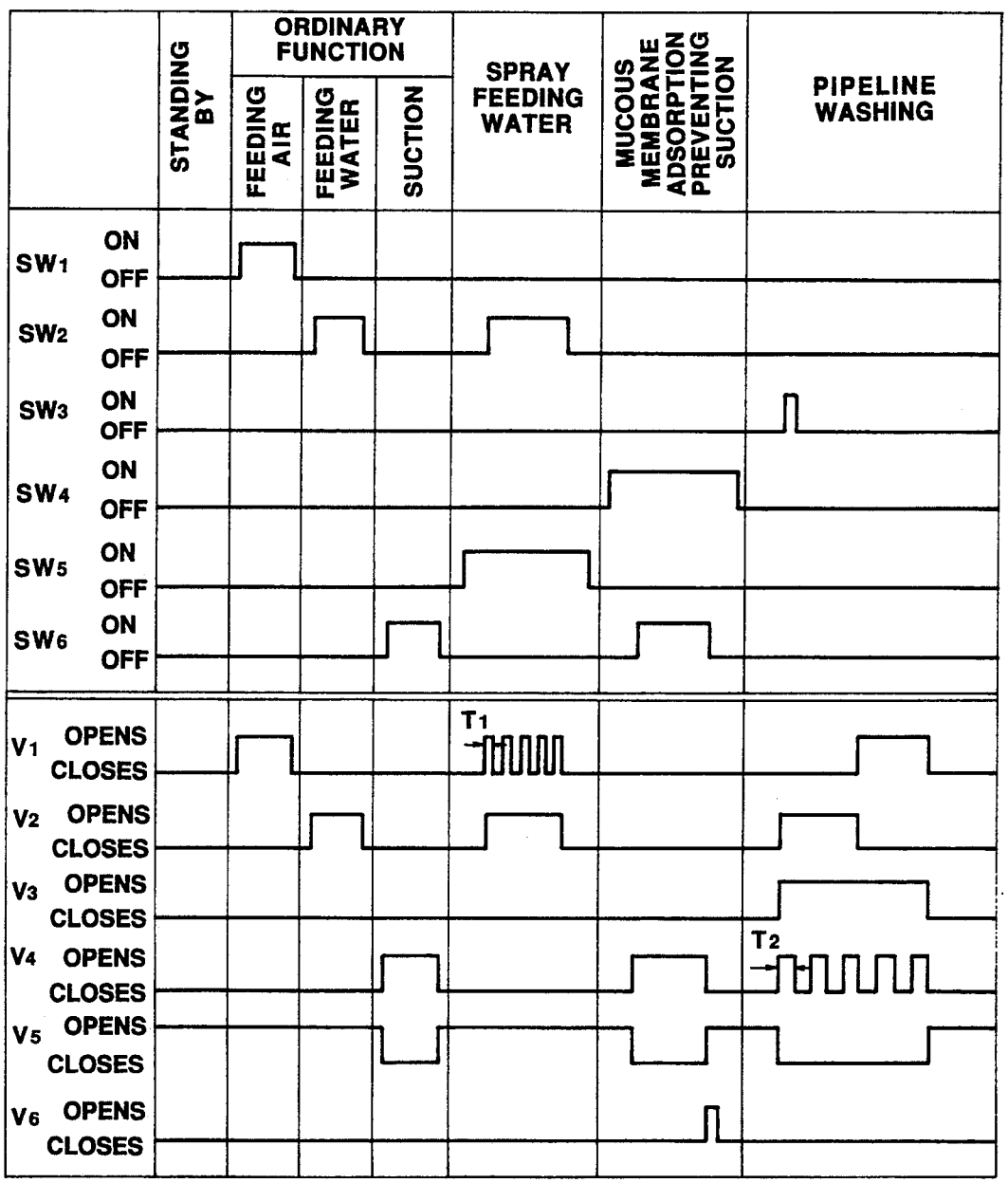
FIG. 44 is a time chart showing operation timings of respective switches and valves.

In such formation, as shown in the time chart in FIG. 44, during the usual endoscope inspection, air and water are fed by switching on/off the switches 47 and 48. That is to say, in the case of feeding air, when the switch 47 is switched on, by the controlling part 46, the first electromagnetic valve 23 will be opened and air will be fed through the air feeding pipeline 33. on the other hand, in feeding water, when the switch 48 is switched on, the controlling part 46 will open the second electromagnetic valve 27 in the same manner and washing water will be fed to the water feeding pipeline 34.

In the case of feeding spray water, first the switch 52 is switched on. This switch 52 is to switch usual feeding water and intermittent feeding air while feeding water over to each other. Therefore, when the switch 48 feeding water is switched on while this switch 52 is on, the controlling part 46 will sense the signal, will open the second electromagnetic valve 27, at the same time will automatically open the first electromagnetic valve 23 and thereafter will open and close only the first electromagnetic valve 23 intermittently at fixed intervals. When the water feeding ends, if the switch 48 is switched off, the first electromagnetic valve 23 and second electromagnetic valve 27 will both close.

Thereby, while feeding water, all the pressure of the air feeding pump can be intermittently applied to the water feeding pipeline and therefore, even if the water feeding tank is tumbled while feeding spray water, the air feeding pressure will not escape from the air feeding pipeline, feeding water will not become impossible and washing liquid will not flow back to the air feeding pipeline while feeding water.

Then, suction is made by switching on/off the switch 49 provided in the operating section. That is to say, when the switch 49 is switched on, by the controlling part 46, usually only the fifth electromagnetic valve 43 will be opened to stand by and, as operatively connected with switching on the switch 49, the fifth electromagnetic valve 43 will be closed and the fourth electromagnetic valve 39 will be opened to suck.

In order to control the mucous membrane for preventing the adsorption of the mucous membrane, first the switch 51 is switched on. This switch 51 is to switch the usual suction and the viscous membrane adsorption preventing suction over to each other. While this switch 51 is on, when the switch 49 is switched on, by the controlling part 46, the fifth electromagnetic valve 43 will be closed from standing by and at the same time the electromagnetic valve 39 will open to suck. When the switch 49 is switched off, as operatively connected with it, the fifth electromagnetic valve 43 will open, the fourth electromagnetic valve 39 will simultaneously close and further the sixth electromagnetic valve 45 will open for a fixed time and will then return to standing by. Thereby, the mucous membrane adsorption releasing pipeline 44 will temporarily communicate with the atmosphere, the negative pressure within the pipeline will be removed and the mucous membrane adsorption will be prevented.

Then, the endoscope pipeline is washed by momentarily switching the switch 50 on. That is to say, when the switch 50 is switched on, the controlling part 46 will sense it and will automatically make the following control. That is to say, the third electromagnetic valve 29 and second electromagnetic valve 26 will be simultaneously opened, the air feeding pipeline 33 and water feeding pipeline 34 will be washed for a fixed time and then the second electromagnetic valve 26 will be closed. Thereby, the washing of the air feeding pipeline 33 and water feeding pipeline 34 will end. Then, both pipelines will be controlled to remove water, the first electromagnetic valve 23 will be opened to remove water in the water feeding pipeline 34 and air feeding pipeline 33 and then will be closed and the third electromagnetic valve 29 will be also simultaneously closed. Thereby, both pipelines will be washed and have water removed by the operation of one touch of pushing the switch 50.

On the other hand, on the sucking pipeline side, when the switch 50 is switched on, both of the fifth electromagnetic valve 43 and sixth electromagnetic valve 45 will be closed and the fourth electromagnetic valve 39 will intermittently open, will suck up washing water from the endoscope tip, will wash the pipeline for a fixed time and will return to standing by status to complete washing.

Thus, in the seventh embodiment, even if the water feeding tank is tumbled while feeding spray water, the air feeding pressure will not escape from the air feeding pipeline, feeding water will not become impossible, therefore the observing window will be able to be washed in a wide range, spray water will be able to be fed with a good water cut and no washing liquid will flow back to the air feeding pipeline while feeding water.

Figure 45:
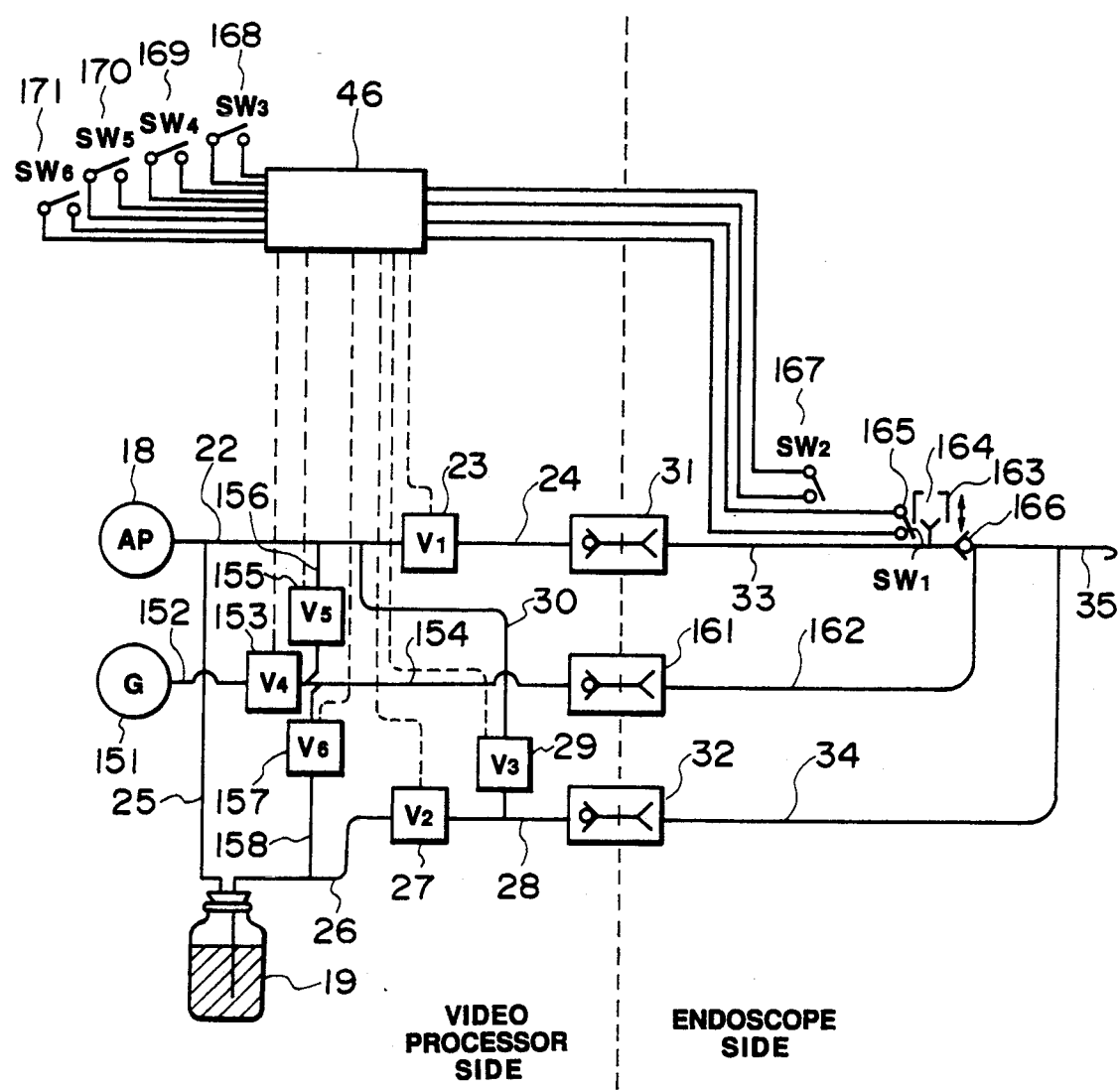
FIG. 45 is a pipeline diagram of an air and water feeding apparatus showing a modification.
Figure 46:
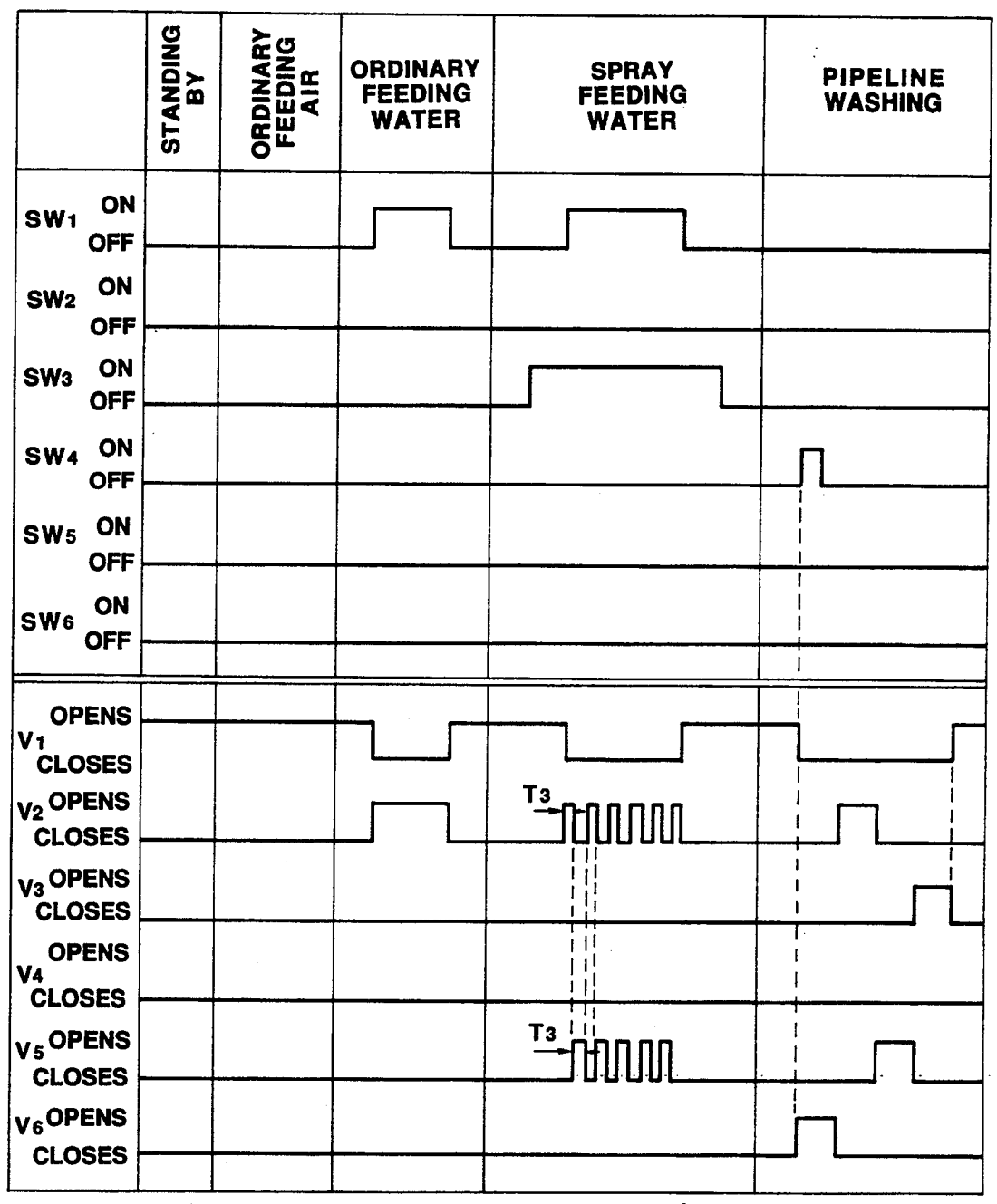
FIG. 46 is a time chart showing operation timings of respective switches and valves of a modification.

FIGS. 45 and 46 are of a modification of the seventh embodiment.

In the pipeline diagram shown in FIG. 45, to an air feeding pump 18 is connected a first air feeding pipeline 22 to which is connected a second air feeding pipeline 24 through a first electromagnetic valve (V1) 23. Further, in the course of the first air feeding pipeline 22, a water feeding air feeding pipeline 25 is branched and connected and is connected to a water feeding tank 19 to which is further connected a first water feeding pipeline 26 and is connected a second water feeding pipeline 28 through a second electromagnetic valve (V2) 27. The above-mentioned first air feeding pipeline 22 and second water feeding pipeline 28 communicate with each other through a water feeding pipeline water removing pipeline 30 having a third electromagnetic valve (V3) 29 which is provided near the branching part of the second water feeding pipeline 28 and water feeding pipeline water removing pipeline 30. To a gas bottle 151 filled with a nonflammable gas is connected a first gas pipeline 152 and is further connected a second gas pipeline used also as an air feeding pipeline feeding a gas and air through a fourth electromagnetic valve (V4) 153. The above-mentioned second gas pipeline 154 and first air feeding pipeline 22 communicate with each other through a gas pipeline water removing air feeding pipeline 156 having a fifth electromagnetic valve (V5) 155. Further the second gas pipeline 154 and first water feeding pipeline 26 communicate with each other through a gas pipeline (which is also an air feeding pipeline) washing pipeline 158 having a sixth electromagnetic valve (V6) 157. By the way, in order to positively remove water, the gas pipeline water removing air feeding pipeline 156 communicates with the second gas pipeline 154 on the side of the gas bottle 151 rather than the gas pipeline washing pipeline 158. The second air feeding pipeline 24, second gas pipeline 154 and second water feeding pipeline 28 are fitted at the ends, respectively, with joints 31, 161 and 32 so as to be connected respectively to an air feeding pipeline 33, gas pipeline 162 and water feeding pipeline 34 on the endoscope side. In the course within the endoscope, the air feeding pipeline 33 communicates with a button 163 provided in the operating section and opens in a venting hole 164 provided in the upper part of the button 163. This button 163 is provided so as to be free to advance and retreat and is further provided with such switch (SW1) 165 as will be switched on when the button 163 is pushed in. The air feeding pipeline 33 is provided with a check valve 166 in a position on the side of the insertable section rather than the button 163 provided in the operating section. A gas pipeline 162 communicates with the insertable section on the tip side. The air feeding pipeline 33 and water feeding pipeline 34 join with each other on the tip side of the endoscope insertable section to form an air and water feeding pipeline 35. The above-mentioned first to sixth electromagnetic valves 23, 27, 29, 153, 155 and 157 are respectively electrically connected to a controlling part 46. On the other hand, to this controlling part 46 are connected switches (SW1) 165 and (SW2) 167 provided in the operating section of the endoscope and switches (SW3) 168, (SW4) 169, (SW5) 170 and (SW6) 171 provided in the sheath of the video processor.

In such formation, as shown in the time chart in FIG. 46, usually air and water are fed by operating the button 163 and switch 165 provided in the operating section. That is to say, in feeding air, while standing by and only the first valve 23 is opened, when the venting hole 164 provided in the button 163 is clogged with a finger, the pressure of the air feeding pump 18 will open the check valve 166 to feed air to the insertable section at the tip. On the other hand, water is fed by switching the switch 165 on. When the switch 165 is switched on, the controlling part 46 will sense the signal, will close the first electromagnetic valve 23 and will simultaneously open the second electromagnetic valve 27 so that washing water will be fed to the water feeding pipeline 34 to feed water.

Then, spray water is fed by switching the switch 168 on. The switch 168 is for switching usual feeding water and spray feeding water over to each other. Therefore, while the switch 168 is on, when the switch 165 feeding water is switched on, the controlling part 46 will sense the signal, will close the first electromagnetic valve 23, at the same time, will intermittently open and close the second electromagnetic valve 27, and simultaneously with it, will intermittently open and close also the second electromagnetic valve 27. However, the fifth electromagnetic valve 155 and second electromagnetic valve 27 will be alternately opened and closed so that the fifth electromagnetic valve 155 will close when the second electromagnetic valve 27 opens but will open when the second electromagnetic valve 27 closes. When feeding water ends, if the switch 165 is switched off, both of the second electromagnetic valve 27 and fifth electromagnetic valve 155 will close.

The pipeline is washed by momentarily switching on the switch 169. That is to say, when the switch 169 is switched on, the controlling part 46 will sense it and will automatically control as follows. First of all, the first electromagnetic valve 23 will close from standing by. Simultaneously with it, the sixth electromagnetic valve 157 will be opened, the gas pipeline 162 will be washed for a fixed time and then the sixth electromagnetic valve 157 will be closed so that the washing of the gas pipeline 162 and the air feeding pipeline 33 on the tip side from the check valve 166 will end. At the same time as the sixth electromagnetic valve 157 closes, the second electromagnetic valve 27 will open so that the water feeding pipeline 34 will be washed for a fixed time and the second electromagnetic valve 27 will be closed. When the second electromagnetic valve 27 closes, the fifth electromagnetic valve 155 will open, will remove water in the gas pipeline and the air feeding pipeline on the tip side from the check valve 166 and will close when a fixed time elapses. When the fifth electromagnetic valve 155 closes, the third electromagnetic valve 29 will open, will remove water in the water feeding pipeline 34 and will then close. At the same time as the third electromagnetic valve 29 closes, the first electromagnetic valve 23 will return to standing by status.

Thus, even in the spray water feeding repeating intermittently feeding air and feeding water in the modification of the seventh embodiment, the same effects as in the seventh embodiment will be obtained.

By the way, the switch 167 is for controlling sucking, the switch 170 is for controlling feeding a gas and the switch 171 is for switching the mucous membrane adsorption preventing sucking and the usual sucking over to each other.

By the way, the timing for connecting and disconnecting the electromagnetic valves of these embodiments can be made variable to 0.1 to 1 second.

In these embodiments, when spray water is fed, the air within the air feeding pipeline will not be compressed while feeding water, the washing water will not flow back into the air feeding pipeline, the air compressed after stopping feeding water will not expand and will not push the washing water out of the air feeding pipeline, water drops will not flow out of the nozzle after stopping feeding water and poor control of the evacuation of water droplets will be able to be prevented.

Further, as the third electromagnetic valve 62 is provide near the branching part of the water feeding pipeline water removing pipeline 63 from the second water feeding pipeline 61, no air layer deteriorating the evacuation of water droplets will remain and the response of the stoppage of feeding water will be very good.

It is needless to say that the air feeding and water feeding apparatus in these embodiments are not limited to those having a nozzle opening toward an observing window but may be applied to those having a nozzle opening to wash the body wall.

In this invention, it is apparent that working modes different in a wide range can be formed on the basis of this invention without departing from the spirit and scope of the invention. This invention is not restricted by any specific embodiment except being limited by the appended claims.

What is claimed is:

1. A line control apparatus for an endoscope, comprising:
    a body separate from said endoscope and having line control means for controlling air feed, and water feed;
    a leading line connected to the outside of said body, for communicating said line control means with an air feed pump provided on the outside of said endoscope; and
    a single connecting pipeline for communicating and connecting said line control means to a plurality of lines provided within the endoscope wherein said connecting pipeline contains said leading line and said plurality of lines.

2. An endoscope pipeline controlling apparatus according to claim 1 wherein the resistance to liquid and/or air pressure at the time of feeding a liquid of a water feeding pipeline of an endoscope not connected to this apparatus is made larger than the resistance at the time of feeding air of the air feeding pipeline.

3. A line control apparatus for an endoscope as recited in claim 1, further comprising:
    a light source apparatus connected to said line control means through said connecting pipeline, said light source apparatus being internally provided with a light source feeding an illuminating light to the endoscope and provided with said air feed pump,
    wherein said line control means is provided separately from said light source apparatus, and
    wherein said line control means includes a controlling means for feeding air for a fixed time simultaneously with or before starting feeding water.

4. An endoscope pipeline controlling apparatus comprising:
- a pipeline controlling means for controlling feeding air and feeding water;
- a leading pipeline for connecting said pipeline controlling means with an air feeding pump provided outside an endoscope; and
- a connecting pipeline for connecting said pipeline controlling means with pipelines provided within the endoscope; wherein said pipeline controlling means connects a first air feeding pipeline communicating with the air feeding pump to an electromagnetic valve to which is connected a second air feeding pipeline and said first air feeding pipeline is branched to provide a water feeding air feeding pipeline which is connected to a water feeding tank to which is connected a first water feeding pipeline having an electromagnetic valve to which is connected a second water feeding pipeline.

5. An endoscope pipeline controlling apparatus according to claim 4 wherein said pipeline controlling means connects the first air feeding pipeline and second water feeding pipeline so they communicate with each other through a pipeline fitted with an electromagnetic valve.

6. An endoscope pipeline controlling apparatus according to claim 4 wherein said pipeline controlling means connects the first water feeding pipeline and second air feeding pipeline so they communicate with each other through a pipeline fitted with an electromagnetic valve.

7. An endoscope pipeline controlling apparatus according to claim 4 wherein said pipeline controlling means has a suction pump and a suction tank connected with each other through a first sucking pipeline, and a second sucking pipeline fitted with an electromagnetic valve is connected to said suction tank, further a third sucking pipeline is connected to the electromagnetic valve and a venting pipeline fitted with an electromagnetic valve is branched and connected to said second sucking pipeline.

8. An endoscope pipeline controlling apparatus according to claim 7, wherein a pipeline for adjusting a sucking amount communicating with the atmosphere through an electromagnetic valve and orifice is branched and connected to said third sucking pipeline.

9. An endoscope pipeline controlling apparatus according to claim 7 further comprising:
- a venting means connecting said second sucking pipeline to communicate with the atmosphere when waiting for sucking; and
- a sucking controlling means stopping venting by said venting means during the water feeding operation and automatically making a sucking operation when the water feeding operation ends.

10. An endoscope pipeline controlling apparatus according to claim 4 wherein a gas pipeline from a gas tank storing a nonflammable gas is connected to the second air feeding pipeline and is fitted with an electromagnetic valve.

11. An endoscope pipeline controlling apparatus according to claim 4 wherein said pipeline controlling means controls the valve provided in said air feeding pipeline to intermittently open and close and intermittently feeds air to said air feeding pipeline from the air feeding pump.

12. An endoscope pipeline controlling apparatus comprising:
- a pipeline controlling means for controlling feeding air and feeding water;
- a leading pipeline for connecting said pipeline controlling means with an air feeding pump provided outside an endoscope;
- a connecting pipeline for connecting said pipeline controlling means with pipelines provided within the endoscope; and
- a connecting cord extended from the endoscope, having a connector at one end and connected through this connector to a light source apparatus internally provided with an air feeding pump and a branched connecting cord branched from said connecting cord, wherein said light source apparatus is connected to said pipeline controlling means and internally provided with said leading pipeline and connecting pipeline.

13. An endoscope pipeline controlling apparatus comprising:
- a pipeline controlling means for controlling feeding air and feeding water;
- a leading pipeline for connecting said pipeline controlling means with an air feeding pump provided outside an endoscope;
- a connecting pipeline for connecting said pipeline controlling means with pipelines provided within the endoscope;
- an engaging means for removably engaging a connecting cord of said endoscope having an air feeding and water feeding means including an air feeding pipeline, water feeding pipeline and nozzle;
- a release instructing means for outputting a release instruction for releasing the engagement of said engaging means and endoscope connecting cord; and
- a controlling means for giving an instruction to said air feeding and water feeding means to feed at least one of air and water for a predetermined time after receiving a release instruction output by said release instructing means and for releasing the engagement of said engaging means and endoscope in order that the endoscope may be pulled out of said engaging means after a predetermined time.

14. An endoscope pipeline controlling apparatus according to claim 13 wherein said pressure switching means is to switch and adjust the pressure of the air feeding pump or suction pump to a pressure set in advance in response to the kind of the endoscope.

15. An endoscope pipeline controlling apparatus comprising:
- a pipeline controlling means for controlling feeding air and feeding water;
- a leading pipeline for connecting said pipeline controlling means with an air feeding pump provided outside an endoscope;
- a connecting pipeline for connecting said pipeline controlling means with pipelines provided within the endoscope; and
- a sensing means for sensing the kind of an endoscope whereby, when an endoscope provided with a distinguishing means for distinguishing the kind of the endoscope which is connected, the kind of the endoscope will be sensed by the distinguishing means of said endoscope;
- a pressure adjusting means for adjusting the operating pressure of at least any one of an air feeding operation, a liquid feeding operation and a suction operation; and a pressure switching means for switching the operating pressure of said pressure adjusting means in response to the kind of said endoscope sensed by said sensing means.

16. An endoscope pipeline controlling apparatus according to claim 15, wherein said sensing means is a decoder for discriminating output data from a memory memorizing respective endoscope kind codes.

17. An endoscope pipeline controlling apparatus according to claim 15 wherein said pressure adjusting means is an air feeding pump or suction pump.

18. An endoscope pipeline controlling apparatus according to claim 15 wherein said sensing means detects resistance of a resistor as an endoscope distinguishing means.

19. An endoscope pipeline controlling apparatus according to claim 15 wherein said sensing means is an optical mark reader which reads bar codes as an endoscope distinguishing means.

20. An endoscope system comprising:
a light source apparatus internally provided with a light source feeding an illuminating light to an endoscope and provided with a suction pump;
a pipeline controlling means for controlling feeding air and feeding water and provided separately from said light source apparatus; and
an endoscope connected with said light source apparatus and pipeline controlling apparatus, wherein said pipeline controlling means connects a first air feeding pipeline communicating with the air feeding pump to an electromagnetic valve to which is connected a second air feeding pipeline and said first air feeding pipeline is branched to provide a water feeding air feeding pipeline which is connected to a water feeding tank to which is connected a first water feeding pipeline having an electromagnetic valve to which is connected a second water feeding pipeline.

21. An endoscope system according to claim 20 wherein said pipeline controlling means connects the first air feeding pipeline and second water feeding pipeline to communicate with each other through a pipeline fitted with an electromagnetic valve.

22. An endoscope system according to claim 20, wherein said pipeline controlling means connects the first water feeding pipeline and second air feeding pipeline to communicate with each other through a pipeline fitted with an electromagnetic valve.

23. An endoscope system according to claim 20, wherein said pipeline controlling means has a suction pump and suction tank connected with each other through a first sucking pipeline, on the other hand, a second sucking pipeline fitted with an electromagnetic valve is connected to said suction tank, further a third sucking pipeline is connected to the electromagnetic valve and a venting pipeline fitted with an electromagnetic valve is branched and connected to said second sucking pipeline.

24. An endoscope system according to claim 23 wherein a pipeline for adjusting a sucked amount communicating with the atmosphere through an electromagnetic valve and orifice is branched and connected to said third sucking pipeline.

25. An endoscope system according to claim 23 further comprising:
a venting means connecting said sucking pipeline to communicate with the atmosphere when waiting for sucking; and
a sucking controlling means stopping venting by said venting means during the water feeding operation and automatically making a sucking operation when the water feeding operation ends.

26. An endoscope system according to claim 20 wherein said pipeline controlling means controls the valve provided in said air feeding pipeline to intermittently open and close and intermittently feeds air to said air feeding pipeline from the air feeding pump.

* * * * *